(12) United States Patent
Thompson et al.

(10) Patent No.: US 8,785,173 B2
(45) Date of Patent: Jul. 22, 2014

(54) METHODS FOR PURIFICATION OF VIRUSES

(75) Inventors: Mark Thompson, Morgan Hill, CA (US); Janice Wee, San Mateo, CA (US); Akanksha Nagpal, San Jose, CA (US)

(73) Assignee: MedImmune, LLC, Gaithersburg, MD (US)

( * ) Notice: Subject to any disclaimer, the term of this patent is extended or adjusted under 35 U.S.C. 154(b) by 318 days.

(21) Appl. No.: 13/120,638

(22) PCT Filed: Sep. 24, 2009
(Under 37 CFR 1.47)

(86) PCT No.: PCT/US2009/058174
§ 371 (c)(1),
(2), (4) Date: Aug. 15, 2011

(87) PCT Pub. No.: WO2010/036774
PCT Pub. Date: Apr. 1, 2010

(65) Prior Publication Data
US 2012/0219588 A1    Aug. 30, 2012

Related U.S. Application Data

(60) Provisional application No. 61/099,749, filed on Sep. 24, 2008, provisional application No. 61/104,933, filed on Oct. 13, 2008, provisional application No. 61/122,456, filed on Dec. 15, 2008, provisional application No. 61/187,721, filed on Jun. 17, 2009, provisional application No. 61/222,131, filed on Jul. 1, 2009.

(51) Int. Cl.
*C12N 7/02* (2006.01)
(52) U.S. Cl.
USPC ........................................ 435/239
(58) Field of Classification Search
None
See application file for complete search history.

(56) References Cited

U.S. PATENT DOCUMENTS

| | | | |
|---|---|---|---|
| 5,045,454 A | 9/1991 | Bertheussen | |
| 5,118,513 A | 6/1992 | Mehansho et al. | |
| 5,166,057 A | 11/1992 | Palese et al. | |
| 5,786,199 A | 7/1998 | Palese | |
| 5,820,871 A | 10/1998 | Palese | |
| 5,824,536 A | 10/1998 | Webster et al. | |
| 5,840,520 A | 11/1998 | Clarke et al. | |
| 5,854,037 A | 12/1998 | Palese et al. | |
| 6,001,634 A | 12/1999 | Palese et al. | |
| 6,245,549 B1 | 6/2001 | Ewasyshyn et al. | |
| 6,455,298 B1 | 9/2002 | Groner et al. | |
| 6,544,424 B1 | 4/2003 | Shevitz | |
| 6,544,785 B1 | 4/2003 | Palese et al. | |
| 6,593,140 B1 | 7/2003 | Field | |
| 6,649,372 B1 | 11/2003 | Palese et al. | |
| 6,825,306 B2 | 11/2004 | Halasa et al. | |
| 6,887,699 B1 | 5/2005 | Palese et al. | |
| 6,951,754 B2 | 10/2005 | Hoffmann | |
| 7,262,045 B2 | 8/2007 | Schwartz et al. | |
| 7,790,434 B2 | 9/2010 | Duke et al. | |
| 8,202,726 B2 | 6/2012 | Liu et al. | |
| 2002/0164770 A1 | 11/2002 | Hoffmann | |
| 2003/0035814 A1 | 2/2003 | Kawaoka et al. | |
| 2003/0108860 A1 | 6/2003 | Reiter et al. | |
| 2004/0042972 A1 | 3/2004 | Truong-Le et al. | |
| 2004/0142003 A1 | 7/2004 | Palese et al. | |
| 2005/0019891 A1 | 1/2005 | Fouchier et al. | |
| 2005/0032043 A1 | 2/2005 | Palese et al. | |
| 2005/0037487 A1 | 2/2005 | Kawaoka et al. | |
| 2005/0118140 A1 | 6/2005 | Vorlop et al. | |
| 2005/0118698 A1 | 6/2005 | Vorlop et al. | |
| 2005/0158342 A1 | 7/2005 | Kemble et al. | |
| 2005/0186224 A1 | 8/2005 | Buchholz et al. | |
| 2005/0186563 A1 | 8/2005 | Hoffmann et al. | |
| 2005/0221489 A1 | 10/2005 | Garcia-Sastre et al. | |
| 2005/0266026 A1 | 12/2005 | Hoffmann et al. | |
| 2006/0019350 A1 | 1/2006 | Palese et al. | |
| 2006/0160130 A1 | 7/2006 | Jin et al. | |
| 2006/0171955 A1* | 8/2006 | Alonso-Caplen et al. | . 424/186.1 |
| 2006/0188977 A1* | 8/2006 | Schwartz et al. | .......... 435/235.1 |

(Continued)

FOREIGN PATENT DOCUMENTS

| | | |
|---|---|---|
| CN | 101189326 | 8/2006 |
| CN | 101426905 | 1/2007 |

(Continued)

OTHER PUBLICATIONS

Belshe, R. B., et al. "The Efficacy of Live Attenuated, Cold-adapted, Trivalent, Intranasal Influenza virus Vaccine in Children." N.Eng. J.Med. (1998) 338: 1405-1412.

(Continued)

*Primary Examiner* — Mary E Mosher
*Assistant Examiner* — Myron Hill
(74) *Attorney, Agent, or Firm* — Grant IP, Inc.

(57) ABSTRACT

The present invention provides methods for the purification of cell-associated viruses from adherent cells (e.g., MDCK or Vero cells). In particular, the present invention provides purification methods for the production of immunogenic compositions comprising a live attenuated cell-associated virus (e.g., an attenuated respiratory syncytial virus (RSV) or cold-adapted, and/or temperature sensitive influenza virus) that result in levels of host cell DNA (HCD), host cell protein (HCP) and non-specific endonuclease (e.g., Benzonase), which are below the specifications required by regulatory agencies. The immunogenic compositions can be used to actively immunize subjects or to generate antibodies for a variety of uses, including passive immunization and diagnostic immunoassays.

9 Claims, 20 Drawing Sheets

(56) References Cited

U.S. PATENT DOCUMENTS

| | | | |
|---|---|---|---|
| 2006/0286591 | A1 | 12/2006 | Duke et al. |
| 2007/0031941 | A1 | 2/2007 | Duke et al. |
| 2007/0249019 | A1* | 10/2007 | Kang et al. .................. 435/69.1 |
| 2008/0286850 | A1 | 11/2008 | Liu et al. |
| 2010/0098725 | A1 | 4/2010 | Liu et al. |

FOREIGN PATENT DOCUMENTS

| | | |
|---|---|---|
| JP | 2004-135665 | 5/2004 |
| WO | WO 98/22588 | 5/1998 |
| WO | WO 01/16294 | 3/2001 |
| WO | WO 01/83794 | 11/2001 |
| WO | WO 03/091401 | 11/2003 |
| WO | WO 03/093463 | 11/2003 |
| WO | WO 2005/014862 | 2/2005 |
| WO | WO 2005/062820 | 7/2005 |
| WO | WO 2005/080556 | 9/2005 |
| WO | WO 2005/113758 | 12/2005 |
| WO | WO 2006/041819 | 4/2006 |
| WO | WO 2007/124327 | 11/2007 |
| WO | WO 2008/105931 | 9/2008 |
| WO | WO 2010/036774 | 4/2010 |

OTHER PUBLICATIONS

Brown et al., "Infective virus substructure from vesicular stomatitis virus," 1967, J. Virol. 1:368-373.
Chin et al., "Field evaluation of a respiratory syncytial virus vaccine and a trivalent parainfluenza virus vaccine in a pediatric population," 1969, Am. J. Epidemiol. 89:449-63.
Collins et al., 2005, Proc. Am. Thorac. Soc. 2: 166-173.
Crowe et al., 1993, Vaccine 11:1395-1404.
Crowe et al., 1994, Vaccine 12: 691-699.
Crowe et al., 1995, Vaccine 13:847-855.
Downing et al., "Active respiratory syncytical virus purified by ino-exchange chromatography: characterization of binding and elution requirements," Journal of Virological Methods, vol. 38, No. 2, Aug. 1, 1992, pp. 215-228.
Fodor et al. (1999) Rescue of influenza A virus from recombinant DNA. *J. Virol* 73:9679-9682.
Gharpure et al., 1969, J. Virol. 3: 414-21.
Griffiths, 1999, Dev Biol Stand. Basel, Karger, vol. 98, pp. 153-157.
Hoffman et al., 2002, "Rescue of influenza B virus from eight plasmids", PNAS 99: 11411-11416.
Hoffmann and Webster (2000), Unidirectional RNA polymerase I-polymerase II transcription system for the generation of influenza A virus from eight plasmids, 81:2843-2847.
Hoffmann et al., 2000, "A DNA transfection system for generation of influenza A virus from eight plasmids", PNAS 97(11):6108-6113.
Jackson et al., "Safety of a trivalent live attenuated intranasal influenza vaccine, FluMist, administered in addition to parenteral trivalent inactivated influenza vaccine to seniors with chronic medical conditions," 1999, Vaccine, 17:1905.
Kapikian et al., 1969, Am. J. Epidemiol. 89:405-421.
Karron et al., 1997, J Infect Dis. 176:1428-1436.
Karron et al., J. of Infect. Diseases 191: 1093-1140.
Kim et al., 1971, Pediatrics 48: 745-755.
Leighton et al., 1970, Cancer, 26:1024.
Lonardo et al., "Rapid Methods for identification of poliovirus isolates and determination of polio neutralizing antibody titers in human sera . . . " J Virol Methods, 2002 vol. 101, (1-2), p. 189-196.
Mills et al., 1971, J Immunol. 107:123-130.
Neumann et al. (1999) Generation of influenza A virus entirely from cloned cDNAs. *Proc Natl Acad Sci USA* 96:9645-9650.
Nichol et al. 1999, "Effectiveness of live. attenuated Intranasal influenza virus vaccine in healthy, working adults: a randomized controlled trial", JAMA 282:137-44.
Nowinski and Hays, 1978, J. Virol., 27: 13-18.
Peeper, et al., 2002, Nat Cell Biol., 4:148-53.
Pringle et al., Vaccine 1993 11:473-478.
Radaeva, I. F., et al. "Development and Certification of Libraries of the MDCK Continuous Cell Line for Production of Influenza Vaccine." Vopr.Virusol (2005) 50:43-46 Abstract with English language Translation.
Robbins and Kawakawi, 1996, Curr. Opin. Immunol. 8: 628-636.
Stiles, C. D., et al. "Growth Control of Heterologous Tissue Culture Cells in the Congenitally Athymic Nude Mouse." Cancer Res. (1976) 36: 1353-1360.
Wang and Duke; "Cloning of the canine RNA polymerase 1 promoter and establishment of reverse genetics for influenza A and B in MDCK cells," Oct. 23, 2007, J. Virol., 4:102.
Whitehead et al., 1999, J. Virol. 73: 3438-3442.
Wood, J. M., 2001, Philos. Trans. R. Soc. Lond. B. Biol. Sci., 356:1953.
International Preliminary Report on Patentability dated: Mar. 29, 2011 in International Application No. PCT/US2009/58174 filed on: Sep. 24, 2009 and published as WO 10/036774 on: Apr. 1, 2010.
International Search Report and Written Opinion mailed on: Nov. 25, 2009 in International Application No. PCT/US2009/58174 filed on: Sep. 24, 2009 and published as WO 10/036774 on: Apr. 1, 2010.
Extended European Search Report dated Jul. 27, 2012 in European Application No. EP09816835 filed: Sep. 24, 2009 based on International Application No. PCT/US2009/058174.

* cited by examiner

FIG. 7A
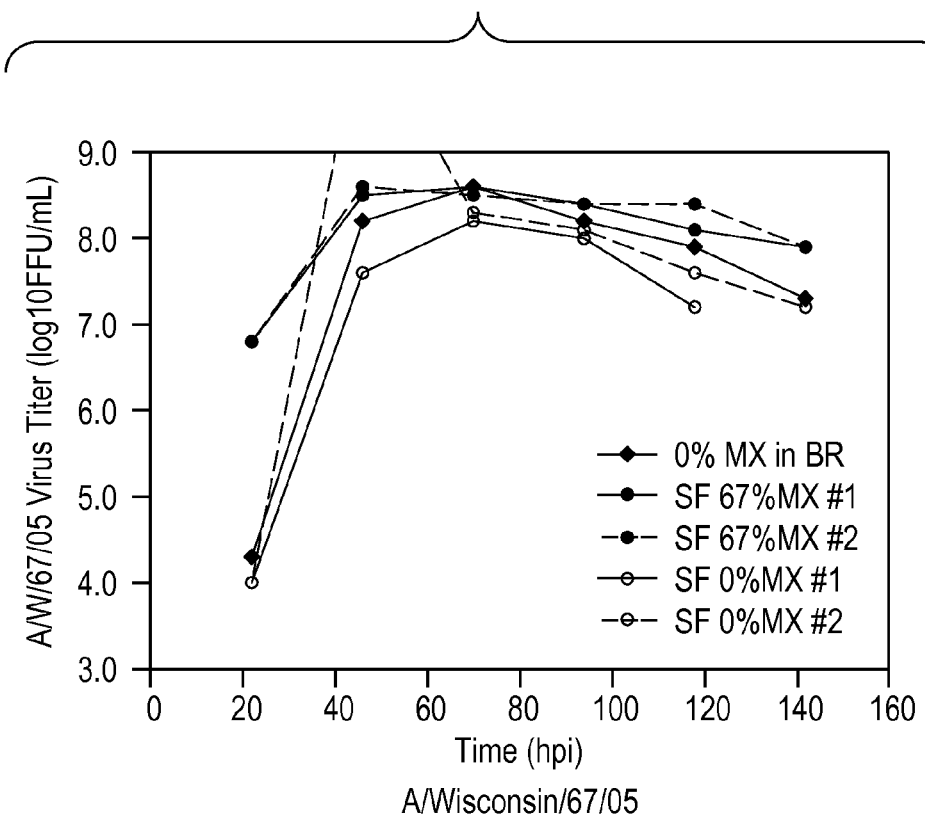
A/Wisconsin/67/05
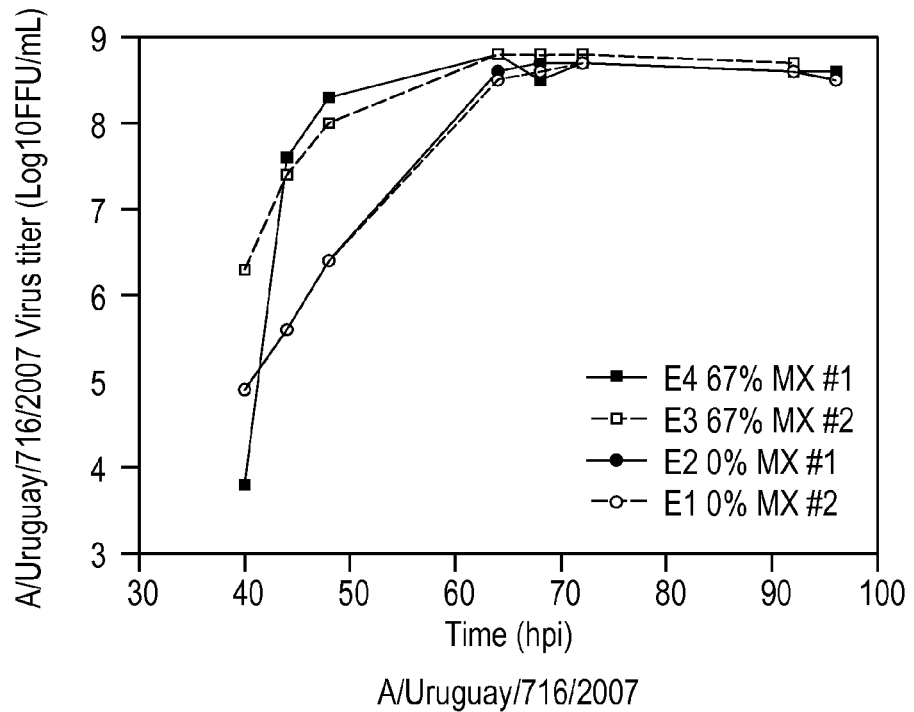
A/Uruguay/716/2007

FIG. 7B
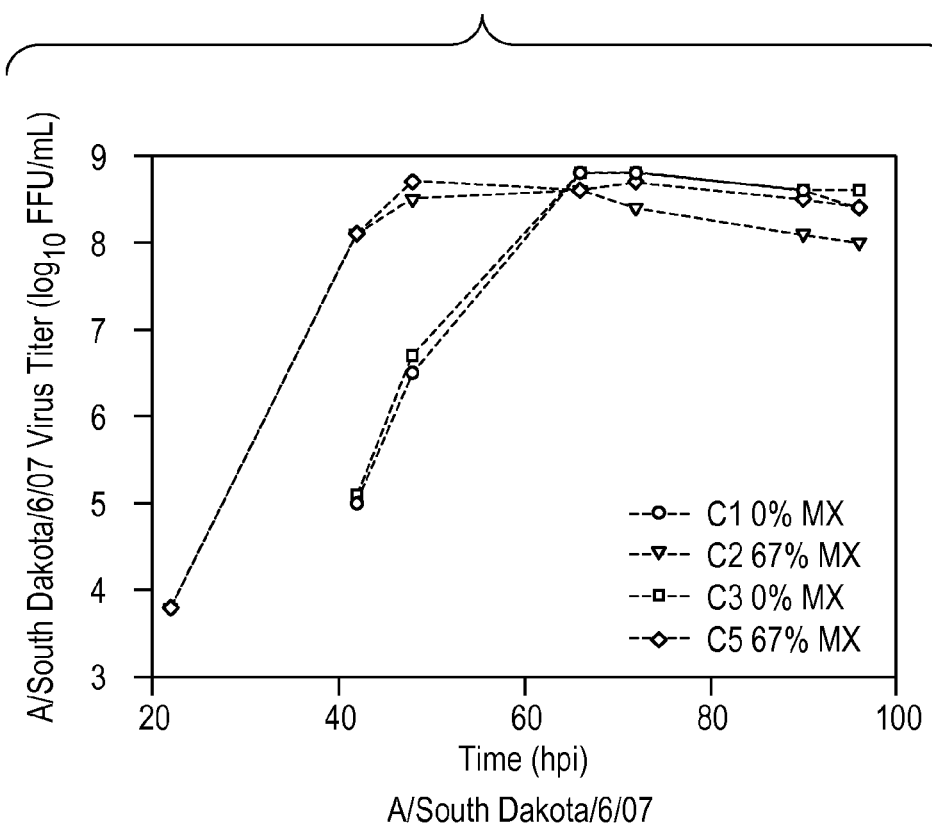
A/South Dakota/6/07
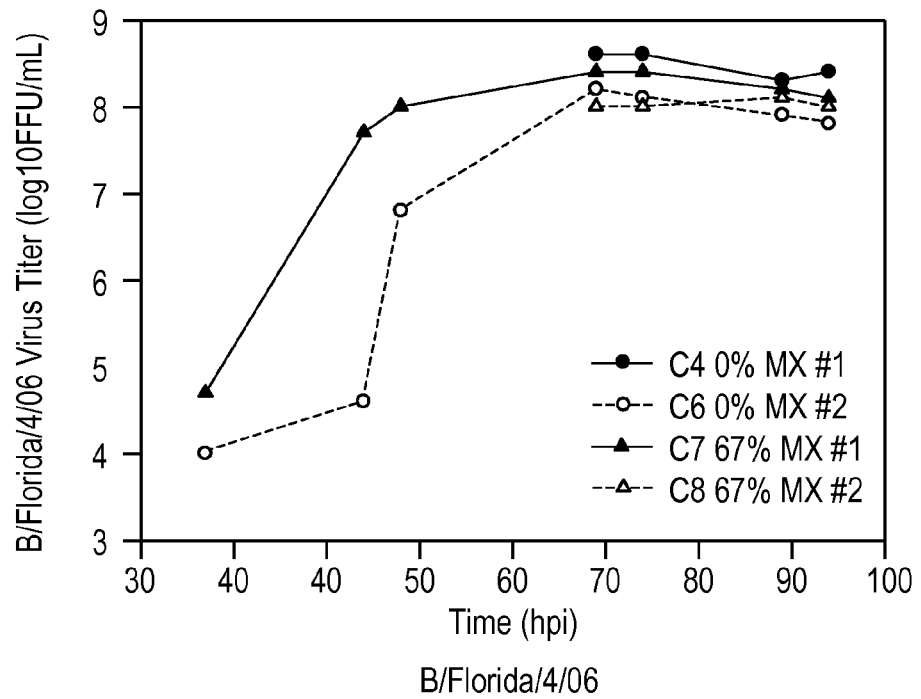
B/Florida/4/06

FIG. 9A
Direct Flow Filtration 1 (DFF1) Filter Rig Drawing
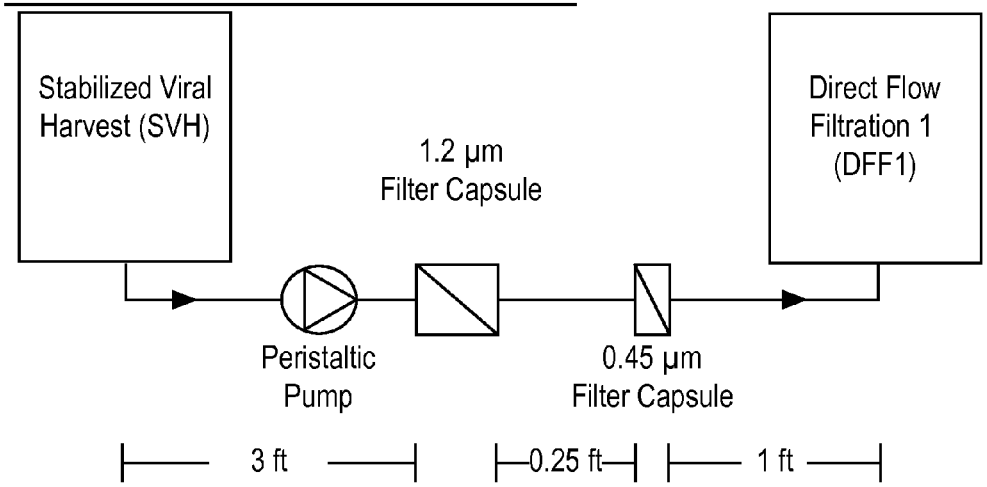
GE Healthcare Uniflux skid Tubing Rigs Drawings
UNIFLUX Sample/Buffer Feed Tubing Rig
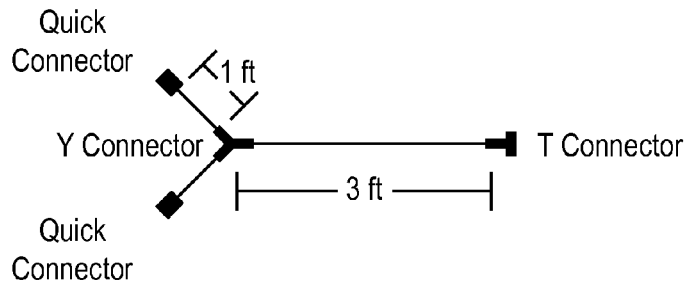
UNIFLUX Feed Drain Tubing Rig
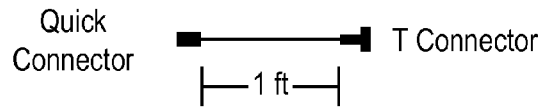
UNIFLUX Permeate Tubing Rig
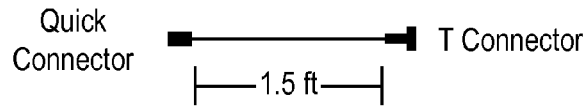
NOTE: All tubing rigs were prepared with 3/8" id silicone tubings.

FIG. 9B
GE Healthcare AKTA Process skid Tubing Rigs Drawings
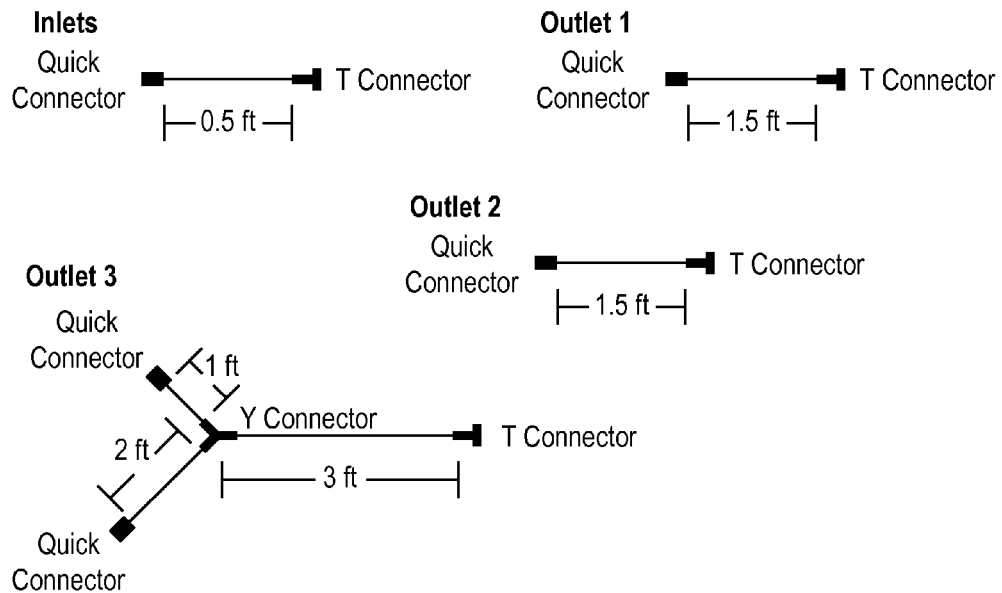
NOTE: All tubing rigs were prepared with 3/8" id silicone tubings.
Direct Flow Filtration 2 (DFF2) Filter Rig Drawing
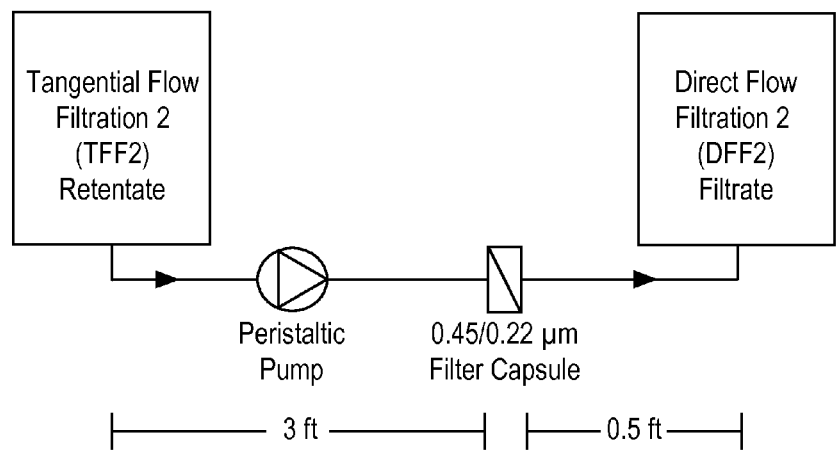

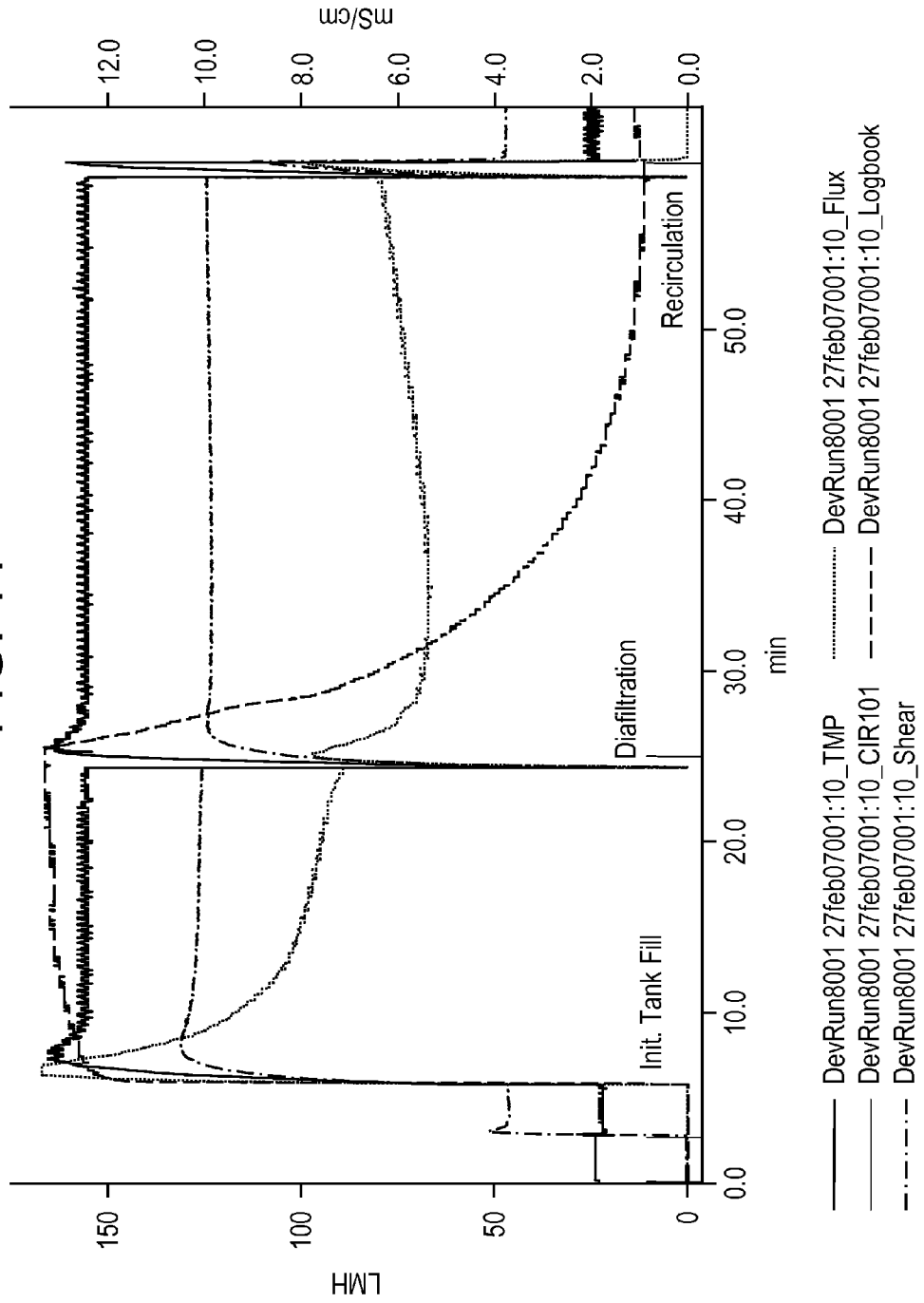

Flux trace of 8XDF

METHODS FOR PURIFICATION OF VIRUSES

2. INTRODUCTION

Cross-Reference to Related Applications

This present application is a national phase patent application of International Patent Application No. PCT/US2009/058174 filed Sep. 24, 2009 and claims benefit of priority from U.S. Provisional Application Ser. Nos. 61/099,749 filed Sep. 24, 2008; 61/104,933 filed Oct. 13, 2008; 61/122,456 filed Dec. 15, 2008; 61/187,721 filed Jun. 17, 2009; and 61/222,131 filed Jul. 1, 2009, the contents of which are entirely incorporated herein by reference.

1. STATEMENT AS TO RIGHTS TO INVENTIONS MADE UNDER FEDERALLY SPONSORED RESEARCH AND DEVELOPMENT

This invention was created in the performance of a Cooperative Research and Development Agreement with the National Institutes of Health, an Agency of the Department of Health and Human Services. The Government of the United States has certain rights in this invention.

3. FIELD OF THE INVENTION

The present invention provides methods for the purification of cell-associated viruses from adherent cells grown in a bioreactor for the development of vaccines.

4. BACKGROUND OF THE INVENTION

Vaccination is the most important public health measure for preventing disease caused by viral infection. The effective use of vaccines is dependent on being able to quickly produce large quantities of vaccine material (e.g., virus) from a stable and easy to cultivate source. The rapid development of vaccines and their abundant availability is critical in combating many human and animal diseases. Delays in producing vaccines and shortfalls in their quantity can cause problems in addressing outbreaks of disease. For example, recent studies suggest that there is cause for concern regarding the long lead times required to produce vaccines against pandemic influenza. See, for example, Wood, J. M., 2001, Philos. Trans. R. Soc. Lond. B. Biol. Sci., 356:1953. Accordingly, recent efforts to produce vaccines have focused on growth of viruses for vaccines in cell culture.

3.1 Influenza Virus

In particular, the use of Madin Darby Canine Kidney (MDCK) cells has been pursued by a number of groups. See, for example, U.S. Pat. No. 6,455,298; U.S. 2005/0118140; U.S. 2005/0118698; U.S. Pat. No. 6,825,306; WO2005/113758; and Radaeva, I. F., et al. Vopr. Virusol. (2005) 50: 43-6. However, many of the existing MDCK cell lines suffer from one or more defects including tumorigenicity, the requirement for animal serum in cell culture, and low yields of influenza viruses suitable for use in vaccines. Furthermore, many of the cell culture processes which have been developed for the production of vaccine material from these cell lines often require numerous manipulations including medium exchange steps and the use of large amounts of virus for inoculation. In addition, because of the continual emergence (or re-emergence) of different influenza strains, new influenza vaccines are generated each season based on the circulating influenza strains. Unfortunately, some influenza vaccine strains are more difficult to grow to high yields. The yield of each batch of cell culture derived material not only defines production capacity but also impacts the cost of manufacturing product thus improving viral yield (i.e., peak viral titer) is desirable.

Recently, novel serum-free medium and non-tumorigenic cell lines that can grow vaccine strains to very high titers and processes for the production of viral material in disposable bioreactors have been developed (see, U.S. 2006/0188977; and U.S. Ser. No. 11/855,769 filed Sep. 14, 2007). The instant invention expands this work and provides novel cell culture medium, highly reproducible efficient scalable processes for the production of large quantities of vaccine material in bioreactors from MDCK cells, in particular, non-tumorigenic cells lines, without the need for medium exchange, and robust downstream purification processes for the production of a highly purified live attenuated vaccine. The methods provided by the present invention are robust requiring minimal manipulation and are cost effective.

3.2 Respiratory Syncitial Virus (RSV)

Human respiratory syncytial virus (RSV) is the leading cause of severe lower respiratory tract infection (LRTI) in infants and young children and is responsible for considerable morbidity and mortality. A total of 18 million people are infected annually in the seven major markets (US, Japan, France, Germany, Italy, Spain, UK), including three million adults and almost 400,000 premature infants. Annually in the U.S. alone, it is estimated that 70,000-125,000 hospitalizations are attributed to RSV LRTI. Two antigenically diverse RSV subgroups A and B are present in human populations. RSV is also recognized as an important agent of infection in immuno-compromised adults and in the elderly. Due to the incomplete resistance to RSV reinfection induced by natural infection, RSV may infect multiple times during childhood and life. The goal of RSV immunoprophylaxis is to induce sufficient resistance to prevent the serious disease which may be associated with RSV infection. The current strategies for developing RSV vaccines principally revolve around the administration of purified viral antigen or the development of live attenuated RSV for intranasal administration. However, to date there have been no approved vaccines or for RSV.

The viral genomic RNA is not infectious as naked RNA. The RNA genome of RSV is tightly encapsidated with the major nucleocapsid (N) protein and is associated with the phosphoprotein (P) and the large (L) polymerase subunit. These proteins form the nucleoprotein core, which is recognized as the minimum unit of infectivity (Brown et al., 1967, J. Virol. 1: 368-373).

Despite decades of research, no commercially available safe and effective RSV vaccine has been developed for the prevention of severe morbidity and mortality associated with RSV infection. A formalin-inactivated virus vaccine has failed to provide protection against RSV infection and in fact lead to exacerbated symptoms during subsequent infection by the wild-type virus in infants (Kapikian et al., 1969, Am. J. Epidemiol. 89:405-21; Chin et al., 1969, Am. J. Epidemiol. 89:449-63). Efforts since have focused on developing live attenuated mutants obtained by recombinant methods, chemical mutagensis and cold passage of the wild type RSV for temperature-sensitive mutants (Gharpure et al., 1969, J. Virol. 3: 414-21; Crowe et al., 1994, Vaccine 12: 691-9). However, purification of live attenuated virus from their cell-associated proteins, which would meet regulatory guidelines for efficacious prophylactic treatment of RSV infection, has proved elusive until now.

Similar to the influenza virus, RSV is grown in a stable cell line wherein the virus is closely associated with the host cell making it difficult to purify the virus from the cell-associated proteins while maintaining a minimum unit of infectivity. Adding to the complexity, RSV is fragile (e.g., shear sensitive). These factors, the virus being predominantly host cell associated and fragile, have made it difficult to purify the virus from host cell extract (e.g., DNA and proteins) while resulting in a clinically acceptable immunogenic composition comprising live attenuated virus. It is for these reasons, in part, why no vaccines are commercially available for RSV. Accordingly, there is a need for a purification process that can be used to purify RSV and other cell-associated viruses for preparation and formulation of immunogenic compositions.

5. SUMMARY OF THE INVENTION

The present invention provides methods for purifying live cell-associated viruses (e.g. RSV) from adherent cells grown in cell culture (e.g., Vero cell culture) that give an overall recovery of viruses of at least 5%, wherein the purified viruses comprise less than 100 ng of host cell DNA (HCD), less than 40 μg of host cell protein (HCP), and less than 0.1 ng of non-specific nuclease per dose (4-6 $\log_{10}$ FFU) of virus.

6. BRIEF DESCRIPTION OF THE FIGURES

FIG. 1 is a plot of the viable cell density (VCD) and cell viability (V %) in 4×2 L bioreactors from day 0 to day 4 of cultivation. The bioreactors were cultured using the Seed Reactor (SR) process conditions detailed in Table 6. 2 dps data for SR 4 is not available.

FIG. 2 shows photographs (taken at 10× magnification) taken at intermediate sampling times between 0 and 40 minutes for 3×2 L seed reactors (SR) for experiment 1, 3 and 4 during B2B trypsinization. Trypsinization performed in bioreactors as per the bead to bead transfer protocol.

FIG. 3 is a plot of the viable cell density (VCD) and cell viability (V %) in 12×2 L final production reactors (FPR). The bioreactors of experiment 3 (FPR3.X.X) were infected on 5 dps (~120 hps) and those of other experiments infected on 4 dps. Post infection VCD and cell viability data for experiment 4 not available.

Figure 6:
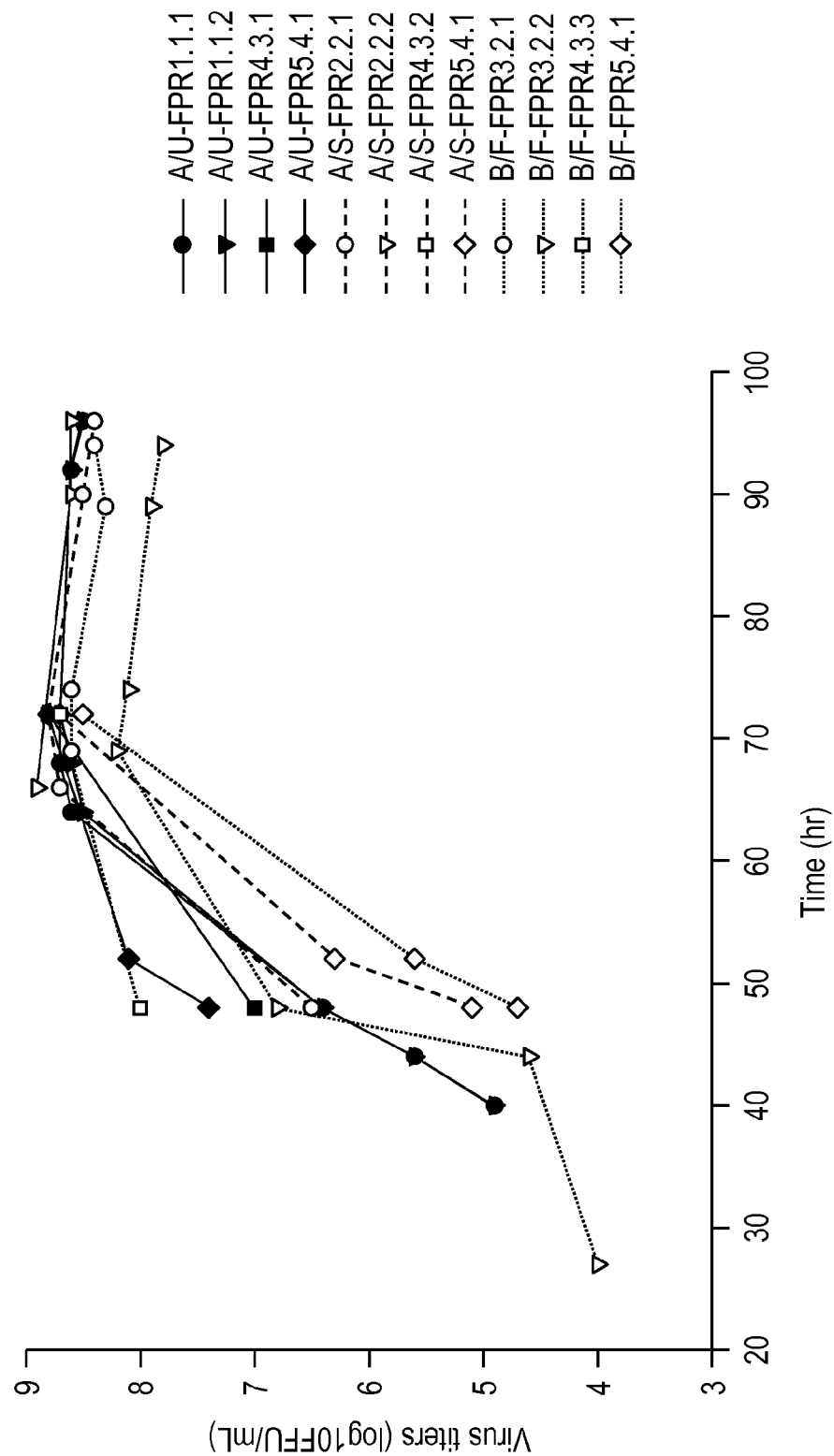

FIG. 6 shows a plot of ca A/Uruguay (A/U), ca A/South Dakota (A/S) and ca B/Florida (B/F) virus titers over time for the cells originally grown in 4×2 L seed reactors and then cultured followed by infecting in 12×2 L final production reactors (FPR) for all experiments. Note: each data point represents the average of three assay replicates. The virus titers below detection limit (<6.4 log 10FFU/mL or <2.4 log 10FFU/mL if diluted) are not recorded.

FIG. 7 shows virus production profiles over time for the strains produced using the 67% medium exchange process (67% MX) versus no medium exchange process (0% MX). Plots for strains ca A/Wisconsin/67/05 and ca A/Uruguay are shown in 7A, plots for ca A/South Dakota and ca B/Florida are shown in 7B.

Figure 8:
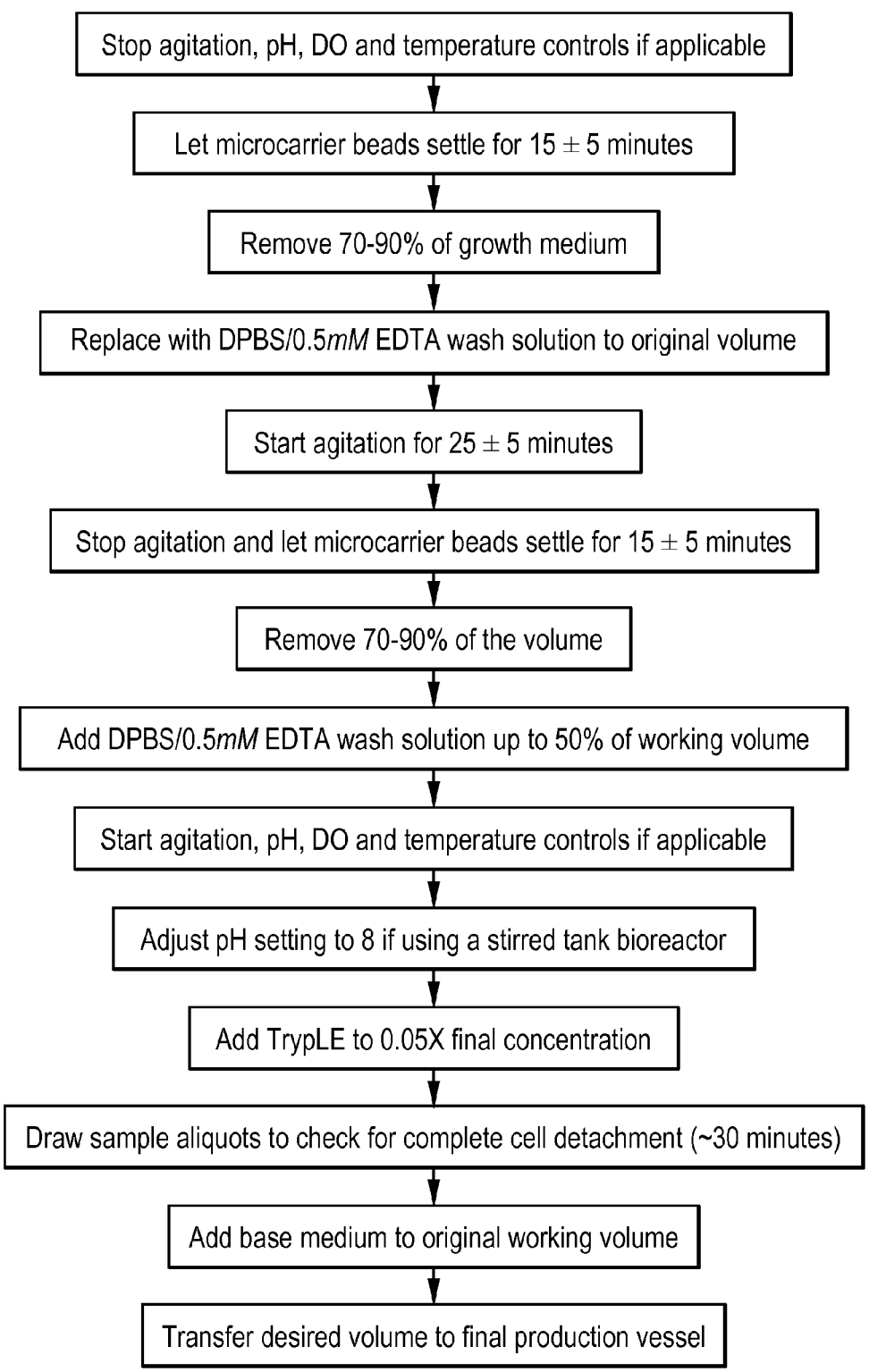

FIG. 8 presents a flow chart of a bead to bead transfer process utilizing two wash steps each utilizing a buffered salt solution (DPBS) comprising a chelating agent (EDTA) and a protease (TrypLE™) at a final concentration of just 0.05× that effects cell detachment within ~30 minutes.

FIG. 9 presents drawings of the filter and tubing rigs used for the Direct Flow Filtration (DFF1) filter rig (Panel A, top), the GE Healthcare Uniflux skid tubing rigs (Panel A, bottom), the GE Healthcare AKTA process skid tubing rigs (Panel B, top), and the Direct Flow Filtration 2 (DIFF2) filter rig (Panel B, bottom).

Figure 10A:
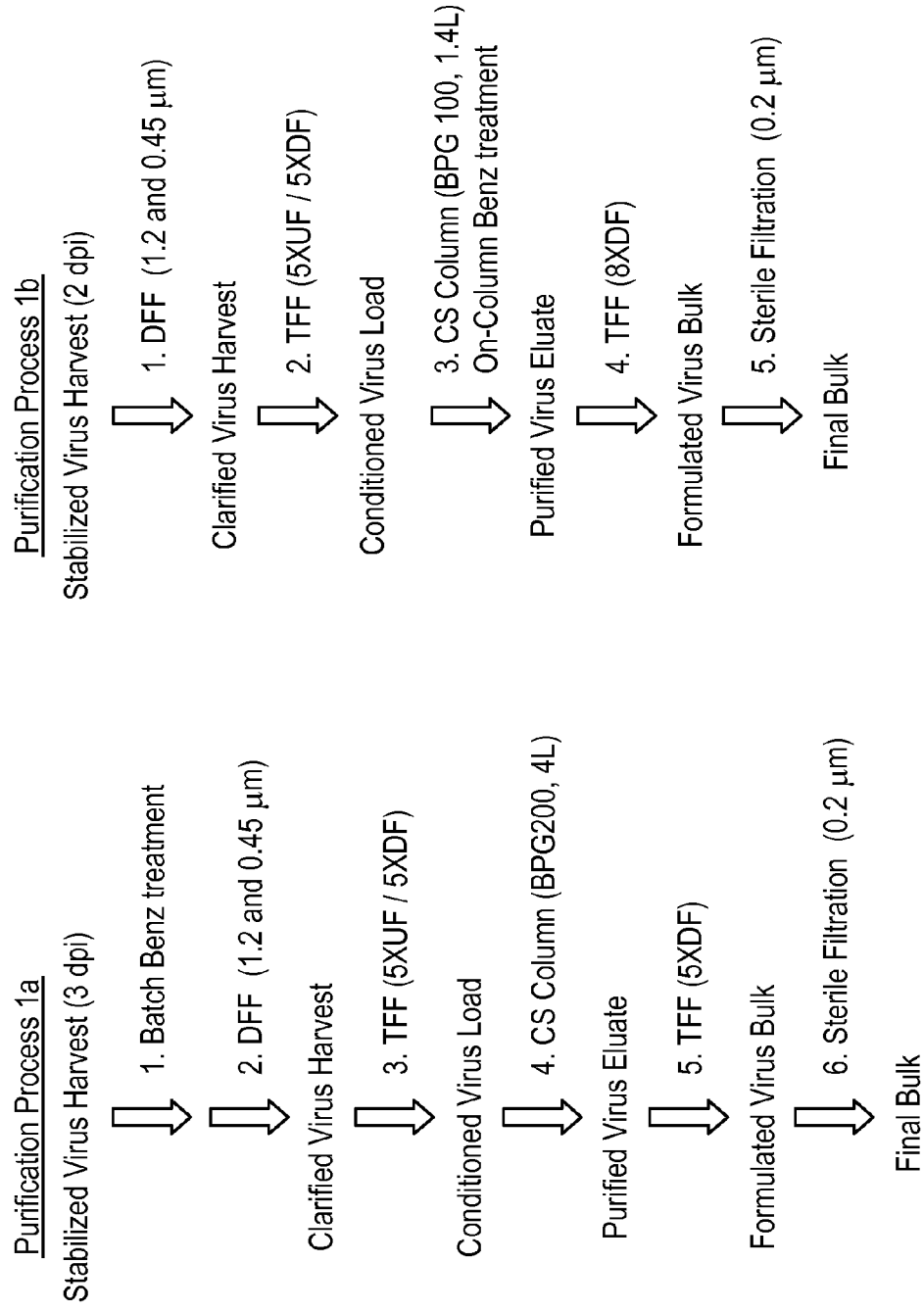

FIG. 10 presents the scheme of the initial purification process 1a in parallel with the improved purification process 1b in panel A. Additional modifications are detailed in the scheme presented in panel B. The details of each process are provided in Examples 3 and 4.

FIG. 11 presents the flux trace curve of TFF1 run #8.

Figure 12:
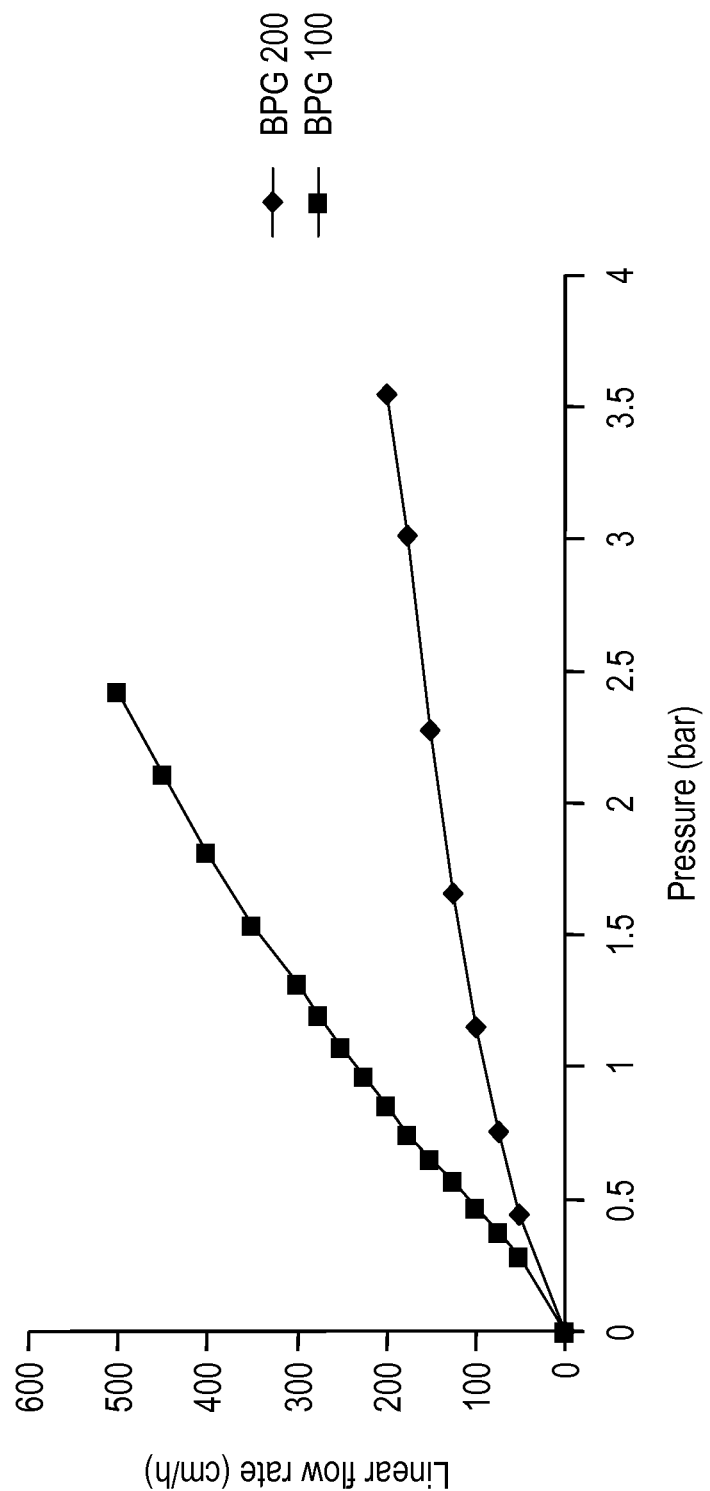

FIG. 12 presents the BPG 100 and BPG 200 CS column pressure flow characteristics.

Figure 13:
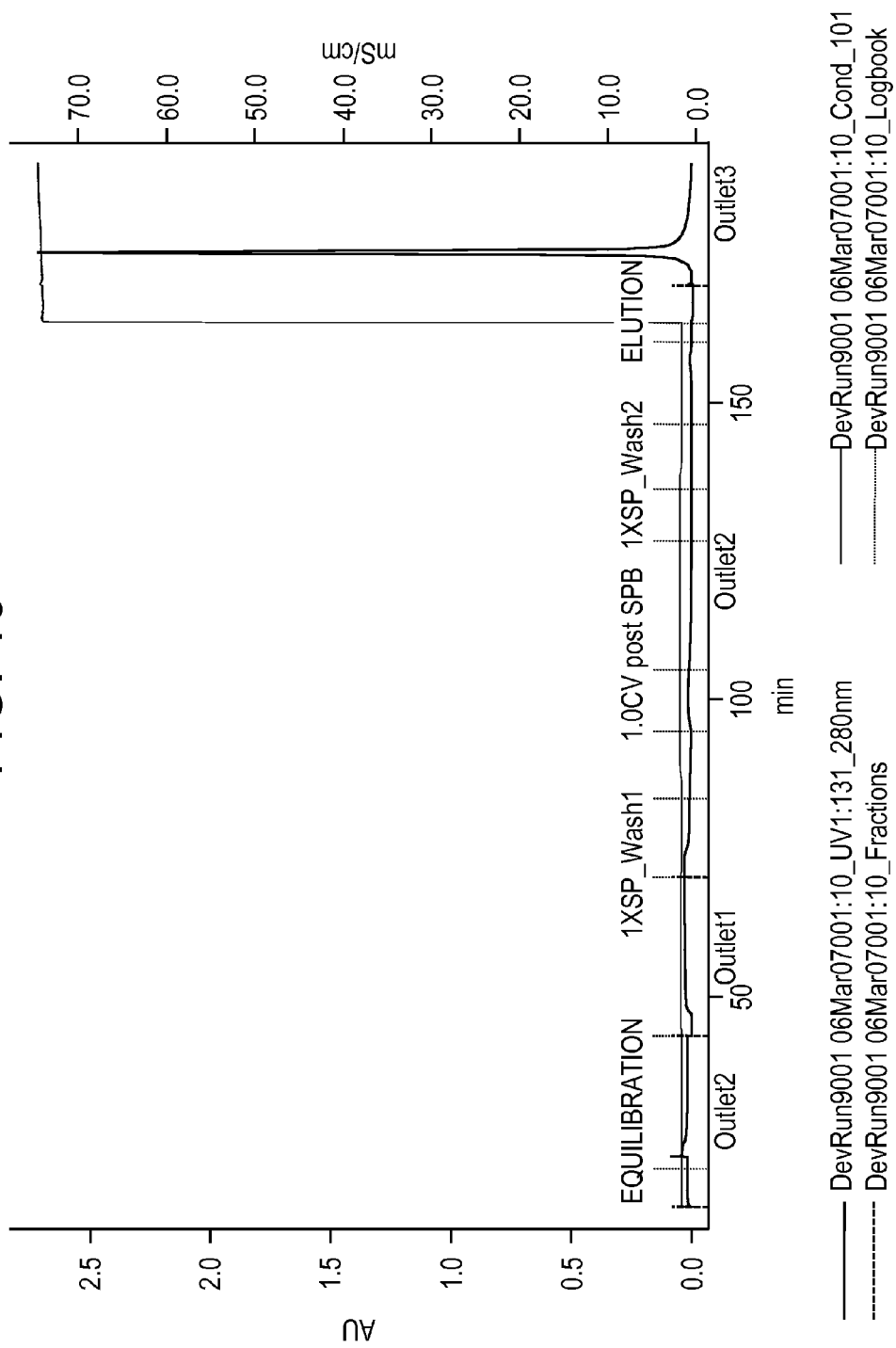

FIG. 13 presents the CS column elution chromatogram of run #9.

Figure 14:
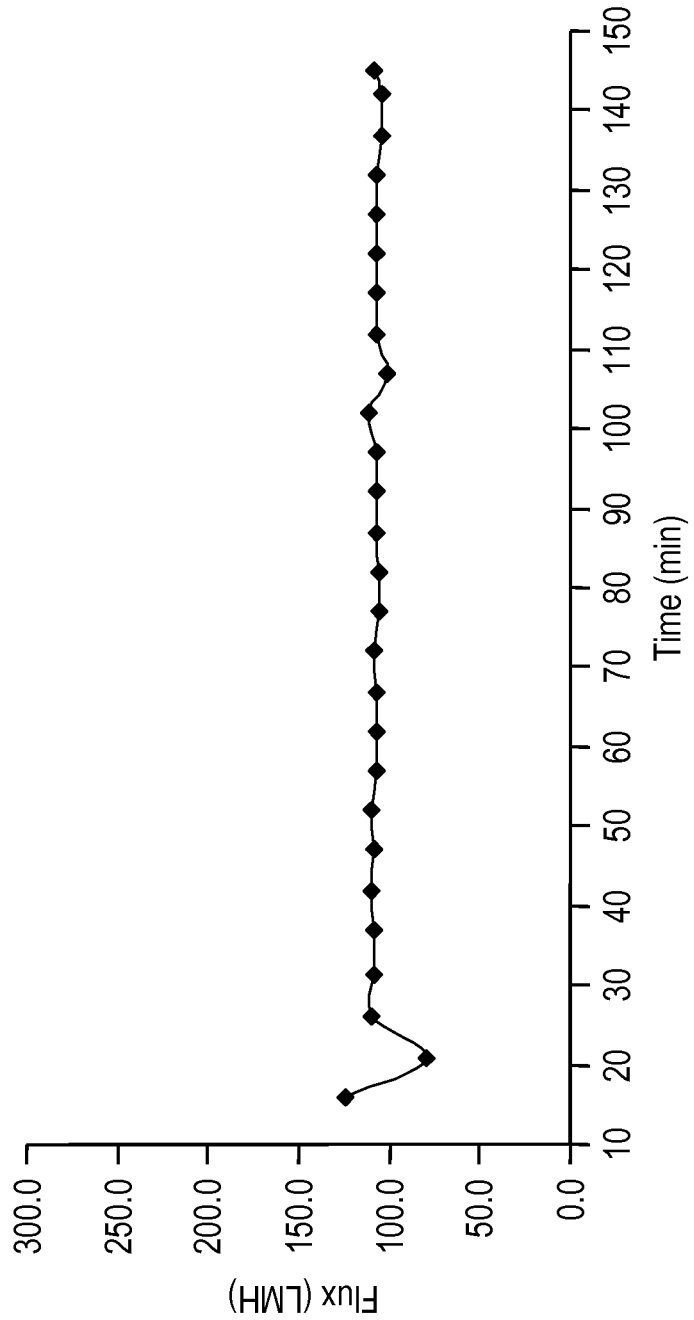

FIG. 14 presents the flux trace curve of run #8 TFF2 8XDF process.

Figure 15:
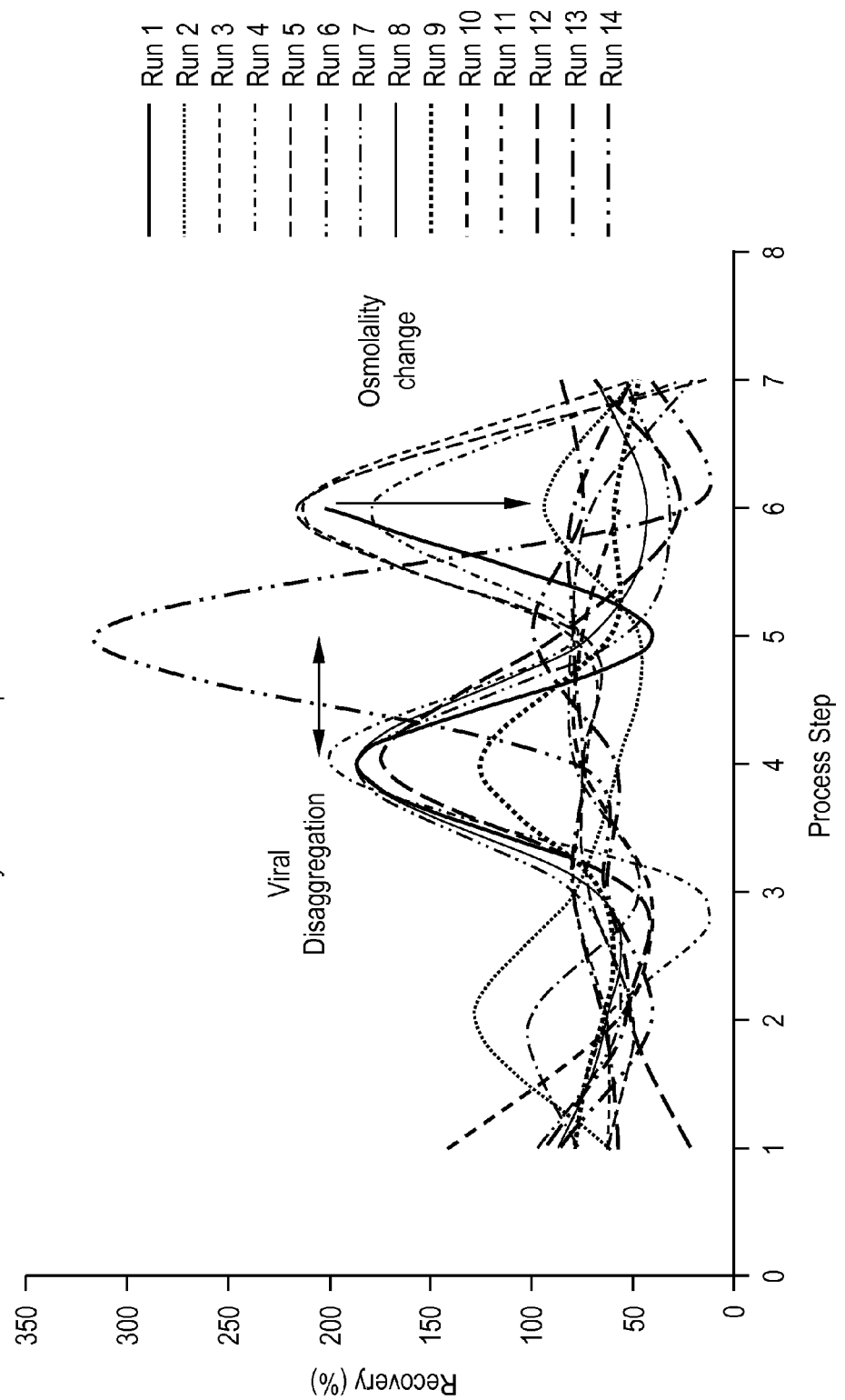
Figure 16:
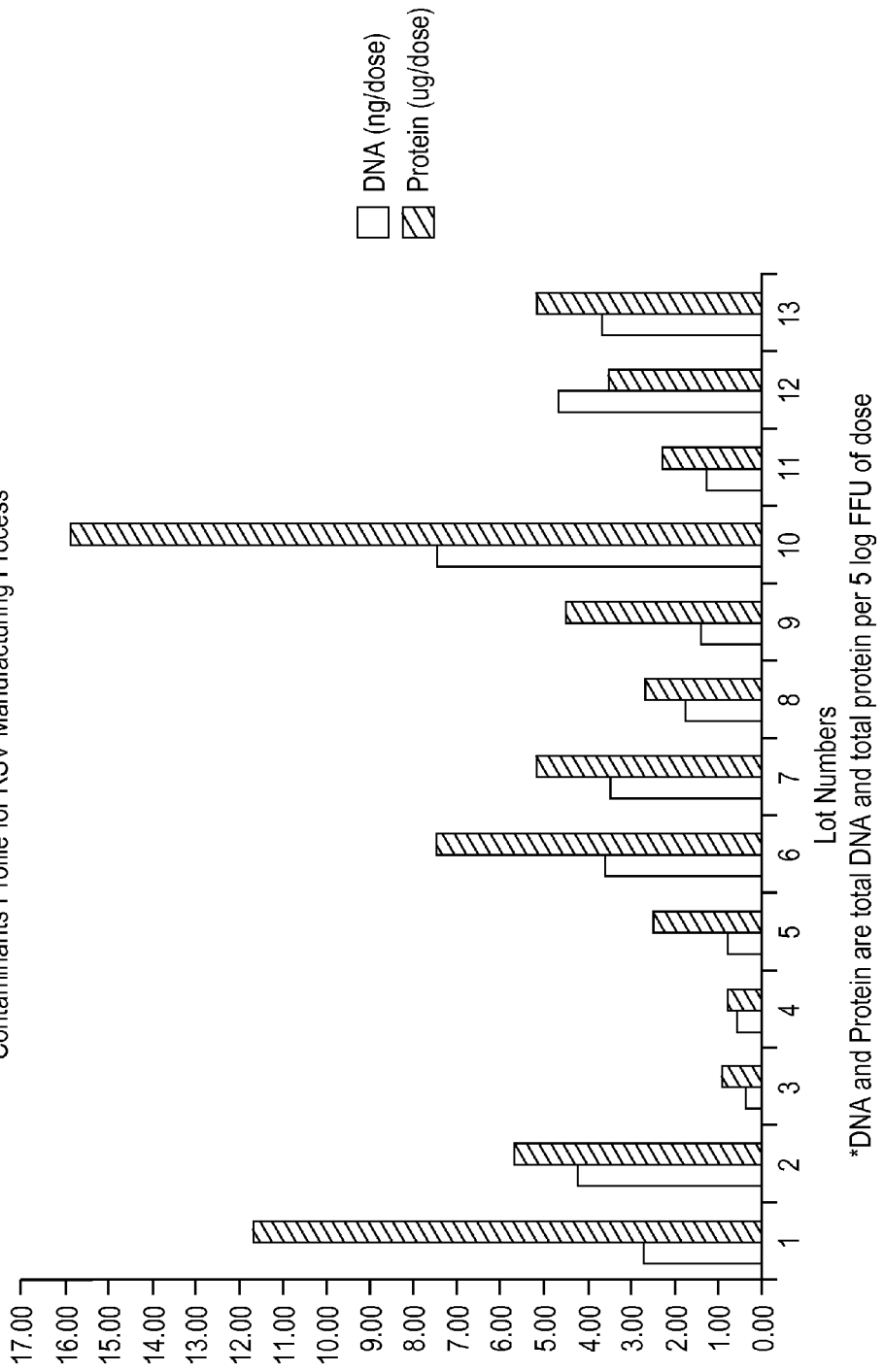
Figure 17:
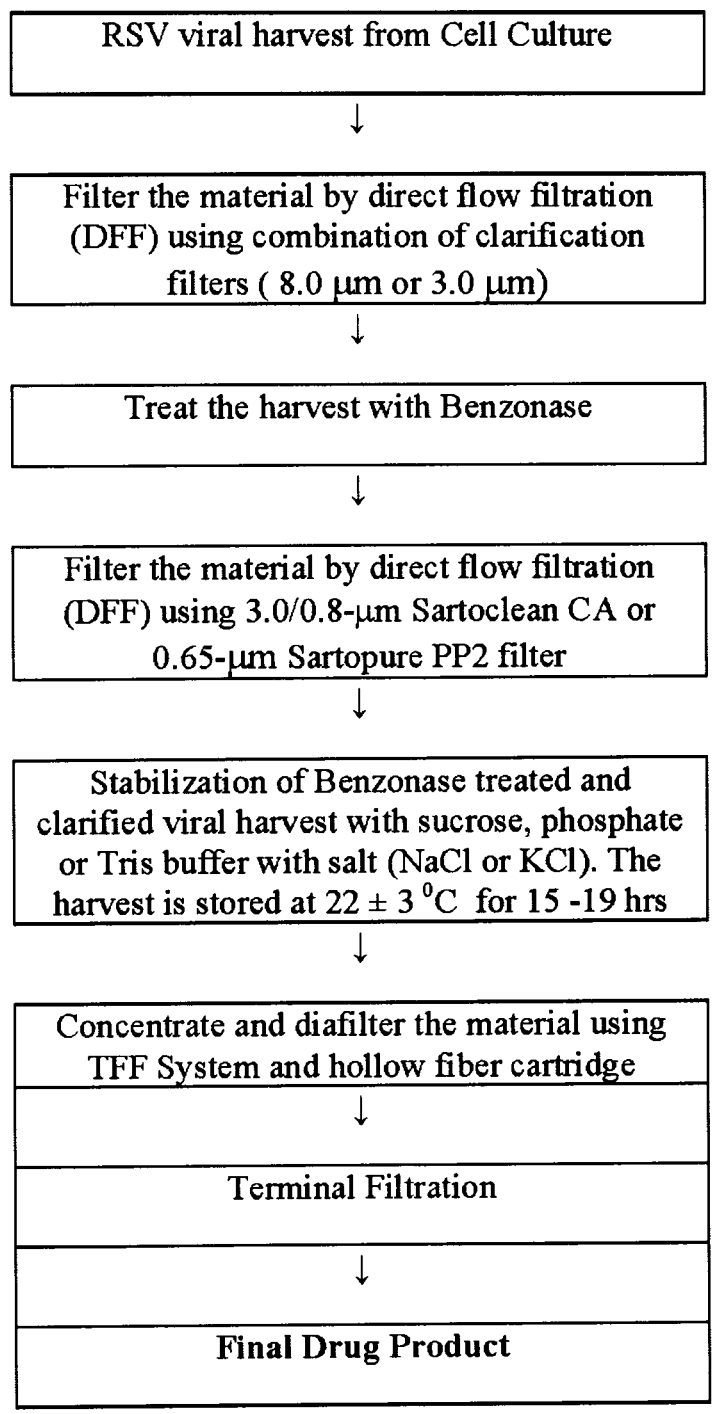

FIG. 15 presents the summary of process step titer recoveries for different production lots of RSV at 10 and 30-L scale FIG. 16 presents the summary of the total DNA and total protein per 5 Log FFU of RSV dose (final purified drug product) among the different production lots of RSV FIG. 17 presents Diagram 1: Downstream manufacturing process for production of RSV at 10 and 30-L scale.

7. DETAILED DESCRIPTION

The present invention provides highly reproducible efficient scalable processes for the production of large quantities of virus (e.g., influenza virus or RSV) or viral antigen for prophylactic, diagnostic, immunotherapeutic or therapeutic use in bioreactors from adherent cells (e.g. MDCK cells, in particular, non-tumorigenic cell lines or Vero cells). In particular, the present invention provides robust methods for the production of cold-adapted, and/or temperature sensitive, and/or attenuated influenza or respiratory syncitial viruses, to high titer that do not require any medium exchange.

In addition, the present invention provides culture medium that support the cultivation of MDCK cells (e.g., non-tumorigenic MDCK cells) and support the replication of virus including, but not limited to influenza virus (e.g., cold-adapted, and/or temperature sensitive, and/or attenuated influenza viruses) to high titer without the need for any medium exchange.

In addition, the present invention also provides methods of preparing vaccine material (e.g., influenza virus) from MDCK cells (e.g., non-tumorigenic MDCK cells), and methods of preventing influenza infection utilizing vaccine materials produced in MDCK cells. Any cell-associated virus (e.g. influenza and RSV) may be purified by a process described herein and/or contained in an immunogenic composition described herein. As used herein, "a cell-associated virus" refers to a virus in which approximately 60% or more of the titer of the virus is found associated with virus-infected adherent cells as determined by any technique known to one of skill in the art. The methods of the invention are particularly useful for the production of cold adapted/temperature sensitive/attenuated (ca/ts/att) influenza strains (e.g., those in FluMist) and RSV (e.g., rA2cp248/404/1030ΔSH).

Viruses that can be grown in non-tumorigenic MDCK cells and/or Vero cells include but are not limited to negative strand RNA viruses, including but not limited to influenza, RSV, parainfluenza viruses 1, 2 and 3, and human metapneumovirus, as well as other viruses, including DNA viruses, retroviruses, positive strand RNA viruses, negative strand RNA viruses, double-stranded RNA viruses, including, but not limited to, papovavirus, vesicular stomatitis virus, vaccinia virus, Coxsackie virus, reovirus, parvovirus, adenovirus, poliomyeltitis virus, measles virus, rabies virus, and herpes virus.

7.1 DEFINITIONS

Tumorigenicity, as used herein, has the ordinary meaning attributed to this term by one skilled in the art. Tumorigenicity is, in one embodiment, determined by the adult nude mouse model (e.g., Stiles et al., 1976, Cancer Res, 36:1353, and Example 5 below). Tumorigenicity may also be tested by other assays, for example, by injection into a chick embryo and/or topical application to the chorioallantois (Leighton et al., 1970, Cancer, 26:1024).

The term "recombinant" indicates that the material (e.g., a nucleic acid or protein) has been artificially or synthetically (non-naturally) altered by human intervention. The alteration can be performed on the material within, or removed from, its natural environment or state. Specifically, when referring to a virus, e.g., an influenza virus, the virus is recombinant when it is produced by the expression of a recombinant nucleic acid. A recombinant virus may further incorporate one or more mutations introduced into the genome. A recombinant virus may also be a reassortant virus when it comprises components derived from more than one parental viral strain.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuraminidase, from a second parental virus. A 6:2 reassortant includes 6 genomic segments, most commonly the 6 internal genes from a first parental virus, and two complementary segments, e.g., hemagglutinin and neuraminidase, from a different parental virus.

The term "about," as used herein, unless otherwise indicated, refers to a value that is no more than 10% above or below the value being modified by the term. For example, the term "about 5 µg/kg" means a range of from 4.5 µg/kg to 5.5 µg/kg. As another example, "about 1 hour" means a range of from 54 minutes to 66 minutes.

The terms "temperature sensitive", "cold adapted" and "attenuated" are well known in the art. For example, the term "temperature sensitive" ("ts") indicates that the virus exhibits a 100 fold or greater reduction in titer at a higher temperature, e.g., 39° C. relative to a lower temperature, e.g., 33° C. for influenza A strains, and that the virus exhibits a 100 fold or greater reduction in titer at a higher temperature, e.g., 37° C. relative to a lower temperature, e.g., 33° C. for influenza B strains. For example, the term "cold adapted" ("ca") indicates that the virus exhibits a higher growth rate at a lower temperature, e.g., 25° C. within 100 fold of its growth at a higher temperature, e.g., 33° C. For example, the term "attenuated" ("att") indicates that the virus replicates in the upper airways of ferrets but is not detectable in lung tissues, and does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, are also useful viruses encompassed by the invention. Growth indicates viral quantity as indicated by titer, plaque size or morphology, particle density or other measures known to those of skill in the art.

7.2 CELLS

The cell-associated viruses described herein can be propagated in any adherent cells that allow the viruses to grow to titers that permit harvest, recovery and use of the viruses. In one embodiment, the adherent cells allow the cell-associated viruses to grow to titers comparable to those determined for the corresponding wild-type viruses. In a specific embodiment, the cell-associated viruses described herein are propagated in cells that are susceptible to infection by the viruses.

In one embodiment, the cell-associated viruses described herein are propagated in mammalian cells. Representative mammalian cells that the cell-associated viruses described herein can be propagated in include, but are not limited to, Vero cells, CHO cells, Hep-2 cells, MBCK cells, MDCK cells, MRC-5 cells, HeLa cells and LLC-MK2 cells. In a specific embodiment, the cell-associated viruses described herein, including respiratory syncytial viruses, are propagated in Vero cells. In another specific embodiment, the cell-associated viruses, including influenza virus, are propagated in MDCK cells.

6.2.1 MDCK Cells

MDCK cells are known to support the isolation and replication of numerous viruses including but not limited to various viruses including but not limited to orthomyxoviruses, paramyxoviruses, rhabdoviruses and flaviviruses. In particular, MDCK cells are widely used for the production influenza viruses. However, as noted above, some MDCK cell lines are tumorigenic. If tumorigenicity is of regulatory concern the present invention provides methods to proliferate non-tumorigenic MDCK cells and use the same for the production of influenza viruses. Accordingly, in one embodiment, the methods of the invention utilize non-tumorigenic MDCK cells. In another embodiment, the method of the invention utilize MDCK cells regardless of tumorigenicity.

Non-tumorigenic MDCK cell lines which may be utilized in the methods of the invention include but are not limited to, those which have been deposited with the American Type Culture Collection (10801 University Boulevard, Manassas, Va. 20110-2209) on deposited Jan. 5, 2005 and assigned ATCC Deposit Nos. PTA-6500 and PTA-6503 (designated MDCK-S and MDCK-SF103, respectively); those deposited on Oct. 5, 2006 and assigned ATCC Deposit Nos. PTA-7909 and PTA-7910, (designated subclones 1-A and 1-B, respectively).

Other MDCK cells which may be utilized include, but are not limited to, those which have been deposited with the American Type Culture Collection and assigned ATCC Deposit Nos. PTA-6501 and PTA-6502 (designated MDCK-SF101 and MDCK-SF102, respectively); those assigned ATCC Deposit No. CRL-12042 (designated MDCK.5F1); those assigned ATCC Deposit Nos. ATCC CCL34; CRL-2286; and CRL-2285.

In a specific embodiment, the non-tumorigenic MDCK cells used in the methods of the invention are non-tumorigenic in the adult nude mouse model (see, Stiles et al.). In another specific embodiment, the non-tumorigenic MDCK cells used in the methods of the invention are non-tumorigenic when injected into a chick embryo and/or topically applied to the chorioallantois (see, Leighton et al., Id). In still another embodiment, the non-tumorigenic MDCK cells used in the methods of the invention are non-tumorigenic in the adult nude mouse model but not when injected into a chick embryo and/or topically applied to the chorioallantois. In yet another embodiment, the non-tumorigenic MDCK cells used in the methods of the invention are non-tumorigenic in the adult nude mouse model and when injected into a chick embryo and/or topically applied to the chorioallantois. In still another embodiment, the non-tumorigenic MDCK cells used in the methods of the invention are non-tumorigenic after at least 20 passages, or after at least 30 passages, or after at least 40 passages, or after at least 50 passages, or after at least 60 passages, or after at least 70 passages, or after at least 80 passages, or after at least 90 passages, or after at least 100 passages. In still other embodiments, non-tumorigenic MDCK cells used in the methods of the invention are non-tumorigenic after at least 20 passages, or after at least 30 passages, or after at least 40 passages, or after at least 50 passages, or after at least 60 passages, or after at least 70 passages, or after at least 80 passages, or after at least 90 passages, or after at least 100 passages in a serum-free medium of the invention (e.g., MediV SFM 105+TE, MediV SFM 109, and MediV SFM 110).

Tumorigenicity may be quantified in numerous ways known to one of skill in the art. One method commonly utilized is to determine the "$TD_{50}$" value which is defined as the number of cells required to induce tumors in 50% of the animals tested (see, e.g., Hill R. The $TD_{50}$ assay for tumor cells. In: Potten C, Hendry J, editors. Cell clones. London: Churchill Livingstone; 1985. p. 223). In one embodiment, the non-tumorigenic MDCK cells used in the methods of the invention have a $TD_{50}$ value of between about $10^{10}$ to about $10^1$, or between about $10^8$ to about $10^3$, or between about $10^7$ to about $10^4$. In a specific embodiment, the non-tumorigenic MDCK cells used in the methods of the invention have a $TD_{50}$ value of more than about $10^{10}$, or of more than about $10^9$, or of more than about $10^8$, or of more than about $10^7$, or of more than about $10^6$, or of more than about $10^5$, or of more than about $10^4$, or of more than about $10^3$, or of more than about $10^2$, or of more than about $10^1$. In a specific embodiment, the non-tumorigenic MDCK cells used in the methods of the invention have a $TD_{50}$ value of $10^7$ or more.

It is further contemplated that the non-tumorigenic MDCK cells used in the method of the invention are also non-oncogenic. Methods for determining if cells are oncogenic generally involve the inoculation of cell lysates and/or DNA into newborn rodent species and evaluation of any tumor formation over time (see, for example, Nowinski and Hays, 1978, J. Virol., 27: 13-8; Peeper, et al., 2002, Nat Cell Biol., 4:148-53; Code of Federal Regulation (CFR), "Oncogenicity", Title 40, Vol. 8, Chapter 1, section 798.330, pp. 160-164). For example, cell lysates and/or DNA from at least $10^7$ cell equivalents are injected into newborn rodents (e.g., hamster, nude mice, rats) typically less then 4 days old which are then monitored for up to five months or more. Oncogenicity assays are routinely performed by commercial testing companies (e.g., BioReliance, see Protocols #001031 and #001030). In one embodiment, cell lysates and/or DNA from at least $10^5$, or at least $10^6$, or at least $10^7$ non-tumorigenic MDCK cells used in the methods of the invention do not induce tumor formation in 2 months, or in 3 months, or in 4 month, or in 5 months, or in 6 months, or longer, when injected into a newborn rodent species. In another embodiment, 0.01 mg, or 0.02 mg, or 0.03 mg, or 0.04 mg, or 0.05 mg, or 0.06 mg, or 0.07 mg, or 0.08 mg, or 0.09 mg, or 0.10 mg, or more, DNA from the non-tumorigenic MDCK cells used in the methods of the invention do not induce tumor formation in 2 months, or in 3 months, or in 4 month, or in 5 months, or in 6 months, or longer, when injected into a newborn rodent species.

It is contemplated that the MDCK cells (e.g., non-tumorigenic MDCK cells) used in the methods of the invention support the replication of viruses including but not limited to orthomyxoviruses (including influenza A and/or B strains), paramyxoviruses (including RSV A and/or B, human metapneumovirus and parainfluenza 1, 2 and/or 3), rhabdoviruses and flavoviruses.

In a specific embodiment, the MDCK cells (e.g., non-tumorigenic MDCK cells) used in the methods of the invention support the replication of cold adapted temperature sensitive, attenuated influenza viruses such as those found, for example, in FluMist® (Belshe et al., 1998, *N Engl J Med* 338:1405; Nichol et al., 1999, *JAMA* 282:137; Jackson et al., 1999, *Vaccine*, 17:1905) and/or reassortant viruses comprising the backbone (e.g., the remaining gene segments) of these viruses or comprising the backbone (or one or more vRNA segment(s)) of influenza viruses having one or more of the following characteristics: cold adapted, attenuated, and temperature sensitive.

One indication of the ability of a cell to support viral replication is the yield of infectious virus obtained from an infected cell culture. Viral yield can be determined by numerous assays designed to measure viral infection and/or growth. For example, viral yield can be quantified by determining the concentration of virus present in a sample according to a median tissue culture infectious dose ($TCID_{50}$) assay that measures infectious virions, a fluorescent focus assay (FFA) that detect virus antigens within infected cells in a cell culture monolayer (see for example, U.S. Pat. No. 7,262,045). $TCID_{50}$ values are often reported as the $\log_{10} TCID_{50}$/mL and the FFA values are often reported as $\log_{10}$ FFU/mL (fluorescent focus units/mL). Methods useful for the production of influenza viruses include, but are not limited to, those disclosed in Patent Publication WO 08/105,931 (see in particular Example 12).

In a specific embodiment, the MDCK cells (e.g., non-tumorigenic MDCK cells) used in the methods of the invention support the replication of influenza viruses ((e.g., ca/ts strains) to a $\log_{10} TCID_{50}$/mL and/or a $\log_{10}$ FFU/mL of at least about 7.6, at least about 7.8, at least about 8.0, at least about 8.2, at least about 8.4, at least about 8.6, at least about 8.8, at least about 9.0, at least about 9.2, at least about 9.4, at least about 9.6, at least about 9.8, at least about 10.0. In another specific embodiment, the MDCK cells used in the methods of the invention support the replication of influenza viruses ((e.g., ca/ts strains) to a $\log_{10} TCID_{50}$/mL and/or a $\log_{10}$ FFU/mL of at least about 7.6, at least 7.8, at least 8.0, at least 8.2, at least 8.4, at least 8.6, at least 8.8, at least 9.0, at least 9.2, at least 9.4, at least 9.6, at least 9.8, at least 10.0. In certain specific embodiments, the MDCK cells used in the methods of the invention are non-tumorigenic.

The wild-type influenza viruses used in preparation of the vaccine strains for annual vaccination against epidemic influenza are recommended annually by the Vaccines and Related Biological Products Advisory Committee to the Centers for Biologics Evaluation and Research (CBER) or the World Health Organization (WHO) and the European Medicines Evaluation Agency (EMEA), and are provided to manufacturers by the FDA or the Centers for Disease Control and Prevention (CDC). These strains may then used for the production of reassortant vaccine strains which generally combine the NA and/or HA genes of the wild-type viruses with the remaining gene segments derived from a donor virus (often referred to as a master donor virus or MDV) which will have certain desirable characteristics. For example, an MDV strain may be cold-adapted, and/or temperature sensitive, and/or attenuated, and/or have a high growth rate. The embodiments that follow immediately below relate to cold-adapted, and/or temperature sensitive, and/or attenuated versions of different influenza strains (e.g., wild type strains recommended by one or more health organization). Such cold-adapted, and/or temperature sensitive, and/or attenuated influenza viruses can be made by obtaining recombinant and/or reassortant influenza viruses that comprise the HA and NA gene segments from the strain of interest and the remaining gene segments from a suitable cold-adapted, and/or temperature sensitive, and/or attenuated influenza strain (also referred to herein as a "cold-adapted, temperature sensitive, attenuated backbone") such as, for example, the cold-adapted, temperature sensitive, attenuated influenza viruses found in FluMist® (ca A/Ann Arbor/6/60 and ca B/Ann Arbor/1/66). As used herein a recombinant and/or reassortant virus that comprises HA and NA gene segments from a wild type influenza virus strain and the remaining gene segments from a virus that is cold-adapted and/or temperature sensitive and/or attenuated influenza. Reassortant and/or recombinant virus are also referred to by the wild type strain designation preceded by one or more of the identifiers "ca", "att", "ts", for example a recombinant and/or reassortant virus that comprises HA and NA gene segments from A/New Calcdonia/20/99 and the remaining segments from a cold-adapted, temperature sensitive, attenuated influenza virus (e.g., A/Ann Arbor/6/60) may be designated simply "Ca A/New Calcdonia/20/99."

In certain embodiments, the MDCK cells (e.g., non-tumorigenic MDCK cells) used in the methods of the invention support the replication of a cold-adapted, and/or temperature sensitive, and/or attenuated version (e.g., reassortant) of at least one influenza strain (e.g., an influenza A strain, an influenza B strain) recommended and/or provided annually by one or more health organization including, but not limited to, the CBER, the WHO, the EMEA, the FDA and the CDC, to a $\log_{10}$ TCID$_{50}$/mL and/or a $\log_{10}$ FFU/mL of at least about 7.6, at least about 7.8, at least about 8.0, at least about 8.2, at least about 8.4, at least about 8.6, at least about 8.8, at least about 9.0, at least about 9.2, at least about 9.4, at least about 9.6, at least about 9.8, at least about 10.0. In another specific embodiment, the MDCK cells (e.g., non-tumorigenic MDCK cells) used in the methods of the invention support the replication of a cold-adapted, and/or temperature sensitive, and/or attenuated version (e.g., reassortant) of at least one influenza strain (e.g., an influenza A strain, an influenza B strain) recommended and/or provided annually by one or more health organization including, but not limited to, the CBER, the WHO, the EMEA, the FDA and the CDC, to a $\log_{10}$ TCID$_{50}$/mL and/or a $\log_{10}$ FFU/mL of at least about 7.6, at least 7.8, at least 8.0, at least 8.2, at least 8.4, at least 8.6, at least 8.8, at least 9.0, at least 9.2, at least 9.4, at least 9.6, at least 9.8, at least 10.0. In certain specific embodiments, the MDCK cells used in the methods of the invention are non-tumorigenic.

In certain other embodiments, the MDCK cells (e.g., non-tumorigenic MDCK cells) used in the methods of the invention support the replication of a cold-adapted, and/or temperature sensitive, and/or attenuated version of at least one influenza A strain. It is contemplated that the influenza A strain may be of any subtype (e.g., $H_1N_1$, $H_3N_2$, $H_7N_7$, $H_5N_1$, $H_9N_2$, $H_1N_2$, $H_2N_2$). Presently at least 16 different HA and 9 different NA subtypes have been identified in influenza A viruses. Accordingly, the influenza A strain may comprise any combination of HA and NA subtypes currently known or identified in the future and/or may be a reassortant. In certain specific embodiments, the MDCK cells used in the methods of the invention are non-tumorigenic.

In certain other embodiments, the MDCK cells (e.g., non-tumorigenic MDCK cells) used in the methods of the invention support the replication of a cold-adapted, and/or temperature sensitive, and/or attenuated version of at least one influenza B strain. Influenza B viruses are not currently divided into subtypes based upon their hemagglutinin and neuraminidase proteins; rather they are classified by lineage. Presently, influenza B virus strains are divided into two lineages, the B/Yamagata and the B/Victoria lineages of which there are numerous sublineages. Accordingly, the influenza B strain may be derived from any lineage and/or sublineage currently known or identified in the future and/or may be a reassortant. In certain specific embodiments, the MDCK cells used in the methods of the invention are non-tumorigenic.

6.3 Cell Culture Medium and Methods

The present invention provides serum-free cell culture medium and highly reproducible efficient scalable processes for the production of large quantities of vaccine material in bioreactors, including single use bioreactors, standard reusable bioreactors (e.g., stainless steel and glass vessel bioreactors). In particular, the present invention provides methods for the replication of influenza viruses (e.g., cold-adapted, and/or temperature sensitive, and/or attenuated) to high titer, e.g., a $\log_{10}$ TCID$_{50}$/mL and/or a $\log_{10}$ FFU/mL of at least about 7.4, or at least about 7.6, or at least about 7.8, or at least about 8.0, or at least about 9.0, or at least about 10.0. In one aspect, the present invention provides an enriched serum-free cell culture medium that supports proliferation of MDCK cells (e.g., non-tumorigenic MDCK cells) to a high cell density and eliminates the need for a medium exchange step to obtain high viral titers. The elimination of a medium exchange step offers several advantages such as decrease in process time and usage of medium. Moreover, it reduces the number of operations required during manufacturing, which in turn decreases the chances of contamination. In another aspect, the present invention provides improved methods for the propagation of non-tumorigenic cells on microcarriers including bead to bead transfers methods. In another aspect, the enriched serum-free cell culture medium of the invention maintains the non-tumorigenic characteristics of non-tumorigenic MDCK cells.

6.3.1 Enriched Serum-Free Medium

It will be appreciated by one of skill in the art that the cell culture medium used to proliferate cells can impact one or more cell characteristics including but not limited to, being non-tumorigenic, being non-oncogenic, growing as adherent cells, growing as non-adherent cells, having an epithelial-like morphology, supporting the replication of various viruses when cultured, and supporting the replication of influenza virus to high titer as described herein. To reduce the risk of contamination by adventitious agents (e.g., mycoplasma, viruses, and prions) The use of serum or animal extracts in tissue culture applications for the production of therapeutic (e.g. vaccine) material should be minimized, or even eliminated. Furthermore, minimizing the number of manipulations required during a cell culture process can significantly decrease the chances of contamination. Accordingly, the present invention provides enriched serum-free culture medium useful for the proliferation of MDCK cells (e.g., non-tumorigenic MDCK cells) and production of vaccine material using batch culture methods. In particular the enriched serum-free culture medium of the invention (also referred to herein as "serum-free medium of the invention" and "medium of the invention") may be used in batch culture methods that do not utilize medium exchange, or supplementation. Accordingly, the development and use of the serum-free medium of the invention overcome one of the most challenging operational problems in cell culture-based production of vaccine material (e.g., influenza virus), the requirement for medium exchange/supplementation.

In one embodiment, serum-free medium of the invention support the proliferation of non-tumorigenic MDCK cells, wherein the cells remain non-tumorigenic after proliferation in the medium (i.e., after being passaged). In a specific embodiment, the MDCK cells are non-tumorigenic after at least 20 passages, or after at least 30 passages, or after at least 40 passages, or after at least 50 passages, or after at least 60 passages, or after at least 70 passages, or after at least 80 passages, or after at least 90 passages, or after at least 100 passages in a serum-free medium of the invention.

In another embodiment, serum-free medium of the invention support the proliferation of MDCK cells (e.g., non-tumorigenic MDCK cells) to high density. In a specific embodiment, serum-free medium of the invention support the proliferation of MDCK cells to a density of least $5 \times 10^5$ cells/mL, at least $6 \times 10^5$ cells/mL, at least $7 \times 10^5$ cells/mL, at least $8 \times 10^5$ cells/mL, at least $9 \times 10^5$ cells/mL, at least $1 \times 10^6$ cells/mL, at least $1.2 \times 10^6$ cells/mL, at least $1.4 \times 10^6$ cells/mL, at least $1.6 \times 10^6$ cells/mL, at least $1.8 \times 10^6$ cells/mL, at least $2.0 \times 10^6$ cells/mL, at least $2.5 \times 10^6$ cells/mL, at least $5 \times 10^6$ cells/mL, at least $7.5 \times 10^6$ cells/mL, or at least $1 \times 10^7$. In another specific embodiment, the serum-free medium of the invention support the proliferation of non-tumorigenic MDCK cells.

In still another embodiment, serum-free medium of the invention support the proliferation of MDCK (e.g., non-tumorigenic MDCK cells) cells to high density and subsequent replication of influenza virus to high titer without the need for a medium exchange step. In a specific embodiment, serum-free medium of the invention support the proliferation of MDCK cells to high density and subsequent replication of influenza virus (e.g., ca/ts strains) to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8 or at least 10.0 without the need for a medium exchange step. In other specific embodiments, serum-free medium of the invention support the proliferation of non-tumorigenic MDCK cells to high density and subsequent replication of influenza virus including, but not limited to influenza viruses described supra.

In one embodiment, serum-free medium of the invention comprise a plant hydrolysate. Plant hydrolysates include but are not limited to, hydrolysates from one or more of the following: corn, cottonseed, pea, soy, malt, potato and wheat. Plant hydrolysates may be produced by enzymatic hydrolysis and generally contain a mix of peptides, free amino acids and growth factors. Plant hydrolysates are readily obtained from a number of commercial sources including, for example, Marcor Development, HyClone and Organo Technie. It is also contemplated that yeast hydrolysates my also be utilized instead of, or in combination with plant hydrolysates. Yeast hydrolysates are readily obtained from a number of commercial sources including, for example, Sigma-Aldrich, USB Corp, Gibco/BRL and others. In certain embodiments, synthetic hydrolysates can be used in addition or in place of plant or yeast hydrolysates. In certain embodiments, serum-free medium of the invention comprise a plant hydrolysate at a final concentration of between about 0.1 g/L to about 5.0 g/L, or between about 0.5 g/L to about 4.5 g/L, or between about 1.0 g/L to about 4.0 g/L, or between about 1.5 g/L to about 3.5 g/L, or between about 2.0 g/L to about 3.0 g/L. In a specific embodiment, serum-free medium of the invention comprise a plant hydrolysate at a final concentration of 2.5 g/L. In another specific embodiment, serum-free medium of the invention comprise a wheat hydrolysate at a final concentration of 2.5 g/L.

In another embodiment, serum-free medium of the invention comprise a lipid supplement. Lipids that may be used to supplement culture medium include but are not limited to chemically defined animal and plant derived lipid supplements as well as synthetically derived lipids. Lipids which may be present in a lipid supplement includes but is not limited to, cholesterol, saturated and/or unsaturated fatty acids (e.g., arachidonic, linoleic, linolenic, myristic, oleic, palmitic and stearic acids). Cholesterol may be present at concentrations between 0.10 mg/ml and 0.40 mg/ml in a 100× stock of lipid supplement. Fatty acids may be present in concentrations between 1 µg/ml and 20 µg/ml in a 100× stock of lipid supplement. Lipids suitable for medium formulations are readily obtained from a number of commercial sources including, for example HyClone, Gibco/BRL and Sigma-Aldrich. In certain embodiments, serum-free medium of the invention comprise a chemically defined lipid concentrate at a final concentration of between about 0.1× to about 2×, or between about 0.2× to about 1.8× or between about 0.3× to about 1.7×, or between about 0.4× to about 1.6×, or between about 0.5× to about 1.5×, or between about 0.6× to about 1.4×, or between about 0.7× to about 1.3×, or between about 0.8× and about 1.2×. In a specific embodiment, serum-free medium of the invention comprise a chemically defined lipid concentrate (CDCL) solution at a final concentration of 1×. In another specific embodiment, serum-free medium of the invention comprise the chemically defined lipid concentrate (CDCL) solution (Table 4) at a final concentration of 1×.

In another embodiment, serum-free medium of the invention comprise trace elements. Trace elements which may be used include but are not limited to, $CuSO_4.5H_2O$, $ZnSO_4.7H_2O$, Selenite.2Na, Ferric citrate, $MnSO_4.H_2O$, $Na_2SiO_3.9H_2O$, Molybdic acid-Ammonium salt, $NH_4VO_3$, $NiSO_4.6H_2O$, $SnCl_2$ (anhydrous), $AlCl_3.6H_2O$, $AgNO_3$, $Ba(C_2H_3O_2)_2$, KBr, $CdCl_2$, $CoCl_2.6H_2O$, $CrCl_3$ (anhydrous), NaF, $GeO_2$, KI, RbCl, $ZrOCl_2.8H_2O$. Concentrated stock solutions of trace elements are readily obtained from a number of commercial sources including, for example Cell Grow (see Catalog Nos. 99-182, 99-175 and 99-176). In certain embodiments, serum-free medium of the invention comprise Trace Element Solutions A, B and C (Table 3) at a final concentration of between about 0.1× to about 2×, or between about 0.2× to about 1.8× or between about 0.3× to about 1.7×, or between about 0.4× to about 1.6×, or between about 0.5× to about 1.5×, or between about 0.6× to about 1.4×, or between about 0.7× to about 1.3×, or between about 0.8× and about 1.2×. In a specific embodiment, serum-free medium of the invention comprise Trace Element Solutions A, B and C (Table 3) at a final concentration of 1×.

In another embodiment, serum-free medium of the invention comprise one or more hormone, growth factor and/or other biological molecules. Hormones include, but are not limited to triiodothyronine, insulin and hydrocortisone. Growth factors include but are not limited to Epidermal Growth Factor (EGF), Insulin Growth Factor (IGF), Transforming Growth Factor (TGF) and Fibroblast Growth Factor (FGF). In a particular embodiment, serum-free medium of the invention comprise Epidermal Growth Factor (EGF). Other biological molecules, include cytokines (e.g., Granulocyte-macrophage colony-stimulating factor (GM-CSF), interferons, interleukins, TNFs), chemokines (e.g., Rantes, eotaxins, macrophage inflammatory proteins (MIPs)) and prostaglandins (e.g., prostaglandins E1 and E2). In one embodiment, serum-free medium of the invention comprise a growth factor at a final concentration of between about 0.0001 to about 0.05 mg/L, or between about 0.0005 to about 0.025 mg/L, or between about 0.001 to about 0.01 mg/L, or between about 0.002 to about 0.008 mg/L, or between about 0.003 mg/L to about 0.006 mg/L. In a specific embodiment, serum-free medium of the invention comprise EGF at a final concentration of 0.005 mg/L. In a one embodiment, serum-free medium of the invention comprise triiodothyronine at a final concentration of between about $1\times10^{-12}$ M to about $10\times10^{-12}$ M, or between about $2\times10^{-12}$ M to about $9\times10^{-12}$ M, or between about $3\times10^{-12}$ M to about $7\times10^{-12}$ M, or between about $4\times10^{-12}$ M to about $6\times10^{-12}$ M. In a specific embodiment, serum-free medium of the invention comprise triiodothyronine at a final concentration of $5\times10^{-12}$ M. In one embodiment, serum-free medium of the invention comprise insulin at a final concentration of between about 1 mg/L to about 10 mg/L, or between about 2.0 to about 8.0 mg/L, or between about 3 mg/L to about 6 mg/L. In a specific embodiment, serum-free medium of the invention comprise insulin at a final concentration of 5 mg/L. In certain embodiments, serum-free medium of the invention comprise a prostaglandin at a final concentration of between about 0.001 mg/L to about 0.05 mg/L, or between about 0.005 mg/L to about 0.045 mg/L, or between about 0.01 mg/L to about 0.04 mg/L, or between about 0.015 mg/L to about 0.035 mg/L, or between about 0.02 mg/L to about 0.03 mg/L. In a specific embodiment, serum-free medium of the invention comprise a prostaglandin at a final concentration of 0.025 mg/L. In another specific embodiment, serum-free medium of the invention comprise prostaglandin E1 at a final concentration of 0.025 mg/L.

In still another embodiment, serum-free medium of the invention are fortified with one or more medium component selected from the group consisting of putrescine, amino acids, vitamins, fatty acids, and nucleosides. In specific embodiments, serum-free medium of the invention are fortified with one or more medium component such that the concentration of the medium component is about 1 fold, or about 2 fold, or about 3 fold, or about 4 fold, or about 5 fold higher or more than is typically found in a medium routinely used for propagating cell, such as, for example, Dulbecco's Modified Eagle's Medium/Ham's F12 medium (DMEM/F12). The standard composition of DMEM/F12 is provided for reference below in Table 1. In a specific embodiment, serum-free medium of the invention are fortified with putrescine. In another specific embodiment, serum-free medium of the invention are fortified with putrescine such that the concentration of putrescine is about 5 fold higher, or more, than is typically found in DMEM/F12.

Fatty acids which may be fortified include, unsaturated fatty acid, including but not limited to, linoleic acid and α-linolenic acid (also referred to as essential fatty acids) as well as, myristoleic acid, palmitoleic acid, oleic acid, arachidonic acid, eicosapentaenoic acid, erucic acid, docosahexaenoic acid; saturated fatty acids, including but not limited to, butanoic acid, hexanoic acid, octanoic acid, decanoic acid, dodecanoic acid, tetradecanoic acid, hexadecanoic acid, octadecanoic acid, eicosanoic acid, docosanoic acid, tetracosanoic acid and sulfur containing fatty acids including lipoic acid. In certain embodiments, the serum-free medium of the invention are fortified with extra fatty acids in addition to that provided by a lipid supplement as described supra. In a specific embodiment, serum-free medium of the invention are fortified with linoleic acid and linolenic acid. In another specific embodiment, serum-free medium of the invention are fortified with linoleic acid and linolenic acid such that the concentrations of linoleic acid and linolenic acid are about 5 fold higher, or more, than is typically found in DMEM/F12.

Amino acids which may be fortified in include the twenty standard amino acids (alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine) as well as cystine and non-standard amino acids. In certain embodiments, one or more amino acids which are not synthesized by non-tumorigenic MDCK cells, commonly referred to as "essential amino acids", are fortified. For example, eight amino acids are generally regarded as essential for humans: phenylalanine, valine, threonine, tryptophan, isoleucine, methionine, leucine, and lysine. In a specific embodiment, serum-free medium of the invention are fortified with cystine and all the standard amino acids except glutamine (DMEM/F12 is often formulated without glutamine, which is added separately), such that the concentrations of cystine and the standard amino acids are about 5 fold higher, or more, than is typically found in DMEM/F12. In certain specific embodiment, serum-free medium of the invention comprise glutamine at a concentration of between about 146 mg/L to about 1022 mg/L, or between about 292 mg/L to about 876 mg/L, or between about 438 mg/L to about 730 mg/L. In another specific embodiment, serum-free medium of the invention comprise glutamine at a concentration of 584 mg/mL.

Vitamins which may be fortified include, but are not limited to, ascorbic acid (vit A), d-biotin (vit $B_7$ and vit H), D-calciumpantothenate, cholecalciferol (vit $D_3$), choline chloride, cyanocobalamin (vit $B_{12}$), ergocalciferol (vit $D_2$), folic acid (vit $B_9$), menaquinone (vit $K_2$), myo-inositol, niacinamide (vit $B_3$), p-amino benzoic acid, pantothenic acid (vit $B_5$), phylloquinone (vit $K_1$), pyridoxine (vit $B_6$), retinol (vit A), riboflavin (vit $B_2$), alpha-tocopherol (vit E) and thiamine (vit $B_1$). In a specific embodiment, serum-free medium of the invention are fortified with d-biotin, D-calcium, pantothenate, choline chloride, cyanocobalamin, folic acid, myo-inositol, niacinamide, pyridoxine, riboflavin, and thiamine such that the concentrations of the indicated vitamins are about 5 fold higher, or more, than is typically found in DMEM/F12.

Nucleosides which may be fortified include, but are not limited to, cytidine, uridine, adenosine, guanosine, thymidine, inosine, and hypoxanthine. In a specific embodiment, serum-free medium of the invention are fortified with hypoxanthine and thymidine such that the concentrations of hypoxanthine and thymidine are about 5 fold higher, or more, than is typically found in DMEM/F12.

Additional components that may be added to cell culture medium include, but are not limited to, sodium bicarbonate, a carbon source (e.g., glucose), and iron binding agents. In one embodiment, serum-free medium of the invention comprise sodium bicarbonate at a final concentration of between about 1200 mg/L to about 7200 mg/L, or between about 2400 mg/L and about 6000 mg/mL, or about 3600 mg/mL and about 4800 mg/mL. In a specific embodiment, serum-free medium of the invention comprise sodium bicarbonate at a final concentration of 4400 mg/mL. In one embodiment, serum-free medium of the invention comprise glucose as a carbon source. In another embodiment, serum-free medium of the invention comprise glucose at a final concentration of between about 1 g/L to about 10 g/L, or about 2 g/L to about 10 g/L, or about 3 g/L to about 8 g/L, or about 4 g/L to about 6 g/L, or about 4.5 g/L to about 9 g/L. In a specific embodiment, serum-free medium of the invention comprise glucose at a final concentration of 4.5 g/L. It is specifically contemplated that additional glucose may be added to a serum-free medium of the invention that is to be used for the proliferation of non-tumorigenic MDCK cells to high density and subsequent replication of influenza virus to avoid depletion of the carbon source. Accordingly, in certain embodiments, a serum free media of the present invention comprises an additional 1-5 g/L of glucose for a final glucose concentration of between about 5.5 g/L to about 10 g/L.

Iron binding agents which may be utilized include proteins such as transferrin and chemical compounds such as tropolone (see, e.g., U.S. Pat. Nos. 5,045,454; 5,118,513; 6,593,140; and PCT publication number WO 01/16294). In one embodiment, serum-free medium of the invention comprise tropolone (2-hydroxy-2,4,6-cyclohepatrien-1) and a source of iron (e.g., ferric ammonium citrate, ferric ammonium sulfate) instead of transferrin. For example, tropolone or a tropolone derivative will be present in an excess molar concentration to the iron present in the medium at a molar ratio of between about 5 to 1 and about 1 to 1. In certain embodiments, serum-free medium of the invention comprise tropolone or a tropolone derivative in an excess molar concentration to the iron present in the medium at a molar ratio of about 5 to 1, or about 3 to 1, or about 2 to 1, or about 1.75 to 1, or about 1.5 to 1, or about 1.25 to 1. In a specific embodiment, serum-free medium of the present invention comprises Tropolone at a final concentration of 0.25 mg/L and ferric ammonium citrate (FAC) at a final concentration of 0.20 mg/L and (see, e.g., Table 2).

The addition of components as described supra to a medium formulation can alter the osmolality. Accordingly, in certain embodiments, amount of one or more components typically found in DMEM/F12 is reduced to maintain a desired osmolality. In one embodiment, the concentration of sodium chloride (NaCl) is reduced in a serum-free medium of the invention. In another embodiment, the concentration of NaCl in a serum-free medium of the invention is about between about 10% to about 90%, or about 20% to about 80%, or about 30% to about 70%, or about 40% to about 60% of that typically found in DMEM/F12. In a specific embodiment, the final concentration of NaCl in a serum-free medium of the invention is 50% of that typically found in DMEM/F12. In another specific embodiment, the final the concentration of NaCl in a serum-free medium of the invention is 3500 mg/L.

In certain embodiments, the number of animal derived components present in serum-free medium of the invention are minimized or even eliminated. For example, commercially available recombinant proteins such as insulin and transferrin derived from non-animal sources (e.g., Biological Industries Cat. No. 01-818-1, and Millipore Cat. No. 9701, respectively) may be utilized instead proteins derived from an animal source. In a specific embodiment, all animal derived components are replaced by non-animal-derived products with the exception of cholesterol which may be a component of a chemically defined lipid mixture. To minimize the risks typically associated with animal derived products cholesterol may be from the wool of sheep located in regions not associated with adventitious agents including, but not limited to prions.

In a specific embodiment, serum-free medium of the invention comprise all the components of the MediV SFM 110 medium listed in Table 2, at the final concentrations indicated. In another specific embodiment, serum-free medium of the invention consist essentially of all the components of the MediV SFM 110 medium listed in Table 2, at the final concentrations indicated. In still another specific embodiment, MediV SFM 110 medium consisting of the components listed in Table 2 is a serum-free medium of the invention.

TABLE 1

DMEM/F12 Medium Formulation

| Component | mg/L |
|---|---|
| Salts | |
| Calcium Chloride, Anhydrous | 116.6 |
| Magnesium Chloride | 28.64 |
| Magnesium Sulfate, Anhydrous | 48.84 |
| Potassium Chloride | 311.8 |
| Sodium Chloride | 6999.5 |
| Sodium Phosphate, Monobasic, Monohydrate | 62.5 |
| Sodium Phosphate, Dibasic, Anhydrous | 71.02 |
| Trace Metals | |
| Cupric Sulfate, Pentahydrate | 0.0013 |
| Ferric Nitrate, Nonahydrate | 0.05 |
| Ferrous Sulfate, Heptahydrate | 0.417 |
| Zinc Sulfate, Heptahydrate | 0.432 |
| Other | |
| Putrescine, 2HCl | 0.081 |
| Sodium Bicarbonate | 2200 |
| Sodium Pyruvate | 55 |
| Vitamins | |
| d-Biotin (vit B7 and vit H) | 0.0035 |
| D-Calcium Pantothenate | 2.24 |
| Choline Chloride | 8.98 |
| Cyanocobalamin (vit B12) | 0.68 |
| Folic Acid | 2.65 |
| myo-Inositol | 12.6 |
| Niacinamide | 2.02 |
| Pyridoxine HCl (vit B6) | 2.031 |
| Riboflavin(vit B2) | 0.219 |
| Thiamine HCl (vit B1) | 2.17 |
| Amino Acids | |
| L-Alanine | 4.45 |
| L-Arginine HCl | 147.5 |
| L-Asparagine $H_2O$ | 7.5 |
| L-Aspartic Acid | 6.65 |
| L-Cysteine HCl $H_2O$ | 17.56 |
| L-Cystine 2HCl | 31.29 |
| L-Glutamic Acid | 7.35 |
| Glycine | 18.75 |
| L-Histidine HCl $H_2O$ | 31.48 |
| L-Isoleucine | 54.47 |
| L-Leucine | 59.05 |
| L-Lysine HCl | 91.25 |
| L-Methionine | 17.24 |
| L-Phenylalanine | 35.48 |
| L-Proline | 17.25 |
| L-Serine | 26.25 |
| L-Threonine | 53.45 |
| L-Tryptophan | 9.02 |
| L-Tyrosine 2Na | 55.79 |
| L-Valine | 52.85 |
| Nucleosides | |
| Hypoxanthine, Na salt | 2.39 |
| Thymidine | 0.365 |
| Fatty Acids | |
| α Linoleic Acid | 0.042 |
| α DL--Lipoic Acid | 0.105 |

6.3.2 Bead to Bead Transfer

In one embodiment, non-tumorigenic MDCK cells are cultivated as adherent cells on a surface to which they attach. Adherent surfaces on which tissue culture cells can be grown on include but are not limited to, surface modified polystyrene plastics, protein coated surfaces (e.g., fibronectin and/or collagen coated glass/plastic) as well as a large variety of commercially available microcarriers (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor; Cytodex 1 and Cytodex 3, GE Healthcare Life Science). Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. The choice of adherent surface is determined by the methods utilized for the cultivation of the non-tumorigenic MDCK cells.

In one embodiment, the microcarrier is used at a concentration of between about 1 to about 4 g/L. In another embodiment, the microcarrier is used at a concentration of between about 2 to about 3 g/L. In certain embodiments the culture vessel (e.g. bioreactor) is seeded with the MDCK cells to be cultured at a seeding density of about 0.5 to about $2\times10^5$ cells/mL. In a specific embodiment, the seeding density is between about 0.7 to about $1.8\times10^5$ cells/mL, or between about 0.8 to about $1.6\times10^5$ cells/mL, or between about 0.9 to about $1.4\times10^5$ cells/mL, or between about 1.0 to about $1.2\times10^5$ cells/mL. Alternatively, the seeding density can be calculated on a per microcarrier basis. Accordingly, in certain embodiments the culture vessel (e.g. bioreactor) is seeded with the MDCK cells to be cultured at a seeding density of about 10 to about 40 cells/microcarrier, or of about 12 to about 38 cells/microcarrier, cells/microcarrier, or of about 14 to about 36 cells/microcarrier, or of about 16 to about 34 cells/microcarrier, or of about 18 to about 32 cells/microcarrier, or of about 20 to about 30 cells/microcarrier.

During the process of subculturing adherent cells (i.e., proliferating the cells, expanding the cell culture) the cells must be transferred from a confluent support surface (e.g., flask surface, microcarrier, etc) onto a new support surface. A number of methods can be utilized to effect such cell transfer. For example, proteases, including trypsin, TrypLE and collagenase, may be used to remove cells from flasks or microcarriers the cells are then, washed if desired, and diluted into a larger flask or into a larger volume of microcarrier containing medium for expansion. This process is commonly referred to a "splitting" the culture and may be quantified as the ratio of the original culture to the final culture. For example a split ratio of 1:8 indicates that 1 part of the original (e.g., 10 mL) culture is added to 7 parts fresh culture medium (e.g., 70 mL) to yield 80 mL. Alternatively, the number of cells in the original culture is determined and the dilution is calculated based on the desired seeding density and volume of the final culture. It is preferable to use a non-animal derived protease for such applications such as, TrypLE (Invitrogen, Carlsbad, Calif.). Alternatively, in microcarrier cultures, after the cells have detached fresh medium and/or microcarrier beads may then be added to the culture. In some embodiments, the protease treated culture is transferred to a larger culture vessel before, during or after the addition of fresh medium and/or microcarriers.

In a specific embodiment, a cell culture of MDCK cells (e.g., non-tumorigenic MDCK cells) growing as adherent cells on microcarriers are treated with a protease (e.g., TrypLE). The protease may be inactivated (e.g., by the addition of a protease inhibitor such as lima bean trypsin inhibitor) as needed, and fresh medium and/or microcarrier beads may then be added to the culture. In some embodiments, the protease treated culture is transferred to a larger culture vessel before, during or after the addition of fresh medium and/or microcarriers.

The use of proteases in bead to bead transfer methods can result in poor cell spreading and low cell counts. Accordingly, the present invention also provides methods of effecting bead to bead transfer which minimize or even eliminate the amount of protease needed to facilitate bead to bead transfer including but not limited to the method exemplified in the Examples at Section 8.2, which is also utilized in the Examples in Section 8.1. In particular, the inventors have determined that the amount of protease needed to release the cells from microcarriers can be reduced by at least 20 fold by pre-treatment with a chelating agent, in particular by pre-treatment at a pH higher than that used for the proliferation of the cells.

In some embodiments, bead to bead transfer is facilitated by pre-treating the cells with a chelating agent prior to the addition of a protease (e.g., TrypLE). In other embodiments, bead to bead transfer is facilitated by the addition of a chelating agent (e.g., EDTA) and incubation at a pH above that used for cell proliferation. In a specific embodiment, a cell culture of non-tumorigenic MDCK cells growing as adherent cells on microcarriers is treated with a chelating agent (e.g., EDTA) at a higher pH than used during proliferation of the cells prior to the addition of a protease. In certain embodiments, the pH is monitored and adjusted as need to facilitate detachment of the cells from the microcarrier substrate. After the cells have detached fresh medium and/or microcarrier beads may then be added to the culture. In some embodiments, the culture, with or without the original microcarriers is transferred to a larger culture vessel before, during or after the addition of fresh medium and/or microcarriers.

In certain embodiments, the cells are washed with a wash medium (e.g., a buffered salt solution) prior to being detached. Medium useful for washing cells include, but are not limited to, Hepes-Buffered solutions, Phosphate-Buffered Saline, Dulbecco's Phosphate-Buffered Saline, Hank's Balanced Salt Solution, Earle's Balanced Salt Solution. The process of washing the cells involves replacing a portion or all of the medium (growth and/or wash medium) with fresh wash medium (i.e., buffered salt solution). The process may be repeated multiple times. Generally, the microcarrier beads are allowed to settle for a time (e.g., 10 to 40 minutes) and the growth medium is removed from the vessel. Optionally, the removal of medium from a cell culture can be performed utilizing an alternating low shear tangential flow device, see for example U.S. Pat. No. 6,544,424. In certain embodiments, between about 50% to about 90% of the medium (growth and/or wash medium) is removed during the wash step. In certain embodiments, the medium is replaced with a volume of wash medium (i.e., buffered salt solution) that is less than, the same, or greater than, the volume of medium that was removed. In one embodiment, wash medium is added such that the resulting volume of cell culture is between about 25% to about 100% of the original working volume of the cell culture. In a specific embodiment, a wash medium is added to about 40% to about 60% of the original working volume of the cell culture. In another specific embodiment, a wash medium is added to about 90% to about 100% of the original working volume of the cell culture. In certain embodiments, the cells are washed two or more times.

In certain embodiments, the wash medium comprises a chelating agent. Chelating agents which can be utilized include but are not limited to, ethylenediaminetetraacetic acid (EDTA), Diethylenetriaminepentaacetate (DTPA), Ethylenebis (oxyethylene-trinitrilo)tetraacetic acid (EGTA). In a specific embodiment, the chelating agent is EDTA. In certain embodiments, the wash medium comprises the chelating agent at a concentration of between about 0.25 mM to about 0.75 mM. In certain other embodiments, the wash medium comprises the chelating agent at a concentration of between about 0.4 mM to about 0.6 mM. In a specific embodiment, the wash medium comprises the chelating agent concentration of about 0.5 mM.

In one embodiment, the pH of the wash medium comprising the chelating agent is between about 7.6 and about 8.4. In a specific embodiment, the pH of the wash medium comprising the chelating agent is between about 7.8 and about 8.2. In another specific embodiment, the pH of the wash medium comprising the chelating agent is between about 7.9 and about 8.1. The addition of a wash medium comprising a chelating agent to a cell culture may alter the pH of the resulting cell culture in wash medium. Accordingly, in certain embodiments, the pH of a cell culture being washed with a wash medium comprising a chelating agent is adjusted to between about 7.6 and about 8.4, as needed, after addition of the wash medium to the cell culture. In a specific embodiment, the pH of a cell culture being washed with a wash medium comprising a chelating agent is adjusted to between about 7.8 and about 8.2, as needed, after addition of the wash medium to the cell culture. In another specific embodiment, the pH of a cell culture being washed with a wash medium comprising a chelating agent is adjusted to between about 7.9 and about 8.1, as needed, after addition of the wash medium to the cell culture.

In certain embodiments, the cell culture is agitated after the addition of the wash medium comprising the chelating agent and prior to an additional wash step and/or the addition of a protease. Agitation of the culture may take place using means well known in the art, including but not limit to, stirring, shaking, rotating, and the like. The rate and duration of agitation is determined by the volume of the culture, the components of the wash medium, and the type of cells in the cell culture. In certain embodiments, the cell culture is agitated at a similar rate as that used for propagation of the cells. In other embodiments, the cell culture is agitated at a higher rate than that used for propagation of the cells. When a higher agitation rate is used the rate is increased between about 10% to about 90%, or between about 20% to about 80%, or between about 30% to about 70%, or between about 40% to about 65%. In a specific embodiment, the agitation rate used is between about 40% to about 65%. In certain embodiments, the cell culture is agitated for between about 5 minutes to about 60 minutes. In a specific embodiment, the cell culture is agitated for about 20 to about 40 minutes.

In certain embodiments, a protease (e.g., serine protease) is added to the cell culture during a wash but after any agitation. In a specific embodiment, the cells are washed two or more times and the protease is added during the last wash after any agitation. The protease is, in certain aspects of the invention, a serine protease, or a cysteine protease, or an asparigine protease. In a specific embodiment the protease is a serine protease (e.g., trypsin, TrypLE, etc). In another embodiment, the protease from *Streptomyces griseus* described in U.S. application Ser. No. 11/455,818 is used. The trypsin can be from an animal source, or, more preferably, is from a recombinant source. The amount of protease added to effect detachment under these conditions will be at least 5× less than that needed if the cells had not be pre-treated with a chelating agent and will be determined by the volume of the volume of the culture and the concentration of the protease. By way of example, the commercially available TrypLE™ Express provided as a 10× stock, would generally be used at a final concentration of about 1× (see, for example, Invitrogen™ TrypLE Select Product News) to detach highly adherent cells, such as MDCK cells. As demonstrated herein (see, Section 8.2) the final concentration of TrypLE™ required to detach cells from microcarriers is 0.05×, a 20 fold reduction. Accordingly, in certain embodiments, the final concentration of protease added to the cell culture is about 0.5×, or about 0.1×, or about 0.09×, or about 0.08×, or about 0.07×, or about 0.06× or about 0.05×, or about 0.04× or about 0.02×, where 1× represents the final concentration of protease needed to detach cells which have not be pre-treated with a chelating agent under identical dissociation conditions.

In one embodiment, MDCK cells are cultivated as adherent cells in a culture system. Culture systems which may be utilized to cultivate MDCK cells include for example, batch culture systems and fed batch culture systems where additional nutrients (e.g., carbon source, amino acids, etc) are added as they are depleted from the starting medium to facilitate growth to high cell densities. Alternatively or optional a perfusion culture systems (e.g., using cell retention systems, such as, for example, centrifugation, filtration, spin filters and the like) may be used to facilitate medium exchange and/or supplementation of depleted nutrients. In a specific embodiment, non-tumorigenic MDCK cells are cultivated as adherent cells in a batch culture system without medium exchange/supplementation (e.g., feeding or perfusion) using a serum-free medium of the invention (e.g., MediV SFM 110). Additional guidance regarding culture of MDCK cells (e.g., non-tumorigenic MDCK cells) as adherent cells may be found, for example, in US Patent Application Publication Nos. 2003/0108860; 2005/0118140; and PCT Publication WO 2008/105931. Commonly used culture systems useful for cultivation of MDCK cells include stirred vessel bioreactors.

6.3.3 Influenza Virus Culture Conditions

The present invention provides methods for the cultivation of MDCK cells (e.g., non-tumorigenic MDCK cells) and other animal cells in serum-free media formulations as set forth above. It is specifically contemplated that additional culture conditions may play a role in the maintenance of the properties of the MDCK cells, including being non-tumorigenic, being non-oncogenic, growing as adherent cells, growing as non-adherent cells, having an epithelial-like morphology, supporting the replication of various viruses, and supporting the growth of influenza viruses (e.g., cold-adapted, and/or temperature sensitive, and/or attenuated) to high titer, e.g., a $\log_{10}$ TCID$_{50}$/mL and/or a $\log_{10}$ FFU/mL of at least about 7.8, or at least about 8.0, or at least about 9.0. These culture conditions include, but are not limited to, the choice of adherent surface, cell density, temperature, $CO_2$ concentration, method of cultivation, agitation rates, dissolved oxygen content and pH.

It is specifically contemplated that the culture conditions may be adapted in a number of ways to optimize the growth of MDCK cells (e.g., non-tumorigenic MDCK cells). Such adaptations may also result in a increase in the production of viral material (e.g., virus), as described, for example, in US Patent Application Publication No. 2005/0118698. Alternatively, the culture conditions may be adapted to optimize the production of vaccine material from MDCK cells without regard for the growth of the cells. These culture conditions include but are not limited to adherent surface, cell density, temperature, $CO_2$ concentration, method of cultivation, dissolved oxygen content and pH.

In one embodiment, MDCK cells (e.g., non-tumorigenic MDCK cells) are cultivated at a $CO_2$ concentration of at least 1%, or of at least 2%, or of at least 3%, or of at least 4%, or of at least 5%, or of at least 6%, or of at least 7%, or of at least 8%, or of at least 9%, or of at least 10%, or of at least 20%.

In one embodiment the dissolved oxygen (DO) concentration ($pO_2$ value) is advantageously regulated during the cultivation of MDCK and is in the range from 5% and 100% (based on the air saturation), or between 10% and 60%. In a specific embodiment the dissolved oxygen (DO) concentration ($pO_2$ value) is at least 10%, or at least 20%, or at least 30%, or at least 50%, or at least 60%. In a specific embodiment, the DO concentration is maintained at 50%. In a particular embodiment, the DO is flowed down to 50% and then maintained at that level. Methods for maintaining DO levels include, for example, sparging with pure oxygen.

In another embodiment, the pH of the culture medium used for the cultivation of the non-tumorigenic MDCK cells is regulated during culturing and is in the range from pH 6.4 to pH 8.0, or in the range from pH 6.8 to pH 7.4. In a specific embodiment, the pH of the culture medium is at about 6.4, or at about 6.6, or at about 6.8, or at about 7.0, or at about 7.2, or at about 7.4, or at about 7.6, or at about 7.8, or at least 8.0. In a particular embodiment the pH of the culture medium is about 7.4.

In a further embodiment, MDCK cells are cultured in a serum free medium of the invention at a temperature of 25° C. to 39° C. It is specifically contemplated that the culture temperature may be varied depending on the process desired. For example, the non-tumorigenic MDCK cells may be grown at 37±2° C. for proliferation of the cells and at a lower temperature (e.g., 25° C. to 35° C.) of for the production of vaccine material (e.g., virus). In another embodiment, the cells are cultured at a temperature of less than 30° C., or of less than 31° C., or of less than 32° C., or of less than 33° C., or of less than 34° C. for the production of vaccine material. In another embodiment, the cells are cultured at a temperature of 30° C., or 31° C., or 32° C., or 33° C., or 34° C. for the production of vaccine material. In a specific embodiment, the cells are cultured at a temperature of 33±2° C. for the production of vaccine material.

In certain embodiments, MDCK cells are cultured in a serum-free medium of the invention in a stirred-vessel bioreactor (e.g., plastic single use, glass or stainless steel reusable bioreactors) and one or more parameters selected from the group consisting of temperature, agitation rate, pH, dissolved oxygen (DO), $O_2$ and $CO_2$ flow rate, are monitored and/or controlled. In one embodiment, the temperature is maintained at between about 30° C. to about 42° C., or between about 33° C. to about 39° C., or between about 35° C. to about 38° C. In a specific embodiment, the temperature is maintained at about between about 36° C. to about 38° C. In one embodiment, the agitation rate is maintained at between about 100 to 200 rpm. In a specific embodiment a single use bioreactor is utilized and the rate of agitation is maintained at between about 80 to about 120 rpm, or between about 90 to about 100 rpm. In another specific embodiment a reusable bioreactor is utilized and the rate of agitation is maintained at between about 150 to about 200 rpm, or between about 160 to about 180 rpm. Agitation rates are controlled by means well known in the art. The type and size of bioreactor utilized as well as the type and number of impeller(s) used may require the agitation rate to be adjusted to maximize cell growth and/or minimize cell damage.

In another embodiment, the pH of the MDCK cell culture is maintained at between about 6.4 to pH 8.0. In a specific embodiment the pH of the starting culture is between about 6.8 to about 7.6 and the pH of the culture is maintained at about 7.0 to about 7.5 during the culture process. The initial pH may be lower or higher then the desired range and that the pH may be allowed to increase or decrease to the desired level (e.g., 7.4) where it is maintained. In a particular embodiment the pH is maintained at about 7.4. The pH may be controlled by sparging $CO_2$ and/or by adding acid (e.g., HCL) or base (e.g., NaOH, $NaHCO_3$, $Na_2CO_3$) as needed.

In still another embodiment the acceptable range for the DO is between about 100 to about 35%. In a specific embodiment, the DO of the MDCK cell culture is maintained at between about 35% to about 50%, or at about 50%. In another specific embodiment, the DO should not drop below about 35%. In certain embodiments, the initial DO may be 100% and the DO may be allowed to drop down to a predetermined level (e.g., 50%) where it is maintained. The DO is maintained, for example, by sparging $O_2$. In certain embodiments, the $O_2$ flow rate is maintained at less then about 2.0 L/min. In certain embodiments, the $CO_2$ flow rate is maintained at less then about 0.4 L/min. In still other embodiments, a constant total flow rate is maintained (e.g., 40 mL/min) and $N_2$ gas is supplied to maintain the flow rate. Accordingly, the supply of $N_2$ gas can be calculated from $O_2$ and $CO_2$ gases used to maintain the DO and pH.

The content of glucose, glutamine, lactate, other medium components, as well as the pH and $pO_2$ value in the medium and other parameters, such as agitation, may be readily manipulated during culture of the non-tumorigenic MDCK cells such that the cell density and/or virus production is optimized.

6.3.4 Respiratory Syncitial Virus Culture Conditions

In a specific embodiment, cells are cultured before infection with a cell-associated virus described herein to achieve a certain total viable cell count. For example, Vero cells may be cultured in VP-SFM supplemented with 4 mM L-glutamine and 1% CDLC) at approximately 37° C. and total viable cell counts and cell viability is measured. In a specific embodiment, cells are infected with cell-associated virus when a certain average viable cell count is achieved. For example, an average viable cell count of approximately $1.5 \times 10^8$ cells/tissue culture vessel or more may be achieved before the cells are infected with a cell-associated virus described herein, such as RSV. In one embodiment, an average viable cell count of approximately $1 \times 10^6$ cells/tissue culture vessel to approximately $1 \times 10^{14}$ cells/tissue culture vessel as measured using, e.g., a Vi-cell counter, is achieved before cells are infected with a cell-associated virus described herein. In another embodiment, an average viable cell count of approximately $1 \times 10^6$ cells/tissue culture vessel, approximately $5 \times 10^6$ cells/tissue culture vessel, approximately $1 \times 10^7$ cells/tissue culture vessel, or approximately $5 \times 10^7$ cells/tissue culture vessel as measured using, e.g., a Vi-cell counter, is achieved before cells are infected with a cell-associated virus described herein. In another embodiment, an average viable cell count of approximately $1 \times 10^8$ cells/tissue culture vessel, approximately $5 \times 10^8$ cells/tissue culture vessel, approximately $1 \times 10^9$ cells/tissue culture vessel, approximately $5 \times 10^9$ cells/tissue culture vessel, or approximately $1 \times 10^{10}$ cells/tissue culture vessel as measured using, e.g., a Vi-cell counter, is achieved before cells are infected with a cell-associated virus described herein.

A multiplicity of infection (MOI) that is determined to be optimal for the chosen cells is used to infect cells. In a specific embodiment, a MOI of approximately 0.0001 to approximately 1 or approximately 0.0005 to 0.005 is used to infect the cells described herein. In another embodiment, a MOI of approximately 0.0001, approximately 0.0005 or approximately 0.00075 is used to infect the cells described herein. In another embodiment, a MOI of approximately 0.001, approximately 0.005, approximately 0.0075 or approximately 0.01 is used to infect the cells described herein. In yet another embodiment, a MOI of approximately 0.05, approximately 0.075, approximately 0.1 or approximately 0.5 is used to infect the cells described herein. In a specific embodiment, a MOI of approximately 0.01 of rA2cp248/404/1030ΔSH is used to infect Vero cells.

Cell-associated virus-infected cells may be incubated for a period of time in media and under conditions (e.g., temperature, $CO_2$ conditions, and pH) that are appropriate for the cell line chosen and result in optimal yields of virus titer. For example, Vero cells infected with a RSV, such as rA2cp248/ 404/1030ΔSH, may be incubated in SF4 MegaVir medium (Invitrogen Corp., Carlsbad Calif.) supplemented with 4 mM L-glutamine and incubated at approximately 30° C. for approximately 10 days without $CO_2$ before the virus is harvested. In some embodiments, RSV-infected cells (e.g., RSV-infected Vero cells) are incubated for approximately 7 to 14 days before the virus is harvested. In specific embodiments, RSV-infected cells are incubated for approximately 8 days, preferably approximately 9 days, approximately 10 days, approximately 11 days, or approximately 12 days before the virus is harvested.

Cell-associated virus-infected cells described herein can be cultured in any tissue culture vessel known to one of skill in the art. In some embodiments, the cell-associated virus-infected cells are cultured in T-75 flasks or T-225 flasks. In other embodiments, the cell-associated virus-infected cells are cultured in 1 liter, 2 liter, 3 liter, 4 liter or 5 liter tissue culture vessels. In a specific embodiment, the cell-associated virus-infected cells are cultured in at least 40 500 ml working volume roller bottles. In a specific embodiment, the cell-associated virus-infected cells are cultured in a 4 liter tissue culture vessel, such as a roller bottle. In other embodiments, the cell-associated virus-infected cells are cultured in 10 liter, 15 liter, 20 liter or 25 liter tissue culture vessels. In other embodiments, the cell-associated virus-infected cells are cultured in 50 liter, 75 liter or 100 liter tissue culture vessels. In other embodiments, the cell-associated virus-infected cells are cultured in 250 liter, 500 liter or 1000 liter tissue culture vessels. The tissue culture vessels that may be used include flasks, roller bottles, bioreactors and any other tissue culture vessels known to one of skill in the art.

6.4 Production of Vaccine Material

The present invention provides robust methods for the production of viruses in cell culture in which MDCK cells (e.g., non-tumorigenic MDCK cells) are used to produce viruses. In particular, the present invention provides methods for the production of influenza viruses to high titers, without medium exchange or supplementation.

In one embodiment the method for producing influenza viruses comprises the following steps:
(a) proliferating MDCK cells in a serum-free culture medium, while maintaining one or more culture conditions selected from the group consisting of an agitation rate of between about 100 and 200 rpm, a pH of between about 6.0 to about 7.8, a temperature of between about 33° C. and about 42° C., and dissolved oxygen (DO) between about 35% to about 100%;
(b) infecting the proliferated MDCK cells with an influenza virus without exchanging the culture medium; and
(c) incubating the infected proliferated MDCK cells under conditions that permit replication of the influenza virus.

Influenza viruses which may be produced by the methods of the invention are described here (see, for example, Sections 7.2 and 6.7), and include but are not limited to, reassortant viruses that incorporate selected hemagglutinin and/or neuraminidase antigens in the context of an attenuated, temperature sensitive, cold adapted (ca/ts/att) master donor viruses. For example, viruses can comprise the backbones (or one or more vRNA segment) of master donor virus that are one or more of, e.g., temperature-sensitive (ts), cold-adapted (ca), or an attenuated (att) (e.g., A/Ann Arbor/6/60, B/Ann Arbor/1/66, PR8, B/Leningrad/14/17/55, B/14/5/1, B/USSR/ 60/69, B/Leningrad/179/86, B/Leningrad/14/55, B/England/ 2608/76 etc.). Methods for the production of reassortant influenza vaccine strains in either eggs or cell lines include, for example, those disclosed in Kilbourne, E. D. in *Vaccines* ($2^{nd}$ Edition), ed. Plotkin and Mortimer, WB Saunders Co. (1988) and those disclosed in PCT Application PCT Patent Publication Nos. WO 05/062820 and WO 03/091401, and in U.S. Pat. Nos. 6,951,754, 6,887,699, 6,649,372, 6,544,785, 6,001,634, 5,854,037, 5,824,536, 5,840,520, 5,820,871, 5,786,199, and 5,166,057 and U.S. Patent Application Publication Nos. 20060019350, 20050158342, 20050037487, 20050266026, 20050186563, 20050221489, 20050032043, 20040142003, 20030035814, and 20020164770. Other influenza viruses which may be produced by the methods of the invention include recombinant influenza viruses which may express a heterologous gene product, see for example, U.S. Patent Publication Nos. 2004/0241139 and 2004/0253273. In certain embodiments, the method is used to produce cold-adapted, and/or temperature sensitive, and/or attenuated influenza viruses.

In a specific embodiment, the influenza viruses are produced to a peak viral titer $\log_{10}$ $TCID_{50}$/mL and/or $\log_{10}$ FFU/mL of at least about 8.0. In other embodiments, the influenza viruses are produced to a peak viral titer $\log_{10}$ $TCID_{50}$/mL and/or $\log_{10}$ FFU/mL of at least about 8.1, or of at least 8.2, or of at least 8.3, or of at least 8.4, or of at least 8.5, or of at least 8.6, or of at least 8.7, or of at least 8.8, or of at least 8.9, or of at least 9.0.

In certain embodiments, the MDCK cells are proliferated as adherent cells. In a specific embodiment the MDCK cells are non-tumorigenic MDCK cells and are proliferated as adherent cells. In another specific embodiment, the MDCK cells are selected from the group consisting of ATCC Deposit Nos. PTA-6500, PTA-6501, PTA-6502, PTA-6503, PTA-7909 and PTA-7910), and are proliferated as adherent cells. Bioreactors and methods useful for proliferating adherent cells have been described supra (see Sections 0 and 0). In other embodiments, the MDCK cells are proliferated as non-adherent cells. Methods for proliferating non-adherent MDCK cells are known in the art, see for example U.S. Pat. No. 6,455,298. Additional culture conditions such as, for example, temperature, agitation rate, pH, $pO_2$, $CO_2$ concentration, and cell seeding density are described in detail supra (see Sections 0 and 0).

In a specific embodiment, the MDCK cells are proliferated as adherent cells in a stirred vessel bioreactor. In certain embodiments of the method the temperature, agitation rate, pH, $pO_2$ value, $CO_2$ concentration and other parameters of the culture medium to culture the cells are regulated during culturing as described supra (see Sections 0 and 0). In certain embodiments the MDCK cells are proliferated to a cell density of between about $5 \times 10^5$ to about $3 \times 10^6$. Alternatively, or optionally the MDCK cells are proliferated for a set period of time. The initial seeding density, doubling time and desired final cell density will determine the time period for proliferation. In such embodiments, the cells can, for example, be proliferated for 1 to 10 days, or for 2 to 8 days, or for 3 to 7 days. In some embodiments, MDCK cells are proliferated for about 3 to about 5 days.

In certain embodiments, the serum-free medium is an enriched serum-free medium as described herein (see Section 0). In one embodiment, the serum-free medium comprises a plant hydrolysate, a lipid supplement, trace elements, and is fortified with one or more medium component selected from the group consisting of putrescine, amino acids, vitamins, fatty acids, and nucleosides. In another embodiment, the serum-free medium comprises all the components of the MediV SFM110 medium listed in Table 2. In a specific embodiment, the serum-free medium consists essentially of all the components of the MediV SFM 110 medium listed in Table 2. In another specific embodiment, the serum-free medium consists of the components listed in Table 2 at the final concentrations indicated. In certain embodiments the serum-free medium comprises glucose at a final concentration of about 4.5 g/L. In other embodiments the serum-free medium comprises glucose at a final concentration of about 9.0 g/L.

Influenza viruses which may be used to infect the cells (step (b)) include, but are not limited to, those that have been described herein (see, e.g., Sections 7.2 and Error! Reference source not found.). The amount of virus to be added to infect the cells (referred to herein as the "viral input") may be measured as the number of virus added per cell (also commonly referred to as the multiplicity of infection, or MOI). In some embodiments, the infection of the cells with virus is carried out using a viral input of about 0.00001 FFU/cell to about 10 FFU/cell, or about 0.00001 FFU/cell to about 1 FFU/cell, or about 0.00001 FFU/cell to about 0.1 FFU/cell, or about 0.00001 FFU/cell to about 0.001 FFU/cell. In one embodiment, the infection of cells with virus is carried out using a viral input of about 0.00001 FFU/cell to about 0.0001 FFU/cell, or about 0.00002 FFU/cell to about 0.0002 FFU/cell. In a specific embodiment, the infection of the cells with virus is carried out using a viral input of between 0.00001 FFU/cell to 0.00005 FFU/cell. In another specific embodiment, the infection of the cells with virus is carried out using a viral input of between 0.0001 FFU/cell to 0.0005 FFU/cell. The following formula may be used to determine the amount of virus to add:

Amount of virus in $\mu L$=Total cells×Viral input(FFU/cell)/$10^{Virus\ FFATiter}$(FFU/mL)×1000.

Alternatively, the amount of virus used to infect the cells (i.e., viral imput) is determined by the final concentration of virus in the culture. For example, virus may be added at a final concentration of about $1 \times 10^3$ FFU/mL to about $0.001 \times 10^3$ FFU/mL, or about $0.1 \times 10^3$ FFU/mL to about $0.01 \times 10^3$ FFU/mL. The following formula may be used to determine the amount of virus to add to achieve the desired final concentration:

Amount of virus in $\mu$=culture volume (mL)×final concentration (FFU/mL)/$10^{Virus\ FFATiter}$(FFU/mL)×1000.

Optionally a protease can be added which brings about the cleavage of the precursor protein of hemagglutinin [$HA_0$] and thus the adsorption of the viruses on the cells. The addition of a protease can be carried out according to the invention shortly before, simultaneously to or shortly after the infection of the cells with influenza viruses. If the addition is carried out simultaneously to the infection, the protease can either be added directly to the cell culture to be infected or, for example, as a concentrate together with the virus inoculate. The protease is, in certain aspects of the invention, a serine protease, or a cysteine protease, or an asparagine protease. In one embodiment, trypsin is used. In a specific embodiment, TPCK-treated trypsin is used. In one embodiment, trypsin is added to the cell culture up to a final concentration of 1 to 5000 mU/ml, or 5 to 1000 mU/ml, or 100 to 500 mU/ml. In an alternative embodiment, trypsin is added to the cell culture up to a final concentration of 1 to 200 µg/ml, or 5 to 50 µg/ml, or 5 to 30 µg/ml in the culture medium.

The protease can be from an animal source, or, more preferably, is from a recombinant source. Recombinant proteases suitable for use are readily obtained from a number of commercial sources including, for example Invitrogen (TrypLE™) and Sigma-Aldrich (TrypZean™), as a stock solution (e.g., 1×-100×). In certain embodiments, a recombinant protease is used at a final concentration of between about 0.01× to about 1×, or between about 0.02× to about 0.8× or between about 0.03× to about 0.7×, or between about 0.04× to about 0.6×, or between about 0.05× to about 0.5×, or between about 0.06× to about 0.4×, or between about 0.07× to about 0.3×, or between about 0.8× and about 0.2×. In a specific embodiment, a recombinant protease is used at a final concentration of between about 0.02× and about 0.06×. In another embodiment, the protease is a recombinant trypsin-like protease, including but not limited to TrypLE™ (Invitrogen). In still another embodiment, the protease is from *Streptomyces griseus* as described in U.S. application Ser. No. 11/455,818.

After infection, the infected cell culture is cultured further to replicate the viruses, in particular until a maximum cytopathic effect or a maximum amount of virus or antigen can be detected. In one embodiment, after infection the cells are cultured at a temperature of between 30° C. and 37° C. In certain embodiments, after infection with viruses the cells are cultured at a temperature of less then 39° C., or less than 38° C., or less than 37° C., or less than 36° C., or less than 35° C., or less than 34° C., or less than 33° C., or less than 32° C., or less than 31° C., or less than 30° C. The culturing of the infected cells at temperatures below 33° C., in particular in the temperature ranges indicated above, leads to the production of higher yields of certain influenza viruses, such as, for example B strains (see, e.g., U.S. Patent Publication 2006/0153872). Furthermore, the culturing of the infected cells at temperatures below 35° C. is contemplated for the production of temperature sensitive, cold adapted (ts/ca) influenza virus. It is contemplated that ts/ca viruses may also be attenuated (att). In another embodiment, the cells are cultured at a temperature of less than 30° C., or of less than 31° C., or of less than 32° C., or of less than 33° C., or of less than 34° C. for the production of ts/ca influenza strains. In a specific embodiment, the cells are cultured at a temperature of 31° C., for the production of influenza virus B strains. In still another embodiment, after infection the cells are cultured at a temperature of 31±2° C.

In certain embodiments, the incubating of the cells (step (c)) is carried out for a sufficient period to produce suitable yields of virus, such as 2 to 10 days, or optionally 3 to 7 days, after infection. In one embodiment of the method, the incubating of the cells (step (c)) is carried out for 2 days, or 3 days, or 4 days, or 5 days, or after 6 days, or 7 days after infection. In other embodiments the incubating of the cells (step (c)) is carried out for 40 to 96 hours after infection. In a specific embodiment, the incubating of the cells (step (c)) is carried out for about 48 to about 72 hours after infection.

In certain embodiments of the method, the cells can, for example, be incubated after infection with viruses (step (b)) such that the agitation rate, pH, $pO_2$ value, $CO_2$ concentration and other parameters are maintained as described supra (see Sections 0 and 0).

In certain embodiments, the method further comprises, after step (c), the step of harvesting the culture medium containing the replicated virus (i.e., the culture medium in which infected cells have been grown). The harvested culture medium containing the replicated virus is also referred to herein as the "viral harvest".

In one embodiment any microcarriers utilized in the propagation of the MDCK cells are allowed to settle prior to harvesting the culture medium containing the replicated virus. Optionally, or alternatively, the culture medium containing the replicated virus can be harvested utilizing a alternating low shear tangential flow (ATF) device, see for example U.S.

Pat. No. 6,544,424. The use of an ATF device can reduce or even eliminate the time needed to let microcarriers settle prior to harvest. In another embodiment, the viral harvest is stabilized with a suitable buffer.

In a specific embodiment, the viral harvest is stabilized by the addition of a concentrated buffer including but not limited to a sucrose phosphate (SP) buffer, which may be added to obtain a final concentration of about 218 mM sucrose, 11 mM phosphate buffer pH 7.0-7.4 in the stabilized viral harvest.

In another specific embodiment, step of harvesting the culture medium containing the replicated virus is coupled to the purification of the replicated viruses. For example, alternating tangential flow (ATF) may be used harvest the culture medium containing the replicated virus and the harvested material may be directly subjected one or more of the purification steps detailed infra.

6.5 Purification of Vaccine Material

The present invention provides robust methods for the purification of viruses, in particular live viruses for clinical use that have been replicated in cell culture. The purification methods of the invention may be used to purify viruses from cultures of mammalian cells including, but not limited to, human diploid lung fibroblast cell lines (e.g., MRC-5 and WI-38), human retinoblastoma cell lines, human kidney cell lines (e.g., PER.C6 and 293), fetal rhesus lung cell lines (e.g., FRhL2), African green monkey kidney cell lines (e.g., Vero), and canine kidney cell lines (e.g., MDCK). The purification methods of the invention give a high overall recovery of virus, in particular live virus and result in levels of host cell DNA (HCD), host cell protein (HCP) and non-specific endonuclease (e.g. Benzonase), which are below the specifications required by regulatory agencies.

Reducing the amount of HCD from virus preparations is particularly important for those viruses that are intended for clinical use in animals (including humans). Furthermore, it is contemplated that the size of any residual HCD should be smaller than the average size of an oncogene (1,925 base pairs) to reduce the oncogenic potential. Accordingly, in one aspect the present invention provides methods for the purification of influenza viruses or RSV that reduce the quantity and size of any residual HCD to levels below that acceptable for injectable vaccines (WHO recommendation is 10 ng per dose for parenterally administered vaccines; Griffiths, 1999, Dev Biol Stand. Basel, Karger, vol 98, pp 153-157.). In another aspect of the present invention methods for the purification of inhaled virus reduce the quantity and size of any residual HCD to levels below 150 ng per dose.

In certain embodiments, the purified viruses comprise less than about 10 ng HCD/dose, or less then about 9 ng HCD/dose, or less then about 8 ng HCD/dose, or less then about 7 ng HCD/dose, or less then about 6 ng HCD/dose, or less then about 5 ng HCD/dose, or less then about 4 ng HCD/dose, or less then about 3 ng HCD/dose, or less then about 2 ng HCD/dose, or less then about 1 ng HCD/dose, or less then about 0.8 ng HCD/dose, or less then about 0.6 ng HCD/dose, or less then about 0.4 ng HCD/dose, or less then about 0.2 ng HCD/dose. In a specific embodiment, the purified viruses comprise less than about 1 ng HCD/dose or less then about 0.8 ng HCD/dose, or less then about 0.6 ng HCD/dose, or less then about 0.4 ng HCD/dose, or less then about 0.2 ng HCD/dose.

In certain embodiments, the purified viruses comprise less than about 200 ng HCD/dose, or less then about 190 ng HCD/dose, or less then about 180 ng HCD/dose, or less then about 170 ng HCD/dose, or less then about 160 ng HCD/dose, or less then about 150 ng HCD/dose, or less then about 140 ng HCD/dose, or less then about 130 ng HCD/dose, or less then about 120 ng HCD/dose, or less then about 110 ng HCD/dose, or less then about 100 ng HCD/dose, or less then about 90 ng HCD/dose, or less then about 80 ng HCD/dose, or less then about 70 ng HCD/dose. In a specific embodiment, the purified viruses comprise less than about 120 ng HCD/dose or less then about 105 ng HCD/dose, or less then about 100 ng HCD/dose, or less then about 90 ng HCD/dose, or less then about 75 ng HCD/dose.

In other embodiments, the purified viruses are influenza viruses and comprise less than about 10 ng HCD/$7.0\pm0.5$ $\log_{10}$FFU, or less then about 9 ng HCD/$7.0\pm0.5$ $\log_{10}$FFU, or less then about 8 ng HCD/$7.0\pm0.5$ $\log_{10}$FFU, or less then about 7 ng HCD/$7.0\pm0.5$ $\log_{10}$FFU, or less then about 6 ng HCD/$7.0\pm0.5$ $\log_{10}$FFU, or less then about 5 ng HCD/$7.0\pm0.5$ $\log_{10}$FFU, or less then about 4 ng HCD/$7.0\pm0.5$ $\log_{10}$FFU, or less then about 3 ng HCD/$7.0\pm0.5$ $\log_{10}$FFU, or less then about 2 ng HCD/$7.0\pm0.5$ $\log_{10}$FFU, or less then about 1 ng HCD/$7.0\pm0.5$ $\log_{10}$FFU, or less then about 0.8 ng HCD/$7.0\pm0.5$ $\log_{10}$FFU, or less then about 0.6 ng HCD/$7.0\pm0.5$ $\log_{10}$FFU, or less then about 0.4 ng HCD/$7.0\pm0.5$ $\log_{10}$FFU, or less then about 0.2 ng HCD/$7.0\pm0.5$ $\log_{10}$FFU. In a specific embodiment, the purified viruses comprise less than about 1 ng HCD/$7.0\pm0.5$ $\log_{10}$FFU or less then about 0.8 ng HCD/$7.0\pm0.5$ $\log_{10}$FFU, or less then about 0.6 ng HCD/$7.0\pm0.5$ $\log_{10}$FFU, or less then about 0.4 ng HCD/$7.0\pm0.5$ $\log_{10}$FFU, or less then about 0.2 ng HCD/$7.0\pm0.5$ $\log_{10}$FFU.

In one embodiment, the amount of HCD is determined using a PicoGreen Assay. In another embodiment, the amount of HCD is determined using a real time polymerase chain reaction (rtPCR). These assays may be performed using methods exemplified in the Example provided in Section 8.3.

In certain embodiments, at least about 50%, or at least about 60%, or at least about 70%, or at least about 80% of the HCD present in the purified viruses is less than about 1000 base pairs (bp) in length. In a specific embodiment, at least about 80% of the HCD present in the purified viruses is less than about 1000 bp in length. In another specific embodiment, about 90% of the HCD present in the purified viruses is less than about 1000 bp in length. In other embodiments, at least about 40%, or at least about 50%, or at least about 60%, or at least about 70%, or at least about 80% of the HCD present in the purified viruses is less than about 500 bp in length. In a specific embodiment, at least about 60% of the HCD present in the purified viruses is less than about 500 bp in length.

In some embodiments, the purified viruses and comprise less than about 100 µg HCP/dose, or less then about 90 µg HCP/dose, or less then about 80 µg HCP/dose, or less then about 70 µg HCP/dose, or less then about 60 µg HCP/dose, or less then about 50 µg HCP/dose, or less then about 40 µg HCP/dose, or less then about 30 µg HCP/dose, or less then about 20 µg HCP/dose, or less then about 10 µg HCP/dose, or less then about 9 µg HCP/dose, or less then about 8 µg HCP/dose, or less then about 7 µg HCP/dose, or less then about 6 µg HCP/dose, or less then about 5 µg HCP/dose, or less then about 4 µg HCP/dose, or less then about 3 µg HCP/dose, or less then about 2 µg HCP/dose, or less then about 1 µg HCP/dose, or less then about 0.8 µg HCP/dose, or less then about 0.6 µg HCP/dose, or less then about 0.4 µg HCP/dose, or less then about 0.2 µg HCP/dose. In a specific embodiment, the purified viruses comprise less than about 1 ng HCP/dose, or less then about 0.8 µg HCP/dose or less then about 0.6 µg HCP/dose, or less then about 0.4 µg HCP/dose, or less then about 0.2 µg HCP/dose.

In other embodiments, the purified viruses are influenza viruses and comprise less than about 10 µg HCP/$7.0\pm0.5$ $\log_{10}$FFU, or less then about 9 µg HCP/$7.0\pm0.5$ $\log_{10}$FFU, or less then about 8 µg HCP/$7.0\pm0.5$ $\log_{10}$FFU, or less then about 7 μg HCP/7.0±0.5 log$_{10}$FFU, or less then about 6 μg HCP/7.0±0.5 log$_{10}$FFU, or less then about 5 μg HCP/7.0±0.5 log$_{10}$FFU, or less then about 4 μg HCP/7.0±0.5 log$_{10}$FFU, or less then about 3 μg HCP/7.0±0.5 log$_{10}$FFU, or less then about 2 μg HCP/7.0±0.5 log$_{10}$FFU, or less then about 1 μg HCP/7.0±0.5 log$_{10}$FFU, or less then about 0.8 μg HCP/7.0±0.5 log$_{10}$FFU, or less then about 0.6 μg HCP/7.0±0.5 log$_{10}$FFU, or less then about 0.4 μg HCP/7.0±0.5 log$_{10}$FFU, or less then about 0.2 μg HCP/7.0±0.5 log$_{10}$FFU. In a specific embodiment, the purified viruses comprise less than about 1 ng HCP/7.0±0.5 log$_{10}$FFU, or less then about 0.8 μg HCP/7.0±0.5 log$_{10}$FFU or less then about 0.6 μg HCP/7.0±0.5 log$_{10}$FFU, or less then about 0.4 μg HCP/7.0±0.5 log$_{10}$FFU, or less then about 0.2 μg HCP/7.0±0.5 log$_{10}$FFU.

In one embodiment, the amount of HCP is determined by an Enzyme-Linked Immunosorbent Assay (ELISA) using an antibody against HCP for detection. This assay may be performed using methods exemplified in the Example provided in Section 8.3.

Methods for the preparation of inactive/disintegrated virus particles for vaccine compositions are well known in the art and have been utilized for over 40 years. However, these methods incorporate harsh steps, such as treatment with detergents or formaldehyde, which cannot be generally utilized for the preparation of intact virus particles and, live attenuated viruses in particular. Accordingly, the present invention provides methods for the purification of live intact viruses (e.g., influenza viruses or RSV) utilizing membranes and conditions to adequately separate HCD and HCP from the viral harvest. The methods of the present invention give a high overall recovery of live virus. In one embodiment, the overall recovery of purified viruses is at least 3%, or at least 5%, or at least 10%, or at least 15%, or at least 20%, or at least 25%, or at least 30%, or at least 40%, or at least 50%, or at least 60%, or at least 70%. Methods to monitor the recovery of purified live virus include assays designed to measure viral infection and/or growth. For example, Focal Fluorescent Assays and Median Tissue Culture Infectious Dose (TCID$_{50}$) Assays can be used to monitor the recovery of purified live influenza virus. In certain embodiments, the method of purification of viruses of the instant invention gives an overall recovery of viruses of at least 30%, wherein the purified viruses comprise less than 0.1 ng HCD, and less than 0.3 μg HCP, and less than 0.0050 ng non-specific nuclease per 7.0±0.5 log$_{10}$ FFU of virus.

The purification of virus harvest contains multiple steps, which can be optimized depending on the virus and purification conditions. In certain embodiments, the purification process may comprise anyone of the following, alone or in combination, a) clarification of viral harvest; b) concentration and/or buffer exchange; c) purification by chromatography and d) sterile filtration. These steps may comprise further steps such as treatment with a non-specific endonuclease and stabilization of the viral harvest or viral load. These steps may be performed multiple times in the purification process and in an order that maximizes the viral recovery while adequately removing HCP and HCD, as described above.

Methods useful for the clarification of a viral harvest include, but are not limited to, centrifugation, dialysis, and membrane filtration, which includes, but is not limited to, methods such as single pass, dead-end, direct flow filtration (DFF) in which liquid flows directly through the filter medium, and crossflow or tangential flow filtration (TFF) in which liquid flows tangential to (along) the surface of the membrane. TFF systems may be run so as to maintain a constant Filtrate Flux rate (often referred as simply "Flux" and which may be measured as liters of permeate per square meter of membrane per hour (LMH)) or to maintain a constant transmembrane pressure (abbreviated as "TMP" which may be measured as pounds per square inch (psi)). However, either constant Flux and the TMP may be regulated to prevent membrane fouling. Membranes for use in filtration applications are available from commercial sources.

Within the art, there are four commonly accepted categories of membranes defined by the size of the material they remove from the carrier liquid. They are, from the smallest to largest pore size are reverse osmosis membranes, nanofiltration membranes, ultrafiltration membranes, and microfiltration membranes. Filtration with the above-mentioned membranes separates molecules according to their molecular weight by using membranes with specific pore sizes. For example, separation with reverse osmosis membranes that have pore sizes less than 0.001 micrometers is intended to separate molecules that have a molecular weight less than 200 Daltons. Filtration with nanofiltration membranes that have pore sizes from 0.001-0.008 micrometers, inclusive, is intended to separate molecules that have a molecular weight from 200 Daltons to 15 kilodaltons (kDa) inclusive. Filtration with ultrafiltration membranes that have pore sizes from 0.005-0.1 micrometers, inclusive, is intended to separate molecules that have a molecular weight from 5 kDa-300 kDa, inclusive. Filtration with microfiltration membranes that have pore sizes from 0.05-3.0 micrometers, inclusive, is intended to separate molecules that have a molecular weight from 100 kDa-3000 kDa and larger. Accordingly, membrane-filtration can separate molecules of interest (e.g., viruses) from other cellular components based on size exclusion by utilizing membranes that have a particular Molecular Weight Cut-Off (MWCO) that is determined by the pore size of the membrane. The MWCO, also called Nominal Molecular Weight Limit (NMWL) or Nominal Molecular Weight Cut-Off (NM-WCO), is the kilodalton size designation for the filtration by membranes. The MWCO is defined as the molecular weight of the molecule that is 90% retained by the membrane. Because, for example, molecules of the same molecular weight can have significantly different shapes, the MWCO is not an exact metric, but is nevertheless a useful metric and is commonly employed by filter manufacturers. Membranes may be used as flat sheets or in a spirally wound configuration. Hollow fibers may also be used depending on the type of filtration method. Any number of potential membrane materials may be used including, but not limited to, regenerated cellulose, polyether sulfone (which may or may not be modified to alter its inherent hydrophobicity), polyvinylidene fluoride (PVDF), and ceramic and metal oxide aggregates, as well as polycarbonate, polypropylene, polyethylene and PTFE (TEFLON®). It is contemplated that combinations of filtration methods and membrane types may be used in separation and that the capacity of the filters, columns, etc., comprising separation membranes will be adjusted depending on the volume and/or concentration of material being processed.

Methods useful for concentrating and/or buffer exchange include, but are not limited to, dialysis, ultrafiltration (UF) and diafiltration (DF). TFF can incorporate both UF, which can be used to concentrate, and DF, which can be used to exchange buffers. Furthermore, the use of UF and/or DF may result in additional purification by the fractionation process that washes smaller molecules, which may be contaminants, through a membrane and leaves larger molecules of interest in the retentate. Accordingly, TFF, incorporating UF and/or DF may be used to concentrate and/or exchange buffers and/or purify. The choice of membranes for use in filtration applications has been described supra. According to the invention, DF can be either discontinuous or continuous DF. In discontinuous DF, the solution is concentrated, and the lost volume is replaced by a new buffer. In continuous DF, the solution volume is maintained by the inflow of new buffer solution while the old buffer solution is removed.

In certain embodiments, the clarified virus is concentrated about 2×, or about 3×, or about 4×, or about 5×, or about 6×, or about 7×, or about 8×, or about 9×, or about 10×, or more, wherein "×" equals the Total starting volume added to the operation/final retentate volume. In a specific embodiment, the clarified virus is concentrated between about 3× to about 5×. In another specific embodiment, the clarified virus is concentrated about 4×, wherein "×" equals the Total starting volume added to the operation/final retentate volume. In certain embodiments, the clarified virus is concentrated about 10× or more to increase the loading of all subsequent purification steps. In certain embodiments, following concentration about 1 diavolume, or about 2 diavolumes, or about 3 diavolumes, or about 4 diavolumes, or about 5 diavolumes, or about 6 diavolumes, or about 7 diavolumes, or about 8 diavolumes, or about 9 diavolumes or about 10 diavolumes, or more diavolumes of buffer are exchanged by DF, wherein a diavolume is the total buffer volume introduced to the operation during DF/retentate volume. In a specific embodiment, between about 4 diavolumes to about 6 diavolumes of buffer are exchanged wherein a diavolume is the total buffer volume introduced to the operation during DF/retentate volume. In another specific embodiment, about 5 diavolumes of buffer are exchanged, wherein a diavolume is the total buffer volume introduced to the operation during DF/retentate volume.

In certain embodiments, the retentate, comprising viruses (e.g., influenza, RSV), is collected after the desired volume of buffer is exchanged. After collection of the retentate some virus may remain weakly bound to the membrane. Accordingly, in some embodiments, the membrane is rinsed with additional exchange buffer which is added to the collected retentate. The collected retentate is also referred to herein as "conditioned viral load" or as the "#XUF #XDF" where "#" indicates either the fold concentration or the number of diavolumes of buffer exchanged for the UF and DF processes, respectively. In a specific embodiment, a membrane with a 500 kDa MWCO is used for the concentration and buffer exchange. In some embodiments, the membrane may be cleaned post process and reused. In other embodiments, a new membrane is used for each batch of clarified virus. In another specific embodiment, the clarified harvest is concentrated and the buffer exchanged as exemplified in the Examples provided in Sections 8.3 and 8.4.

Types of chromatography useful for the purification of viruses (e.g., influenza or RSV) include, but are not limited to, affinity chromatography as well as ion-exchange chromatography and/or hydroxyapatite chromatography. In certain embodiments, ion exchange chromatography is used. In one embodiment, cation exchange chromatography is used. In another embodiment, cation exchange chromatography is performed at high pH. In one embodiment, anion exchange chromatography is used. In a specific embodiment, a strong quaternary ammonium (Q) anion exchanger is used (e.g. Capto™ Q, GE Healthcare) In another embodiment, anion exchange chromatography is performed at low pH. Anion media useful for ion exchange chromatography include, but are not limited to, anion membrane adsorbers (e.g., Sartobind® Q15, D15) and cation membrane adsorbers (e.g., Sartobind® S15 and C15). In another embodiment, negative chromatography is used wherein the impurities are bound by anion or cation-exchange and virus is subsequently separated or purified from the impurities such as host cell protein and/or nucleic acid. It is contemplated that the chromatography can be performed in a batch process or alternatively utilizing a column process. In certain embodiments, the conditioned viral load is purified by column chromatography.

Methods useful for the efficient removal of contaminating HCD include, along with the other steps of the purification process, treatment with a non-specific endonuclease (e.g., Benzonase®). However, for those viruses that are intended for clinical use in animals (including humans) it is desirable that the amount of non-specific endonuclease in the final purified viruses be minimal. Accordingly, in another aspect the present invention provides methods for the purification of viruses that reduce the quantity any residual non-specific endonuclease used in the method to levels below that acceptable for injectable vaccines.

In one embodiment, the purified viruses comprise less than about 0.0060 ng, or less then about 0.0055 ng, or less then about 0.0050 ng, or less then about 0.0045 ng, or less then about 0.0040 ng, or less then about 0.0035 ng, or less then about 0.0030 ng, or less then about 0.0025 ng, or less then about 0.0020 ng, or less then about 0.0015 ng, or less then about 0.0010 ng, or less of non-specific endonuclease per dose. In a specific embodiment, the purified viruses comprise less than about 0.0040 ng, or less then about 0.0035 ng, or less then about 0.0030 ng, or less then about 0.0025 ng of non-specific endonuclease per dose.

In other embodiments, the purified viruses are influenza viruses or RSV and comprise less than about 0.0060 ng, or less then about 0.0055 ng, or less then about 0.0050 ng, or less then about 0.0045 ng, or less then about 0.0040 ng, or less then about 0.0035 ng, or less then about 0.0030 ng, or less then about 0.0025 ng, or less then about 0.0020 ng, or less then about 0.0015 ng, or less then about 0.0010 ng, or less of non-specific endonuclease per $7.0\pm0.5$ $\log_{10}$FFU. In a specific embodiment, the purified viruses are influenza viruses or RSV and comprise less than about 0.0040 ng, or less then about 0.0035 ng, or less then about 0.0030 ng, or less then about 0.0025 ng of non-specific endonuclease per $7.0\pm0.5$ $\log_{10}$FFU. In another specific embodiment, the purified viruses are RSV and comprise less than about 0.009 ng, or less then about 0.01 ng, or less then below level of detection (0.1 ng/mL with ELISA) non-specific endonuclease per $5.0\pm0.5$ $\log_{10}$FFU. In yet another specific embodiment, the non-specific endonuclease is Benzonase®.

Sterility is of particular importance for those viruses and/or viral components that are intended for clinical use in animals (including humans). Accordingly, the methods for the purification of viruses (e.g., influenza or RSV) of the present invention incorporate sterilization, which can be performed as a terminal filtration step (e.g., RSV) or using know sterilization methods (e.g., Influenza virus). Methods useful for the sterilization of vaccine components (e.g., viruses, delivery devices, etc.) include, but are not limited to, irradiation, filtration, chemical treatment, and other suitable procedures. In one embodiment, the formulated virus bulk is sterilized by filtration. Filtration methods useful for sterilization include, but are not limited to, single pass, dead-end, direct flow filtration (DFF) and tangential flow filtration (TFF), which have been described supra. However, due to the fragile nature of RSV the virus can not be sterilized using a sterilization grade filter.

Herein are provided specific methods for purifying influenza virus and RSV for vaccine formulation.

6.5.1 Purification of Influenza Viruses

In certain embodiments, the viruses to be purified are influenza viruses (e.g., cold-adapted, and/or temperature sensitive, and/or attenuated).

In one embodiment the method of purifying viruses from cell culture comprises the following steps:

(a) clarification of a viral harvest;
(b) concentration and/or buffer exchange following step (a);
(c) purification by chromatography following step (b);
(d) concentration and/or buffer exchange following step (c); and
(e) sterilization following step (d).

In one embodiment, the viruses are influenza viruses. In a specific embodiment, the influenza viruses are cold-adapted, and/or temperature sensitive, and/or attenuated influenza viruses.

In a specific embodiment, steps (a), (b), (d) and (e) are performed by membrane filtration. In another specific embodiment, steps (b) and (d) are performed by tangential flow filtration. In still another specific embodiment, steps (a) and (e) are performed by direct flow filtration. In yet another specific embodiment, step (b) includes both concentration by ultrafiltration and buffer exchange by diafiltration. In still another specific embodiment, step (d) includes only concentration. Additional embodiments of the method of purifying viruses are detailed infra.

In one specific embodiment, step (c) is performed by affinity column chromatography. In another specific embodiment, step (c) further incorporates treatment with a non-specific nuclease.

As described supra, viruses obtained from cell culture may be stabilized (e.g., by the addition of a sucrose phosphate (SP)), after harvest. Accordingly, the purification methods of the present invention encompass the clarification of a stabilized viral harvest. Alternatively, the steps of harvesting and clarification may be coupled. For example, ATF may be used to harvest cell culture replicated virus and pump the viral harvest directly to the media and/or device used for clarification of the virus.

For example, crude medium from infected cultures can first be clarified by centrifugation at, e.g., 1000-2000×g for a time sufficient to remove cell debris and other large particulate matter, e.g., between 10 and 30 minutes. Alternatively, the medium is filtered through a semi-permeable membrane of a defined range of pore sizes large enough to allow passage of the virus while retaining intact cells and other large particulate matter.

In one embodiment, the viral harvest is clarified by DFF and/or TFF using a MF membrane having a pore size large enough for the virus to pass through but small enough to retain intact cells and cellular debris. In one embodiment, the viral harvest is clarified by DFF and/or TFF through at least one membrane having a pore size of about 1.2 micrometers or less. In a specific embodiment, the viral harvest is clarified by DFF through at least one membrane having a pore size of between about 1.2 micrometers to about 0.45 micrometers. In another specific embodiment, the viral harvest is clarified by DFF through a first membrane have a pore size of 1.2 micrometers and a second membrane having a pore size of 0.45 micrometers. In certain embodiments, polypropylene and/or PVDF membranes are used. In still another specific embodiment, the viral harvest is clarified by DFF as exemplified in the Example provided in Section 8.3. In yet another specific embodiment, the harvesting of the cell culture replicated virus is coupled to the DFF step. For example, the cell culture replicated virus is harvested and applied directly to the media and device used for DFF. The coupling of the harvest and clarification steps reduces the number of manipulations, avoids the need for a harvest tank and reduces overall processing time.

In one embodiment, the clarified harvest is concentrated and/or the buffer is exchanged. In one embodiment, concentration and/or buffer exchange is performed by UF and DF. In another embodiment, TFF is used for both the UF and DF. In yet another embodiment, the harvesting of the cell culture replicated virus is coupled to the DFF step which is coupled to the TFF step. The coupling of the harvest, clarification and concentration/buffer exchange steps reduces the number of manipulations, and reduces overall processing time. In certain embodiments, the TFF is run so as to maintain a constant Filtrate Flux rate. In other embodiments, the TFF is run so as to maintain a constant TMP. In certain embodiments, the clarified virus is first concentrated by UF and then the buffer is exchanged by DF. It is contemplated that the exchange buffer may be the same or different from that present in the viral harvest. In one embodiment, the exchange buffer is an SP buffer at a neutral pH. In a specific embodiment, the exchange buffer comprises (within 10% variation of one or more component) 218 mM sucrose, 11 mM phosphate buffer pH 7.0-7.4. In another specific embodiment, the exchange buffer consists (within 10% variation of one or more component) of 218 mM sucrose, 11 mM phosphate buffer, pH 7.0-7.4. In certain embodiments, the retentate, comprising viruses (e.g., influenza), is collected after the desired volume of buffer is exchanged. After collection of the retentate some virus may remain weakly bound to the membrane. Accordingly, in some embodiments, the membrane is rinsed with additional exchange buffer which is added to the collected retentate. The collected retentate is also referred to herein as "conditioned viral load" or as the "#XUF #XDF" where "#" indicates either the fold concentration or the number of diavolumes of buffer exchanged for the UF and DF processes, respectively. In a specific embodiment, a membrane with a 500 kDa MWCO is used for the concentration and buffer exchange. In some embodiments, the membrane may be cleaned post process and reused. In other embodiments, a new membrane is used for each batch of clarified virus. In another specific embodiment, the clarified harvest is concentrated and the buffer exchanged as exemplified in the Examples provided in Sections 8.3 and 8.4.

In certain embodiments, the conditioned viral load is purified by chromatography. In some embodiments, the conditioned viral load is purified by affinity chromatography. A variety of affinity chromatography media are available with similar separation properties, for example numerous affinity chromatography media are available for the concentration and purification of a number of viruses and viral proteins, including, but not limited to N(p-Aminophenyl)oxamic acid agarose, Cellufine™ Sulfate, In a specific embodiment, Cellufine™ Sulfate (Chisso Corp.) affinity media is utilized for affinity chromatography. In another embodiment, FluSelect™ (GE Healthcare) is utilized for affinity chromatography. In certain embodiments, the conditioned viral load is loaded directly onto an affinity media. In certain embodiments the unbound material may be passed over the affinity media to facilitate the binding of additional viruses.

In one embodiment, between about $10^{9.0}$ to about $10^{1.0}$, or between about $10^{9.2}$ to about $10^{9.8}$, or between about $10^{9.4}$ to about $10^{9.6}$ virus particles, are loaded per ml of affinity media. In another embodiment, at least about $10^{9.0}$, or at least about $10^{9.1}$, or at least about $10^{9.2}$, or at least about $10^{9.3}$, or at least about $10^{9.4}$, or at least about $10^{9.5}$, or at least about $10^{9.6}$, or at least about $10^{9.7}$, or at least about $10^{9.9}$, or at least about $10^{9.9}$ virus particles are loaded per mL of affinity media. In certain embodiments, the virus particles are live viruses. Methods for determining the number of lives virus in a sample are described herein.

In another embodiment, between about 9.0 $\log_{10}$FFU to about 10 $\log_{10}$FFU, or between about 9.2 $\log_{10}$FFU to about 9.8 $\log_{10}$FFU, or between about 9.4 $\log_{10}$FFU to about 9.6 $\log_{10}$FFU of virus, are loaded per mL of affinity media. In another embodiment, at least about 9.0 $\log_{10}$FFU, or at least about 9.1 $\log_{10}$FFU, or at least about 9.2 $\log_{10}$FFU, or at least about 9.3 $\log_{10}$FFU, or at least about 9.4 $\log_{10}$FFU, or at least about 9.5 $\log_{10}$FFU, or at least about 9.6 $\log_{10}$FFU, or at least about 9.7 $\log_{10}$FFU, or at least about 9.8 $\log_{10}$FFU, or at least about 9.9 $\log_{10}$FFU of virus are loaded per mL of affinity media. In a specific embodiment, Cellufine™ Sulfate (Chisso Corp.) affinity media is utilized and between 9.2 $\log_{10}$FFU to 9.8 $\log_{10}$FFU of virus are loaded per mL of Cellufine™ Sulfate. In another specific embodiment, Cellufine™ Sulfate (Chisso Corp.) affinity media is utilized and between 9.4 $\log_{10}$FFU to 9.6 $\log_{10}$FFU of virus are loaded per mL of Cellufine™ Sulfate. In still another specific embodiment, Cellufine™ Sulfate (Chisso Corp.) affinity media is utilized and at least about 9.4 $\log_{10}$FFU, or at least about 9.5 $\log_{10}$FFU, or at least about 9.6 $\log_{10}$FFU, or at least about 9.7 $\log_{10}$FFU of virus are loaded per mL of Cellufine™ Sulfate.

In one embodiment the affinity media is washed, with a sufficient volume of buffer in which the viruses will remain bound to the affinity media (e.g., an SP buffer), to remove unbound and weakly bound contaminates from the affinity media. In certain embodiments, the wash buffer comprises (within 10% variation of one or more component) 218 mM sucrose, 11 mM phosphate buffer pH 7.0-7.4. In another specific embodiment, the wash buffer consists of (within 10% variation of one or more component) 218 mM sucrose, 11 mM phosphate buffer pH 7.0-7.4. In certain embodiments, the viruses are eluted from the affinity media after washing, using a sufficient volume of a buffer in which the viruses will not bind to the affinity resin to elute the virus without releasing any contaminants bound to the column, and collected. In certain embodiments, the elution buffer comprises salt. Salts useful for the elution of viruses (e.g., influenza) from affinity columns include sodium chloride, potassium chloride, ammonium chloride, magnesium chloride, and calcium chloride. Generally, the elution buffer is applied to the resin as either a gradient or step in the 0 to 1.0M concentration range. The effectiveness of the cation and anion used as the salts in the elution buffer correlate with the Hofmeister series, where the order of displacement for commonly used cations is: $Ca^+>Mg^{2+}>Na^+>K^+>NH_4^+$ and the order of displacement effectiveness for commonly used anions: $PO_4^{3-}>SO_4^{2-}>COO^->Cl^-$. In one embodiment, the elution buffer comprises (within 10% variation) sodium chloride at a final concentration of 1M. In another embodiment, the elution buffer comprises (within 10% variation of one or more component) 1 M sodium chloride, 218 mM sucrose, and 11 mM phosphate buffer pH 7.0-7.4. The collected eluted virus is also referred to herein as the "purified virus eluate." The elution of the viruses can be monitored by monitoring ultraviolet (UV) absorbance, in particular by monitoring the absorbance at 280 nanometers. In some embodiments, the conditioned viral load is purified by column chromatography, wherein the elution of the viruses is monitored and specific fractions comprises viruses are collected. Such an approach can be useful when it is desirable to minimize the volume of the eluted virus. In another specific embodiment, the conditioned viral load is purified by chromatography as exemplified in the Example provided in Section 8.3.

In certain embodiments, the method of purifying viruses (e.g., influenza) includes treatment with a non-specific endonuclease (e.g., Benzonase®). In certain embodiments, the non-specific endonuclease treatment occurs early in the purification of viruses. In one embodiment, non-specific endonuclease treatment occurs after step (a) but before step (b). In another embodiment, non-specific endonuclease treatment occurs after step (b) but before step (c). Alternatively, the virus is treated with a non-specific endonuclease during step (c). The advantages of this approach are exemplified in the Example provided in Section 8.3. In a specific embodiment, the conditioned viral load is bound to an affinity media and then is exposed to a buffer comprising a non-specific endonuclease. In some embodiments the non-specific endonuclease is present in the buffer at a concentration of between about 10 U/mL and about 100 U/mL. In other embodiments, the non-specific endonuclease is present in the buffer at a concentration of between about 40 U/mL to about 60 U/mL. In one embodiment, the non-specific endonuclease is present in a buffer comprising sucrose. In a specific embodiment, the non-specific endonuclease is present in a buffer comprising 218 mM sucrose, 11 mM phosphate buffer pH 7.0-7.4. In another specific embodiment, the specific endonuclease is present, at a final concentration of between about 40 U/mL to about 60 U/mL, in a buffer consisting of (within 10% variation of one or more component) 218 mM sucrose, 11 mM phosphate buffer pH 7.0-7.4. In certain embodiments, the loading and wash conditions are adjusted to ensure that the bound virus will be exposed to the non-specific endonuclease for between about 10 minutes to about 120 minutes. In one embodiment, the loading and wash conditions are adjusted to ensure that the bound virus will be exposed to the non-specific endonuclease for between about 40 minutes to about 80 minutes. In still other embodiments, the loading and wash conditions are adjusted to ensure that the bound virus will be exposed to the non-specific endonuclease for at least 10 minutes, or at least 20 minutes, or at least 30 minutes, or at least 40 minutes, or at least 50 minutes, or at least 60 minutes, or at least 70 minutes, or at least 80 minutes, or at least 90 minutes, or at least 100 minutes, or at least minutes, or at least 110 minutes, or at least 120 minutes. In certain aspects of the invention, the time of exposure to the non-specific endonuclease, the concentration of the non-specific endonuclease and the volume of non-specific endonuclease containing buffer can be adjusted. For example, to minimize the time needed to cleave DNA contaminates the concentration of non-specific endonuclease may be increased; alternatively to minimize the amount of non-specific endonuclease utilized the time of exposure may be increased. Following treatment with a non-specific endonuclease it may be desirable to wash the affinity media with a sufficient volume of buffer in which the viruses will remain bound to the affinity media (e.g., an SP buffer) to remove any residue digested DNA contaminates. Accordingly, in certain embodiments, the affinity resin is washed as described supra before and/or after treatment with a non-specific endonuclease. In another specific embodiment, the non-specific endonuclease is Benzonase®. In still another specific embodiment, the conditioned viral load is treated with Benzonase® at the same time as purification by affinity chromatography as exemplified in the Example provided in Section 8.3.

In certain aspects of the invention, following purification by chromatography the purified virus eluate is concentrated and/or the buffer is exchanged. Methods useful for concentrating and/or buffer exchange have been described supra. In certain embodiments, the buffer of the purified virus eluate is exchanged using DF. In one embodiment, more than about 5 diavolumes of buffer are exchanged by DF, wherein a diavolume is the total buffer volume introduced to the operation during DF/retentate volume. The advantages of exchanging more than about 5 diavolumes are detailed in the Example provided in Section 8.3. In another embodiment, about 6 diavolumes, or about 7 diavolumes, or about 8 diavolumes, or about 9 diavolumes or about 10 diavolumes, or more diavolumes of buffer are exchanged by DF, wherein a diavolume is the total buffer volume introduced to the operation during DF/retentate volume. In a specific embodiment, about 8 diavolumes, or more diavolumes of buffer are exchanged by DF, wherein a diavolume is the total buffer volume introduced to the operation during DF/retentate volume. In a specific embodiment, the exchange buffer comprises (within 10% variation of one or more component) 200 mM sucrose, 100 mM phosphate buffer pH 7.0-7.4. In another specific embodiment, the exchange buffer consists (within 10% variation of one or more component) of 200 mM sucrose, 100 mM phosphate buffer, pH 7.0-7.4. In certain embodiments, the retentate, comprising viruses, is collected after the desired volume of buffer is exchanged. After collection of the retentate some virus may remain weakly bound to the membrane. Accordingly, in some embodiments, the membrane is rinsed with additional exchange buffer which is added to the collected retentate. The collected retentate is also referred to herein as "formulated virus bulk" or as the "#XDF," where "#" indicates number of diavolumes of buffer exchanged during a DF process, respectively. In a specific embodiment, a membrane with a 500 kDa MWCO is used for the concentration and/or buffer exchange. In some embodiments, the membrane may be cleaned post process and reused. In other embodiments, a new membrane is used for each batch of purified virus eluate. In another specific embodiment, the buffer of the purified virus eluate is exchanged as exemplified in the Example provided in Section 8.3. In still other embodiments, the clarified virus is concentrated by UF and the buffer is exchanged by DF as described supra. The incorporation of an UF step will decrease the volume of the resulting formulated virus bulk. In certain embodiments, the virus eluate is concentrated about 2x, or about 3x, or about 4x, or about 5x, or more, wherein "x" equals the Total starting volume added to the operation/final retentate volume. In other embodiments, the virus eluate is concentrated between 2x and 4x. In a specific embodiment, the virus eluate is concentrated about 2x and then the buffer is exchanged by DF as described supra. In a specific embodiment, the buffer of the purified virus eluate is concentrated and the buffer exchange as exemplified in the Example provided in Section 8.4.

In one embodiment, the formulated virus bulk is sterilized by DFF and/or TFF. In another embodiment, the formulated virus bulk is sterilized using a MF membrane having a pore size large enough for the virus to pass through but small enough to retain other contaminants. In one embodiment, the formulated virus bulk is sterilized by DFF and/or TFF through at least one membrane having a pore size of about 0.45 micrometers. In certain embodiments, polypropylene and/or PVDF membranes are used. In one embodiment, additional components are added to the formulated virus bulk prior to sterilization. In certain embodiments, at least one component selected from the group consisting of amino acid excipients (e.g., glutamate, arginine), protein hydrolysate (e.g., collagen, gelatin), chelating agents (e.g., EDTA) and preservatives is added to the formulated virus bulk prior to sterilization. In a specific embodiment, glutamate, arginine and gelatin are added to the formulated virus bulk prior to sterilization. In another specific embodiment, cGAG (200 mM sucrose, 100 mM phosphate, 12.1% w/v arginine, 10% gelatin and 54 mM or 0.9% glutamate) is added to the purified virus bulk in a ratio of 1:9 v/v. In another specific embodiment, monosodium glutamate, arginine and gelatin are added to the formulated virus bulk prior to sterilization at a final concentration (within 10% variation) of 5.4 mM or 0.09%, 1.21% w/v, and 1. % w/v, respectively. In still another specific embodiment, the formulated virus bulk is sterilized by DFF as exemplified in the Example provided in Section 8.3.

In a specific embodiment, the method of purifying influenza viruses from cell culture comprises the following steps:
(a) clarification of a viral harvest by direct flow filtration (DFF) through at least one membrane having a pore size of between about 1.2 micrometers to about 0.45 micrometers;
(b) concentration by tangential flow ultrafiltration (UF) and buffer exchange by diafiltration (DF) following step (a) using a membrane having 500 kDa molecular weight cut off (MWCO);
(c) purification by affinity column chromatography following step (b);
(d) buffer exchange by DF following step (c) using a membrane having 500 kDa molecular weight cut off (MWCO); and
(e) sterilization following step (d) by DFF through at least one membrane having a pore size of between about 0.45 micrometers to about 0.22 micrometers, wherein overall recovery of purified viruses of at least 30%, and wherein the purified viruses comprise less than 0.1 ng HCD, and less than 0.3 µg HCP per 7.0±0.5 $\log_{10}$FFU of virus.

Additional parameters that may be incorporated in the method of purifying viruses from cell culture, in particular influenza viruses are exemplified in the Example provided in Section 8.3 below.

6.5.2 Purification of RSV

In a specific embodiment, the viruses to be purified are respiratory syncitial viruses (RSV) (e.g., rA2cp248/404/1030ΔSH).

In one embodiment the method of purifying viruses from cell culture comprises the following steps:
(a) clarification of a viral harvest;
(b) stabilization and/or buffer exchange following step (a);
(c) concentration and/or buffer exchange following step (b);
(d) purification by chromatography following step (c); and
(e) terminal filtration following step (d).

In a specific embodiment, step (a) includes multiple filtration steps. In another specific embodiment, step (a) further incorporates treatment with a non-specific endonuclease. In another specific embodiment, steps (a) and (c) are performed by direct flow filtration. In another specific embodiment, step (c) is performed by tangential flow filtration. In yet another specific embodiment, step (c) includes both concentration by tangential flow filtration and buffer exchange by diafiltration. In one specific embodiment, step (d) is performed by ion exchange chromatograph (e.g. cation-exchange). In still another embodiment, step (c) includes only concentration. Additional embodiments of the method of purifying viruses (e.g., RSV) are detailed infra.

The purification methods of the present invention encompass the clarification (step (a)) of a viral harvest. The crude medium from infected cultures can first be clarified by centrifugation at, e.g., 1000-2000×g for a time sufficient to remove cell debris and other large particulate matter, e.g., between 10 and 30 minutes. Alternatively, the supernatant containing the virus is filtered through a series of semi-permeable membranes of a defined range of pore sizes large enough to allow passage of the virus while retaining intact cells and other large particulate matter. This clarification step in the purification process may include the treatment with a non-specific endonuclease (e.g. Benzonase) to degrade cell host DNA wherein the viral harvest is i) filtered by direct flow filtration (DFF); ii) treated with a non-specific endonuclease; and iii) filtered again by DFF.

In one embodiment, the viral harvest is clarified by DFF and/or TFF using a MF membrane having a pore size large enough for the virus to pass through but small enough to retain intact cells and cellular debris. In certain embodiments, the viral harvest is clarified by DFF in combination with treatment of a non-specific endonuclease. In a specific embodiment the viral harvest is filtered through at least one membrane having a pore size of about 10 micrometers or less, followed by treatment with a non-specific endonuclease and then filtered again through at least one membrane having a pore size of about 3.0 micrometers or less. In a specific embodiment, the first filter step in the clarification process is through at least one membrane having a pore size of between about 5.0 micrometers to about 1.0 micrometers. In a specific embodiment, the second filter step in the clarification process is through at least one membrane having a pore size of between about 3.0 micrometers to about 0.45 micrometers. In certain embodiments the first or second filter step, alone or in combination, use a dual membrane filter, wherein two filters of different sizes are stacked to prevent the clogging of the filter with the smaller pore size. In one embodiment this dual filter is about 3/0.8 micrometers in size, wherein the 3 micrometer filter acts as a prefilter to remove larger cellular debris. In another specific embodiment, the viral harvest is clarified by DFF through a first membrane having a pore size of about 3.0 micrometers and a second membrane having a pore size of about 3/0.8 or about 0.65 micrometers.

In certain embodiments, the method of purifying viruses (e.g., RSV) includes treatment with a non-specific endonuclease (e.g., Benzonase®) to degrade the host cell DNA (HCD). In certain embodiments, the non-specific endonuclease treatment occurs early in the purification of viruses. In one embodiment, the virus is treated with a non-specific endonuclease during step (a). In a specific embodiment, the filtered viral harvest is mixed with a buffer comprising a non-specific endonuclease. In some embodiments the non-specific endonuclease is present in the buffer at a concentration of between about 5 U/mL and about 100 U/mL. In other embodiments, the non-specific endonuclease is present in the buffer at a concentration of between about 5 U/mL to about 60 U/mL. In a specific embodiment the non-specific endonuclease is present at about 50 U/mL. In another specific embodiment the non-specific endonuclease is present at about 10 U/mL. In one embodiment, the non-specific endonuclease is present in a buffer comprising about 1.0 mM to about 10 mM $MgCl_2$. In a specific embodiment, the buffer comprises 50 U/mL of a non-specific endonuclease and 5 mM of $MgCl_2$. In another specific embodiment, the $MgCl_2$ is present at 2 mM. In yet another specific embodiment, the buffer comprises 10 U/mL of a non-specific endonuclease and 5 mM of $MgCl_2$.

Following the first filter step in the clarification process, the non-specific endonuclease is incubated with the filtered viral harvest for about 1 hour to about 4 hours at about 32° C.±3. In a specific embodiment the non-specific endonuclease is incubated with the viral harvest for about 3 hours at 32° C. In still other embodiments, the non-specific endonuclease is incubated under conditions adjusted to ensure that the virus will be exposed to the non-specific endonuclease for at least 10 minutes, or at least 20 minutes, or at least 30 minutes, or at least 40 minutes, or at least 50 minutes, or at least 60 minutes, or at least 70 minutes, or at least 80 minutes, or at least 90 minutes, or at least 100 minutes, or at least minutes, or at least 110 minutes, or at least 120 minutes, or at least 150 minutes, or at least 180 minutes, or at least 210 minutes, or at least 240 minutes. In certain aspects of the invention, the time of exposure to the non-specific endonuclease, the concentration of the non-specific endonuclease and the volume of non-specific endonuclease containing buffer can be adjusted. For example, to minimize the time needed to cleave DNA contaminates the concentration of non-specific endonuclease may be increased; alternatively to minimize the amount of non-specific endonuclease utilized the time of exposure may be increased. In a specific embodiment, the non-specific endonuclease is Benzonase®. Following treatment with a non-specific endonuclease the treated filtered viral harvest is filtered again to remove any residue digested DNA contaminates and remaining host cell debris.

In certain embodiments the Benzonase treated clarified viral harvest is stabilized by the addition of a sucrose phosphate (SP), tris sucrose (TS) or sucrose phosphate glutamate (SPG) buffer. These buffers may further contain a salt such as sodium chloride or potassium chloride. In ceratin embodiments, the stabilization buffer is a SP buffer wherein the buffer comprises sucrose, potassium phosphate (a combination of mono- and dibasic) and potassium chloride. In a specific embodiment the SP buffer comprises about 250 mM to about 200 mM sucrose, 100 mM potassium phosphate and about 150 mM potassium chloride, pH 7.2. In a specific embodiment, the SP comprises 214 mM sucrose. In certain embodiments the stabilization buffer is a TS buffer wherein the buffer comprises about 2.5 mM to about 75 mM, pH 7.2 TrisCl and about 250 mM to about 150 mM sucrose. In a specific embodiment, the stabilization buffer contains 50 mM, pH 7.2 TrisCl and 218 mM sucrose. The TS buffers may further contain, alone or in combination, NaCl, KCl, $KH_2PO_4$ or $K_2HPO_4$. In one embodiment the concentration of NaCl or KCl is about 125 mM to about 175 mM. In a specific embodiment the stabilization buffer contains 5 mM, pH 7.2 TrisCl, 175 mM sucrose and 150 mM NaCl or 150 mM KCl. In another specific embodiment, the stabilization buffer contains 36 mM pH 7.2 TrisCl, 214 mM sucrose and 150 mM NaCl or KCl. In one embodiment the $KH_2PO_4$ or $K_2HPO_4$ is present at about 10 mM to about 2.5 mM. In a specific embodiment the stabilization buffer contains 5 mM, pH 7.2 TrisCl, 175 mM sucrose, 150 mM NaCl and 5 mM $KH_2PO_4$. In certain embodiments, the stabilization buffer is SPG, wherein the buffer contains 218 mM sucrose, 3.8 mM $KH_2PO_4$, 7.2 mM $K_2HPO_4$ and 5 mM Sodium Glutamate. One of skill in the art will recognize that the concentrations of the stabilization buffers can be altered depending on the virus, the viral harvest and purification conditions to obtain the highest yield of stabilized viral harvest.

In certain embodiments, the clarified harvest is concentrated and/or the buffer is exchanged. In one embodiment, concentration and/or buffer exchange is performed by UF and DF. In another embodiment, TFF is used for both the UF and DF. In certain embodiments, the TFF is run so as to maintain a constant Filtrate Flux rate. In other embodiments, the TFF is run so as to maintain a constant TMP. In a specific embodiment the UF step is performed using a 500 kDa hollow fiber cartridge (GE Healthcare) wherein the viral harvest is concentrated 5-fold using an operation TMP of 15 psi and a shear rate of 12000 $sec^{-1}$. These parameters can be altered depending on the virus and the purification conditions to maximize the ultimate virus yield for final vaccine formulation.

In certain embodiments, the clarified virus is first concentrated by UF and then the buffer-exchange is performed with one or two DF buffers. By way of example, but not limitation, the clarified harvest is first concentrated by UF and then subjected to two DF steps with exchange buffers that differ in the concentrations of sucrose and salt. Thus, it is contemplated that the exchange buffer may be the same or different from that present in the viral harvest. In addition, the exchange buffer may be the same or different from the final formulation buffer depending on additional buffer exchange steps. In one embodiment, the exchange buffer is an SP, TS or a sucrose citrate buffer at a neutral pH. In a specific embodiment the exchange buffer comprises about 7-25% w/v sucrose, thus providing a low to high range of sucrose of about 100 mM to about 800 mM. In one embodiment, the exchange buffer comprises NaCl or KCl at a concentration of about 1 mM to about 150 mM. In another embodiment the exchange buffer comprises TrisCl at a concentration of about 2.5 mM to about 50 mM. In yet another embodiment, the exchange buffer comprises sodium or potassium citrate at a concentration of about 5.0 mM to about 50 mM. In one embodiment, the exchange buffer comprises potassium phosphate at a concentration of about 20 mM to about 150 mM. In certain embodiments, the concentration of potassium phopshate is a combination of mono- and dibasic in a low or high concentration typically corresponding with the high or low concentration of sucrose. In a specific embodiment, the exchange buffer comprises about 5 mM to about 30 mM potassium phosphate monobasic. In another specific embodiment, the exchange buffer comprises about 10 mM to about 80 mM potassium phosphate dibasic. Examples of specific exchange buffers include, but are not limited to, 5 mM TrisCl; 7-25% w/v sucrose; 1 mM to 150 mM NaCl; 20 mM sodium or potassium citrate, 7-25% w/v sucrose, 150 mM NaCl or KCl; and 100 mM potassium phosphate, 7-25% w/v sucrose, 150 mM KCl. In a specific embodiment, the exchange buffer comprises 25% w/v sucrose, about 100 mM potassium phosphate buffer and about 150 mM KCl, pH 7.2. In further embodiments, the concentration of potassium phosphate in such an exchange buffer is a combination of mono- and dibasic, e.g., 28.5 mM monobasic and 71.2 mM dibasic. In another specific embodiment, the exchange buffer comprises 25% w/v sucrose, about 5 mM TrisCl and about 150 mM NaCl, pH 7.2. In yet another specific embodiment, the exchange buffer comprises 10% w/v sucrose, about 20 mM potassium phosphate buffer and about 100 mM KCl, pH 7.0. In a further embodiment, the concentration of potassium phosphate in such an exchange buffer is a combination of mono- and dibasic, e.g. 7.7 mM monobasic and 12.3 mM dibasic. The exchange buffer components can be modified depending on the virus and the purification conditions to maximize viral yield of the chromatography step and the final filtration step as well as place the purified virus in a buffer compatible for final formulation.

In certain embodiments, the stabilized viral harvest is further purified by chromatography as described supra. In some embodiments, ion exchange chromatography is used (e.g., anion or cation). In a specific embodiment, following volume reduction by UF and buffer exchange by diafiltration of the treated clarified viral harvest the virus is further purified by ion-exchange chromatography. This chromatography step, or polishing step, is performed in one embodiment using negative chromatography. In this embodiment a surface (e.g., polymeric beads) is derivatized to bind HCD or HCP while excluding the binding of the virus particles thus allowing the virus to pass by the surface. This concept could also be applied to other surfaces such that the buffer comprising the virus particles can pass over or by the derivatized surface. The complete chromatography process is free of additives and easily scalable for use in large scale production of virus for vaccine formulation. It is contemplated that the chromatography can be performed in a batch process or alternatively utilizing a column process. In certain embodiments, the conditioned viral load is purified by column chromatography.

Following either the chromatography step, if performed, or the buffer exchange, the concentrated viral harvest is subjected to a sterilization step. In one embodiment, the sterilization step is a terminal filtration step. In one embodiment the termination filtration is DFF through at least one membrane having a pore size 3 micrometers or less. In a specific embodiment the filter is a dual 3/0.8 micrometer membrane. In another specific embodiment the filter is about 1 mM or less. In one aspect the filter is 0.8, 0.65 or 0.45 micrometers.

In a specific embodiment, the method of purifying respiratory syncitial virus from virus-infected cells comprises the following steps:
a. clarifying a viral harvest comprising;
   i. filtering the viral harvest by direct flow filtration (DFF) through at least one clarification filter having a pore size of between about 10 micrometers to about 3 micrometers;
   ii. treating the viral harvest with a non-specific endonuclease;
   iii. filtering the viral harvest by DFF through at least one clarification filter having a pore size of between about 3 micrometers to about 0.45 micrometers;
b. stabilizing the clarified viral harvest with sucrose, phosphate or Tris buffer with salt (NaCl or KCl);
c. concentrating the stabilized viral harvest by tangential flow filtration (TFF) and performing buffer exchange by diafiltration (DF) using a hollow fiber cartridge with the molecular weight cut off (MWCO) between 500 kDa-0.1 µm;
d. filtering the concentrated viral harvest by DFF through at least one clarification filter having a pore size of between about 0.8 micrometers to about 0.45 micrometers;
whereby the respiratory syncitial virus is purified from the virus-infected cells and has a final viral infectivity titer of at least 5.7 $\log_{10}$ FFU/mL In another specific embodiment the purification method comprises a step of purification by cation-exchange chromatography following concentrating of the viral harvest and buffer exchange.

In yet another specific embodiment, the method of purifying respiratory syncitial virus from virus-infected cells comprises the following steps:
a. clarifying a viral harvest comprising;
   i. filtering the viral harvest by direct flow filtration (DFF) through at least one clarification filter having a pore size of between about 3 to 8 micrometers;
   ii. treating the viral harvest with a non-specific endonuclease;
   iii. filtering the viral harvest by DFF through at least one clarification filter having a pore size of about 0.65 micrometers;
b. stabilizing the clarified viral harvest with sucrose, phosphate or Tris buffer with salt (NaCl or KCl);
c. concentrating the stabilized viral harvest by tangential flow filtration (TFF) and performing two buffer exchanges by diafiltration (DF) using a hollow fiber cartridge with the molecular weight cut off (MWCO) between 500 kDa-0.1 µm;
d. filtering the concentrated viral harvest by DFF through at least one dual clarification filter having a pore size of about 3/0.8 micrometers;
whereby the respiratory syncitial virus is purified from the virus-infected cells and has a final viral infectivity titer of at least 5.7 $\log_{10}$ FFU/mL In a further embodiment, the two buffer exchanges in step c. are performed with the same exchange buffer. Alternatively, the two buffer exchanges are performed with different exchange buffers. In a specific embodiment the DF is performed with a first exchange buffer comprising about 25% w/v sucrose, about 100 mM potassium phosphate buffer and about 150 mM KCl, pH 7.2. In a further specific embodiment, the DF is performed with a second exchange buffer comprising about 10% w/v sucrose, about 20 mM potassium phosphate buffer and about 100 mM KCl, pH 7.0.

6.6 Vaccine Compositions and Methods of Use

The invention further relates to viruses (e.g., influenza or RSV) which are obtainable by a method of the invention. These viruses can be formulated by known methods to provide a vaccine for administration to humans or animals. The viruses can be present as intact virus particles (e.g., live attenuated viruses) or as inactive/disintegrated virus (e.g., treated with detergents of formaldehyde). Optionally, a defined viral component (e.g., protein) may be isolated from the viruses by methods know to the person skilled in the art, and used in the preparation of a vaccine. Methods for the generation and formulation of inactive/disintegrated virus particles for vaccine compositions are well known in the art and have been utilized for over 40 years.

6.6.1 Influenza Virus Vaccine

The formulation of intact virus particles (e.g., live attenuated viruses) may include buffers, amino acid excipients (e.g., glutamate, arginine), protein hydrolysate (e.g., collagen, gelatin), chelating agents (e.g., EDTA) and preservatives. Buffers useful for such a formulation may contain 200 mM sucrose and a phosphate or histidine buffer of pH 7.0-7.4. In certain embodiments, the formulation of intact virus particles comprises amino acid excipients such as glutamate and arginine. In certain other embodiments, the formulation of intact virus particles comprises stabilization protein hydrolysates such as collagen or gelatin (e.g., porcine, piscine, avian gelatin). In some embodiments, the formulation of intact virus particles can comprise live viruses that are stable in liquid form for a period of time sufficient to allow storage "in the field" (e.g., on sale and commercialization when refrigerated at 2-8° C., 4° C., 5° C., etc.) throughout an influenza vaccination season (e.g., typically from about September through March in the northern hemisphere). Thus, the virus/vaccine compositions are desired to retain their potency or to lose their potency at an acceptable rate over the storage period. In other embodiments, such solutions/vaccines are stable in liquid form at from about 2° C. to about 8° C., e.g., refrigerator temperature. For example, methods and compositions for formulating a refrigerator stable attenuated influenza vaccine are described in PCT Patent Publication No. WO/2006/041819; also see PCT Publication WO/2005/014862.

Thus, in certain embodiments, the invention provides a refrigerator stable vaccine formulation comprising one or more of the following (within 10% variation of one or more component) in the final formulations: 1-5% arginine; 1-4% gelatin; 5-10% sucrose (optionally in a phosphate buffer); 0.01-0.1% glutamic acid (monosodium, monohydrate); 10-150 mM potassium phosphate and 80-150 mM histidine.

In one specific embodiment, the vaccine formulation comprises one or more of the following (within 10% variation of one or more component); 1-2% arginine; 2% gelatin; 7-10% sucrose (optionally in a phosphate buffer); and 100 mM histidine. In another specific embodiment, the vaccine formulation comprises one or more of the following (within 10% variation of one or more component): 0.01-0.1% glutamic acid (monosodium, monohydrate); 1-2% arginine; 1% gelatin; and 7-10% sucrose in a phosphate buffer.

In certain other embodiments, the invention provides a refrigerator stable vaccine formulation comprising one or more of the following in the final formulations: sucrose: 6-8% weight/volume (w/v); arginine monohydrochloride 1-2% w/v; glutamic acid, monosodium monohydrate 0.05-0.1% w/v; gelatin hydrolysate, porcine Type A (or other sources such as piscine or avian) 0.5-2% w/v; potassium phosphate dibasic 1-2%; and potassium phosphate monobasic 0.25-1% w/v.

In one specific embodiment, the vaccine formulation comprises one or more of the following: sucrose: 6.84% weight/volume (w/v); arginine monohydrochloride 1.21% w/v; glutamic acid, monosodium monohydrate 0.094 w/v; gelatin hydrolysate, porcine Type A (or other sources) 1% w/v; potassium phosphate dibasic 1.13%; and potassium phosphate monobasic 0.48% w/v. In another specific embodiment, the vaccine formulation comprises all of the following: sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In another specific embodiment, the vaccine formulation comprises all of the following (within 10% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v. In another specific embodiment, the vaccine formulation comprises all of the following (within 10% variation of one or more component): sucrose: 6.84% weight/volume (w/v); arginine monohydrochloride 1.21% w/v; gelatin hydrolysate, porcine Type A (or other sources) 1% w/v. In such embodiments, formulations are in buffer {e.g., a potassium phosphate buffer (pH 7.0-7.2)). In another specific embodiment, vaccine formulations comprise all of the following (within 20% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In yet another specific embodiment, the vaccine formulation comprises all of the following (within 30% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v. In still another specific embodiment, the vaccine formulation comprises all of the following (within 40% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In another specific embodiment, the vaccine formulation comprises all of the following (within 1% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v. In another specific embodiment, the vaccine formulation comprises all of the following (within 3% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v. In a specific embodiment, the vaccine formulation may contain, e.g., potassium phosphate (e.g., at least 50 mM, or at least 100 mM, or at least 200 mM, or at least 250 mM) as a buffer or alternatively, histidine (e.g., at least 50 mM, or at least 100 mM, or at least 200 mM, or at least 250 mM).

Optionally, spray drying, a rapid drying process whereby the formulation liquid feed is spray atomized into fine droplets under a stream of dry heated gas, may be utilized to extend storage time of a vaccine formulation. The evaporation of the fine droplets results in dry powders composed of the dissolved solutes (see, e.g., US Patent Publication No. 2004/0042972).

Generally, virus or viral components can be administered prophylactically in an appropriate carrier or excipient to stimulate an immune response specific for one or more strains of virus. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

Optionally, the formulation for prophylactic administration of the viruses, or components thereof, also contains one or more adjuvants for enhancing the immune response to the influenza antigens. Suitable adjuvants include: saponin, mineral gels such as aluminum hydroxide, surface active substances such as lysolecithin, pluronic polyols, polyanions, peptides, oil or hydrocarbon emulsions, Bacille Calmette-Guerin (BCG), *Corynebacterium parvum*, and the synthetic adjuvants QS-21 and MF59.

Generally, vaccine formulations are administered in a quantity sufficient to stimulate an immune response specific for one or more strains of influenza virus. Preferably, administration of the viruses elicits a protective immune response. Dosages and methods for eliciting a protective immune response against one or more viral strain are known to those of skill in the art. For example, inactivated influenza viruses are provided in the range of about 1-1000 $HID_{50}$ (human infectious dose), i.e., about $10^5$-$10^8$ pfu (plaque forming units) per dose administered. Alternatively, about 10-50 µg, e.g., about 15 µg HA is administered without an adjuvant, with smaller doses being administered with an adjuvant. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needleless injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. While stimulation of a protective immune response with a single dose is preferred, additional dosages can be administered, by the same or different route, to achieve the desired prophylactic effect. These methods can be adapted for any virus including but not limited to, orthomyxoviruses (including influenza A and B strains), paramyxoviruses (including RSV, human metapneumovirus and parainfluenza), rhabdoviruses and flaviviruses.

6.6.2 RSV Vaccines

In one embodiment, presented herein, are methods of eliciting an immune response in a subject, comprising administering to a subject in need thereof an effective amount of an immunogenic composition described herein that comprises a live attenuated purified virus (e.g., RSV). In some embodiments, the attenuated virus is a chimeric virus.

In a specific embodiment, presented herein are methods of eliciting an immune response in a mammal (e.g., a human), comprising administering to a mammal in need thereof an effective amount of an immunogenic composition described herein that comprises an attenuated RSV. In a particular embodiment, the attenuated RSV is rA2cp248/404/1030ΔSH.

The immunogenic compositions described herein that comprise a live attenuated purified virus may be in the active immunization of a subject. In one embodiment, presented herein are methods of preventing a viral infection, comprising administering to a subject an effective amount of an immunogenic composition described herein that comprises a live attenuated purified virus, i.e., a vaccine. In some embodiments, a live attenuated virus is a chimeric virus.

In a specific embodiment, presented herein are methods for preventing a RSV infection, comprising administering to a mammal (e.g., a human) an effective amount of an immunogenic composition described herein that comprises a live attenuated purified RSV, i.e., a vaccine. In a particular embodiment, a live attenuated RSV is rA2cp248/404/1030ΔSH.

The immunogenic compositions described herein that comprise a live attenuated purified virus may be used in the inhibition of viral infections. In one embodiment, presented herein are methods of inhibiting a viral infection, comprising administering to a subject in need thereof an effective amount of an immunogenic composition described herein that comprises a live attenuated purified virus. In some embodiments, the attenuated virus is a chimeric virus. In a specific embodiment, presented herein are methods for inhibiting a RSV infection, comprising administering to a mammal (e.g., a human) an effective amount of an immunogenic composition described herein that comprises a live attenuated purified RSV. In a particular embodiment, the attenuated RSV is rA2cp248/404/1030ΔSH.

The immunogenic compositions described herein that comprise a live attenuated purified virus may be used to induce an immune response that results in a reduction in virus titer in a subject. In one embodiment, presented herein are methods of reducing the titer of a virus in a subject, comprising administering an immunogenic composition described herein that comprises a live attenuated cell-associated virus. In some embodiment, the attenuated virus is chimeric. In a specific embodiment, presented herein are methods for reducing RSV titer, comprising administering to a mammal (e.g., a human) an effective amount of an immunogenic composition described herein that comprises a live attenuated RSV. In a particular embodiment, the attenuated RSV is rA2cp248/404/1030ΔSH.

In some embodiments, an effective amount of an immunogenic composition described herein reduces viral titer by approximately 2 fold, preferably approximately 5 fold or more, approximately 10 fold or more, or approximately 20 fold or more in a subject challenged by the virus relative to an untreated subject. In certain embodiments, an effective amount of an immunogenic compositions described herein reduces the duration and/or severity of one or more symptoms associated with a cell-associated virus infection in subjects subsequently infected with the cell-associated virus relative to untreated subjects. In some embodiments, an effective amount of an immunogenic composition described herein increases survival of subjects subsequently infected with the purified virus relative to untreated subjects.

The immunogenic compositions described herein that comprise a live attenuated purified virus may be administered to a naïve subject, i.e., a subject that has not been and is not currently infected with the virus of interest. In one embodiment, an immunogenic composition described herein that comprises a live attenuated cell-associated virus may be administered to a naïve subject that is at risk of developing a viral infection. In a specific embodiment, an immunogenic composition described herein that comprises a live attenuated RSV may be administered to a naïve subject that is at risk of developing a RSV infection. In a particular embodiment, the attenuated RSV is rA2cp248/404/1030ΔSH.

The immunogenic compositions described herein that comprise a live attenuated purified virus may be administered to a subject that has previously been infected with a different group, subgroup or strain of the virus of interest. In one embodiment, an immunogenic composition is administered to a subject that has previously been infected with a virus of a different group, subgroup or strain than the virus of interest and is at risk of developing an infection with the virus of interest.

In one embodiment, an immunogenic composition described herein that comprises a live attenuated RSV (e.g., rA2cp248/404/1030ΔSH) is administered a human infant or human infant born prematurely. In another embodiment, an immunogenic composition described herein that comprises a live attenuated RSV (e.g., rA2cp248/404/1030ΔSH) is administered to a human with cystic fibrosis, bronchopulmonary dysplasia, congenital heard disease, congenital immunodeficiency or acquired immunodeficiency. In another embodiment, an immunogenic composition described herein that comprises a live attenuated RSV (e.g., rA2cp248/404/1030ΔSH) is administered to a human toddler. In another embodiment, an immunogenic composition described herein that comprises a live attenuated RSV (e.g., rA2cp248/404/1030ΔSH) is administered to a human child. In another embodiment, an immunogenic composition described herein that comprises a live attenuated RSV (e.g., rA2cp248/404/1030ΔSH) is administered to a human child in school.

In a specific embodiment, an immunogenic composition described herein that comprises a live attenuated RSV (e.g., rA2cp248/404/1030ΔSH) is administered to a human 1 to 24 months of age. In another embodiment, an immunogenic composition described herein that comprises a live attenuated RSV (e.g., rA2cp248/404/1030ΔSH) is administered to a human 1 to 3 months of age. In another embodiment, an immunogenic composition described herein that comprises a live attenuated RSV (e.g., rA2cp248/404/1030ΔSH) is administered to a human 6 to 24 months of age.

In another embodiment, an immunogenic composition described herein that comprises a live attenuated RSV (e.g., rA2cp248/404/1030ΔSH) is administered a human who has had a bone marrow transplant. In another embodiment, an immunogenic composition described herein that comprises a live attenuated RSV (e.g., rA2cp248/404/1030ΔSH) is administered to an elderly human. In another embodiment, an immunogenic composition described herein that comprises a live attenuated RSV (e.g., rA2cp248/404/1030ΔSH) is administered to a human in a nursing home. In another embodiment, an immunogenic composition described herein that comprises a live attenuated RSV (e.g., rA2cp248/404/1030ΔSH) is administered to a human that lives in a group home (i.e., a home in which 15 or more human subjects live).

In a specific embodiment, an immunogenic composition comprising a live attenuated RSV (e.g., rA2cp248/404/1030ΔSH) is administered to a human subject (in a specific embodiment, the human subject is a human infant, a human infant born prematurely or a human toddler) before the RSV season, typically November through April in the northern hemisphere. In another embodiment, an immunogenic composition comprising a live attenuated RSV (e.g., rA2cp248/404/1030ΔSH) is administered to a human subject (in a specific embodiment, the human subject is a human infant, a human infant born prematurely or a human toddler) during the RSV season, typically November through April in the northern hemisphere. In another embodiment, an immunogenic composition comprising a live attenuated RSV (e.g., rA2cp248/404/1030ΔSH) is administered to a human subject (in a specific embodiment, the human subject is a human infant, a human infant born prematurely or a human toddler) before and during the RSV season, typically November through April in the northern hemisphere.

In certain embodiments, an immunogenic composition described herein that comprises a live attenuated purified virus does not result in complete protection from a viral infection, but results in a lower viral titer compared to an untreated subject when challenged with the virus. In certain embodiments, administration of an immunogenic composition described herein that comprises a live attenuated purified virus results in a 0.5 fold, 1 fold, 2 fold, 4 fold, 6 fold, 8 fold, 15 fold, 25 fold, 50 fold or greater reduction in the titer of the virus relative to an untreated subject when challenged with the virus. In some embodiments, administration of an immunogenic composition described herein that comprises a live attenuated virus results in a 10%, preferably a 25%, 50%, 75% or greater reduction in the titer of the virus relative to an untreated subject when challenged with the virus. Benefits of a reduction in the viral titer include, but are not limited to, less severe symptoms of a viral infection, fewer symptoms of a viral infection, and a reduction in the length of a viral infection.

The immunogenic compositions described herein comprising a live attenuated chimeric cell-associated virus may be used to induce an immune response to a non-viral antigen. The immunogenic composition described herein comprising a live attenuated chimeric cell-associated virus may be used to deliver a protein, polypeptide or peptide of interest to a subject to prevent and/or treat a disease.

Many methods may be used to introduce the immunogenic compositions, e.g., vaccine formulations, described herein, these include, but are not limited to, intranasal, intratracheal, oral, pulmonary, intradermal, intraperitoneal, and parenteral (e.g., intramuscular, intravenous, and subcutaneous) routes. In some embodiments, an immunogenic composition described herein that comprises a live attenuated cell-associated virus is administered via the natural route of infection of the virus. In a specific embodiment, an immunogenic composition comprising a live attenuated RSV (e.g., rA2cp248/404/1030ΔSH) is administered intranasally.

In immunization procedures, the amount of an immunogenic composition to be used and the immunization schedule will be determined by a physician skilled in the art and will be administered by reference to the immune response and antibody titers of the subject. In a specific embodiment, a human infant, human infant born prematurely or a human toddler is administered a dose of an immunogenic composition comprising a live attenuated RSV (e.g., rA2cp248/404/1030ΔSH), wherein the dose of the immunogenic composition comprises approximately 125 to 200 FFU of the attenuated RSV. In another embodiment, a human infant, human infant born prematurely or a human toddler is administered a dose of an immunogenic composition comprising a live attenuated RSV (e.g., rA2cp248/404/1030ΔSH), wherein the dose of the immunogenic composition comprises approximately 125 FFU, approximately 150 FFU, approximately 175 FFU or approximately 200 FFU of the attenuated RSV.

In some embodiments, 2-6 doses of an immunogenic composition comprising approximately 125 to 200 FFU of a live attenuated RSV (e.g., rA2cp248/404/1030ΔSH) is administered to a human infant, a human infant born prematurely or a human toddler. In some embodiments, the doses of the immunogenic composition are administered 1 to 6 months apart or 2 to 12 months apart. In a specific embodiment, 3 doses of an immunogenic composition comprising approximately 125 to 200 FFU of a live attenuated RSV (e.g., rA2cp248/404/1030ΔSH) are administered to a human infant, a human infant born prematurely or a human toddler 2 months apart. For example, a first dose of an immunogenic composition comprising 150 FFU of a live attenuated RSV (e.g., rA2cp248/404/1030ΔSH) is administered to an infant less than 1 month old, a second dose of the immunogenic composition comprising 150 FFU of the live attenuated RSV (e.g., rA2cp248/404/1030ΔSH) is administered to the human infant at approximately 2 months old, and a third dose of the immunogenic composition comprising 150 FFU of the live attenuated RSV (e.g., rA2cp248/404/1030ΔSH) is administered to the human infant at approximately 4 months old.

7.7 Viruses

A cell-associated virus may be a naturally occurring virus, a mutagenized virus (e.g., a virus mutated by exposure to UV irradiation, mutagens, and/or passaging), a reassortant (for cell-associated viruses with segmented genomes), and/or a genetically engineered virus. Non-limiting examples of cell-associated RNA viruses include respiratory syncytial virus (RSV), measles virus, influenza virus, human foamy virus, retroviruses such as HTLV, lentiviruses such as HIV and SIV, and reoviruses. Alternatively, a cell-associated virus is a DNA virus, such as a herpes virus. Non-limiting examples of cell-associated DNA viruses include herpes virus, EBV, CMV and Marek's disease virus. In certain embodiments, the cell-associated virus purified by a process described herein and/or contained in an immunogenic composition described herein is replication-defective. In a specific embodiment, one or more functions essential for viral genome replication and/or synthesis are defective in the replication-defective cell-associated virus. In another embodiment, one or more functions essential for assembly of viral particles are defective in the replication-defective cell-associated virus. In another embodiment, one or more functions essential for viral genome replication or synthesis and viral particle assembly are defective in the replication-defective cell-associated virus.

In a specific embodiment, the cell-associated virus purified by a process described herein and/or contained in an immunogenic composition described herein is an attenuated virus.

In a particular embodiment, the cell-associated virus is a live attenuated virus. An attenuated cell-associated virus may have, e.g., a reduced ability to replicate its viral genome, a reduced ability to replicate in an intended host, a reduced ability to assemble infectious viral particles, and/or a reduced ability to infect a host cell relative to a wild-type cell-associated virus. The attenuation of the cell-associated viruses can be tested by any method known to one of skill in the art. See, e.g., U.S. application Ser. No. 10/831,780, Apr. 23, 2004 (published on Jan. 27, 2005 as U.S. Application Publication No. 2005/0019891) and in particular Section 5.7 entitled "Attenuation of Recombinant Viruses,". In some embodiments, the attenuated virus is produced using well-known mutagenesis techniques, such as cold passaging the virus or exposure to UV irradiation and/or mutagens. In other embodiments, the attenuated virus is genetically engineered.

A cell-associated virus may be a chimeric virus. In a specific embodiment, the chimeric virus is a replication-defective virus. In a particular embodiment, the chimeric virus is an attenuated virus.

6.7.1 Influenza Virus

The culture medium, methods, processes and compositions herein are particularly useful for the production and purification of influenza viruses for vaccines. Influenza viruses are made up of an internal ribonucleoprotein core containing a segmented single-stranded RNA genome and an outer lipoprotein envelope lined by a matrix protein. Influenza A and influenza B viruses each contain eight segments of single stranded negative sense RNA. The influenza A genome encodes eleven polypeptides. Segments 1-3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants.

The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a biscistronic mRNA. Segment 7 of influenza B also encodes two proteins: M1 and M2. The smallest segment encodes two products, NS1 which is translated from the full length RNA, and NS2 which is translated from a spliced mRNA variant.

Reassortant viruses are produced to incorporate selected hemagglutinin and/or neuraminidase antigens from clinical isolates in the context of an approved master strain also called a master donor virus (MDV). FluMist®, for example, makes use of approved cold adapted, attenuated, temperature sensitive MDV strains (e.g., A/AnnArbor/6/60 and B/Ann Arbor/1/66). Other strains that may be used as a master donor virus include, but are not limited to, ca A/AnnArbor/6/60, ca B/Ann Arbor/1/66, ca A/Leningrad/134/17/57, A/PuertoRico/8/34

(PR8), ca B/Ann Arbor/1/94, B/Leningrad/14/17/55, B/USSR/60/69, and B/Leningrad/179/86.

A number of methods are useful for the generation of reassortant viruses including egg-based methods and more recently cell culture methods See, e.g., PCT Publications WO 03/091401; WO 05/062820 and U.S. Pat. Nos. 6,544,785; 6,649,372; 6,951,75, and U.S. patent application Ser. Nos. 11/455,818, 11/455,734, and 11/501,067. It is contemplated that the media and methods of the invention are useful for the production of influenza viruses including, but not limited to, the influenza strains disclosed herein and reassortant viruses comprising genes of a master donor virus (e.g., ca A/AnnArbor/6/60, ca B/AnnArbor/1/66, PR8, etc.). It is further contemplated that that the media and methods of the invention are useful for the production of influenza viruses, including reassortant viruses, having one or more of the following phenotypes, temperature sensitive, cold adapted, attenuated. Reassortants may be generated by classical reassortant techniques, for example by co-infection methods or optionally by plasmid rescue techniques (see, e.g., PCT Publications WO 03/091401 and WO 05/062820; U.S. Pat. Nos. 6,544,785, 6,649,372, 6,951,754, 6,887,699, 6,001,634, 5,854,037, 5,824,536, 5,840,520, 5,820,871, 5,786,199, and 5,166,057; U.S. Patent Application Publication Nos. 20060019350, 20050158342, 20050037487, 20050266026, 20050186563, 20050221489, 20050032043, 20040142003, 20030035814, and 20020164770; and Neumann et al. (1999) *Generation of influenza A virus entirely from cloned cDNAs. Proc Natl Acad Sci USA* 96:9345-9350; Fodor et al. (1999) *Rescue of influenza A virus from recombinant DNA. J. Virol* 73:9679-9682; Hoffmann et al. (2000) *A DNA transfection system for generation of influenza A virus from eight plasmids Proc Natl Acad Sci USA* 97:6108-6113; WO 01/83794; Hoffmann and Webster (2000), *Unidirectional RNA polymerase 1-polymerase II transcription system for the generation of influenza A virus from eight plasmids,* 81:2843-2847; and Hoffmann et al. (2002), *Rescue of influenza B viruses from 8 plasmids,* 99(17): 11411-11416. Recently, reassortants have been generated by plasmid rescue in MDCK cells (see, e.g., PCT publication WO 2007/124327; Wang and Duke; 2007 Oct. 23, J. Virol., 4:102).

6.7.2 Respiratory Syncitial Virus

The methods, processes and compositions herein are particularly useful for the production and purification of RSV for vaccines. Any group, subgroup or strain of RSV (e.g., group A or group B) may be purified by a process described herein and/or contained in an immunogenic composition described herein. See, e.g., Sato et al., 2005, Journal of Clinical Microbiology 43: 36-40 for a discussion of the groups and subgroups of RSV. In one embodiment, the RSV belongs to group A. In another embodiment, the RSV belongs to group B.

The RSV purified by a process described herein and/or contained in an immunogenic composition described herein may be a naturally occurring RSV strain, a mutagenized RSV (e.g., a virus mutated by exposure to UV irradiation, mutagens, and/or passaging), and/or a genetically engineered RSV. In one embodiment, the RSV genome comprises one or more mutations in one or more viral genes, such as the F, G, NS1, NS2, M1 (open reading frame ("ORF")1), M2(ORF2), SH2, N, P, or L genes. In some embodiments, a combination of substitutions, deletions and/or insertions are introduced into the RSV genome. In some embodiments, the RSV genome comprises one or more missense mutations in one or more viral genes, such as the F, G, NS1, NS2, M1(ORF1), M2(ORF2), SH2, N, P, or L genes. In some embodiments, the RSV genome comprises a deletion of one or more all or a portion of one or more viral genes, such as the NS1, NS2, M1(ORF1), M2(ORF2), SH2, N, P, or L genes.

In one embodiment, the RSV that may be purified by a process described herein and/or contained in an immunogenic composition described herein is replication-defective. In a specific embodiment, the RSV that may be purified by a process described herein and/or contained in an immunogenic composition described herein is attenuated. For non-limiting examples of mutations that may be introduced into the RSV genome to attenuate the virus see, e.g., U.S. application Ser. No. 10/831,780, Apr. 23, 2004 (published on Jan. 27, 2005 as U.S. Application Publication No. 2005/0019891) and U.S. application Ser. No. 11/389,618, filed Mar. 24, 2006 (published on Jul. 20, 2006 as U.S. Application Publication No. 2006/0160130). Attenuated RSVs include, but are not limited to, cold-passaged (cp) mutants (e.g., cpRSV described in, e.g., Kim et al., 1971, Pediatrics 48: 745-755, which is incorporated herein by reference in its entirety), temperature-sensitive (ts) mutants (e.g., RSV ts-1, RSV ts-2, ts1A, ts19A, and ts1C described in, e.g., Crowe et al., 1993, Vaccine 11:1395-1404; Crowe et al., 1995, Vaccine 13:847-855; Mills et al., 1971, J. Immunol. 107:123-130; and Pringle et al., Vaccine 1993 11:473-478), cold-passaged temperature sensitive (cpts) mutants (e.g., cpts248/404, cpts248/255, cpts 248/955 and cpts 530/1009; see, e.g., Karron et al., 1997, J Infect Dis. 176:1428-1436), and genetically engineered mutants (e.g., rA2cp248/404ΔSH, rA2cp248/404/1030ΔSH, rΔNS1, rΔM2-2, and r248ΔNS2 described in, e.g., Karron et al., J. of Infect. Diseases 191: 1093-1140; Whitehead et al., 1999, J. Virol. 73: 3438-3442; and Collins et al., 2005, Proc. Am. Thorac. Soc. 2: 166-173,).

In a specific embodiment, the RSV that may be purified by a process described herein and/or contained in an immunogenic composition described herein is rA2cp248/404/1030ΔSH. This attenuated RSV contains multiple attenuating genetic elements that are responsible for its temperature sensitivity and attenuation properties including: (i) a set of 5 missense mutations in the N, F and L proteins that attenuate cold-passaged RSV; (ii) the 248 and 1030 modifications that are separate missense mutations in the L protein that lower the restrictive temperature and confer a temperature sensitive phenotype and attenuate the virus; (iii) the 404 modifications that are a combination of a nucleotide substitution in the gene-start transcription signal of the M2 gene and a missense mutation in the L protein that together confer additional temperature sensitivity; and (iv) ΔSH which is a deletion of the entire SH gene that confers an attenuated phenotype. See Table 1 below for the locations of the amino acid substitutions introduced into the RSV genome.

TABLE 1

| Nucleotide Substitutions | Amino Acid Substitutions* | Gene | Phenotype |
|---|---|---|---|
| G1939A | V to I | N | Att |
| A5895C | E to A | F | Att |
| C6810T | T to I | F | Att |
| T7187C | T to C | M2 gene-start | Ts |
| G9035A, T9036C | C to Y | L | Att |
| C10570T, A10571T | Q to L | L | ts |
| T11628G | D to E | L | Ts |
| T12040A | Y to N | L | Ts |
| C13147T, T13149C | H to Y | L | Att |

*Amino acid substitutions relative to wild-type RSV A2

In some embodiments, the RSV that may be purified by a process described herein and/or contained in an immunogenic composition described herein is engineered to express one or more heterologous sequences (i.e., the RSV is a chimeric virus). The heterologous sequences may be introduced, e.g., into the F, G, NS1, NS1, M1 (ORF1), M2(ORF2), N, P, SH2 and/or L coding sequences. Non-limiting examples of heterologous sequences that a RSV may be engineered to express include antigens (e.g., viral antigens, bacterial antigens, tumor antigens (such as those described by Robbins and Kawakawi, 1996, Curr. Opin. Immunol. 8: 628-636), fungal antigens, and parasitic antigens), a marker or tag (e.g., a flag tag and a His tag), chimeric proteins (e.g., a hybrid of RSV G proteins from two different strains of RSV), and proteins, polypeptides or peptides possessing a desired biological property or activity (e.g., cytokines such as interferon (IFN)-α IFN-β, IFN-γ, IL-2, IL-7, IL-9, IL-15, and IL-22). In a specific embodiment, the chimeric RSV is attenuated. For non-limiting examples of chimeric RSVs see, e.g., U.S. application Ser. No. 10/831,780, Apr. 23, 2004 (published on Jan. 27, 2005 as U.S. Application Publication No. 2005/0019891) and U.S. application Ser. No. 11/389,618, filed Mar. 24, 2006 (published on Jul. 20, 2006 as U.S. Application Publication No. 2006/0160130).

In one embodiment, RSV is engineered to express one or more viral antigens from a virus belonging to a different group, subgroup, or strain of RSV than the RSV vector. For example and not by limitation, the RSV vector may be derived from a group B RSV and the heterologous sequence may be derived from a group A RSV.

In another embodiment, RSV is engineered to express one or more viral antigens obtained or derived from a virus other than RSV. Non-limiting examples of viral antigens include antigens from adenoviridae (e.g., mastadenovirus and aviadenovirus), herpesviridae (e.g., herpes simplex virus 1, herpes simplex virus 2, herpes simplex virus 5, herpes simplex virus 6, Epstein-Barr virus, HHV6-HHV8 and cytomegalovirus), leviviridae (e.g., levivirus, enterobacteria phase MS2, allolevirus), poxyiridae (e.g., chordopoxyirinae, parapoxvirus, avipoxvirus, capripoxvirus, leporiipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory synctial virus), human respiratory syncytial virus and metapneumovirus (e.g., avian pneumovirus and human metapneumovirus)), picornaviridae (e.g., enterovirus, rhinovirus, hepatovirus (e.g., human hepatits A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus 1 and human immunodeficiency virus 2 (e.g., HIV gp160), spumavirus), flaviviridae (e.g., hepatitis C virus, dengue virus, West Nile virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus). In a specific embodiment, the viral antigen is derived from a virus that results in respiratory disease, such as influenza antigens (e.g., hemagglutinin H5 and H7), metapneumovirus antigens, parainfluenza virus antigens, Newcastle disease virus antigens, Sendai virus antigens, and infectious Laryngotracheits virus antigens (ILV). In certain embodiments, the viral antigen is derived from human parainfluenza virus type 1, human parainfluenza virus type 2, human parainfluenza virus types 3, or from Sendai virus. In another embodiment, the viral antigen, is HIV gp120, HIV nef, influenza virus neuraminidase, influenza virus hemagglutinin, HTLV tax, herpes simplex virus glycoprotein (e.g., gB, gC, gD, and gE) or hepatitis B surface antigen, hepatitis C virus E protein or coronavirus spike protein.

In another embodiment, RSV is engineered to express one or more bacterial antigens (e.g., a bacterial coat protein or protective antigen associated with a bacteria). Non-limiting examples of bacterial antigens include antigens derived from bacteria of the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), Enterobacteriaceae family (e.g., *Citrobacter* species, Edwardsiella, *Enterobacter aerogenes, Erwinia* species, *Escherichia coli, Hafnia* species, *Klebsiella* species, *Morganella* species, *Proteus vulgaris*, Providencia, *Salmonella* species, *Serratia marcescens*, and *Shigella flexneri*), Gardinella family, *Haemophilus influenzae*, Halobacteriaceae family, Helicobacter family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcus* (e.g., methicillin resistant *Staphylococcus aureus* and *Staphylococcus pyrogenes*), *Streptococcus* (e.g., *Streptococcus enteritidis, Streptococcus fasciae*, and *Streptococcus pneumoniae*), Vampirovibr Helicobacter family, Yersinia family, *Bacillus antracis* and Vampirovibrio family. In a specific embodiment, the bacterial antigen is derived from a bacteria that cause or are associated with a respiratory disease, such as *Pneumococcus* species, *Haemophilus influenzae, Streptococcus*, and *Chlamydia pneumoniae*.

In another embodiment, RSV is engineered to express one or more fungal antigens obtained or derived from a pathogenic fungus. Non-limiting examples of fungal antigens include antigens derived from *Cryptococcus neoformans; Blastomyces dermatitidis; Aiellomyces dermatitidis; Histoplasma capsulatum; Coccidioides immitis; Candida* species, including *C. albicans, C. tropicalis, C. parapsilosis, C. guilliermondii* and *C. krusei, Aspergillus* species, including *A. fumigatus, A. flavus* and *A. niger, Rhizopus* species; *Rhizomucor* species; *Cunninghammella* species; *Apophysomyces* species, including *A. saksenaea, A. mucor* and *A. absidia; Sporothrix schenckii, Paracoccidioides brasiliensis; Pseudallescheria boydii, Torulopsis glabrata; Trichophyton* species, *Microsporum* species and *Dermatophyres* species. In a specific embodiment, the fungal antigen is derived from a pathogenic fungus that cause or are associated with a respiratory disease.

In another embodiment, RSV is engineered to express one or more parasitic antigens. Non-limiting examples of parasitic antigens include antigens derived from members of the Apicomplexa phylum such as, for example, *Babesia, Toxoplasma, Plasmodium, Eimeria, Isospora, Atoxoplasma, Cystoisospora, Hammondia, Besniotia, Sarcocystis, Frenkelia, Haemoproteus, Leucocytozoon, Theileria, Perkinsus* and *Gregarina* spp.; *Pneumocystis carinii*; members of the *Microspora phylum* such as, for example, *Nosema, Enterocytozoon, Encephalitozoon, Septata, Mrazekia, Amblyospora, Ameson, Glugea, Pleistophora* and *Microsporidium* spp.; and members of the *Ascetospora phylum* such as, for example, *Haplosporidium* spp., as well as species including *Plasmo-*

*dium falciparum, P. vivax, P. ovale, P. malaria; Toxoplasma gondii; Leishmania mexicana, L. tropica, L. major, L. aethiopica, L. donovani, Trypanosoma cruzi, T brucei, Schistosoma mansoni, S. haematobium, S. japonium; Trichinella spiralis; Wuchereria bancrofti; Brugia malayli; Entamoeba histolytica; Enterobius vermiculoarus; Taenia solium, T. saginata, Trichomonas vaginatis, T hominis, T. tenax; Giardia lamblia; Cryptosporidium parvum; Pneumocytis carinii, Babesia bovis, B. divergens, B. microti, Isospora belli, L. hominis; Dientamoeba fragilis; Onchocerca volvulus; Ascaris lumbricoides; Necator americanis; Ancylostoma duodenale; Strongyloides stercoralis; Capillaria philippinensis; Angiostrongylus cantonensis; Hymenolepis nana; Diphyllobothrium Tatum; Echinococcus granulosus, E. multilocularis; Paragonimus westermani, P. caliensis; Chlonorchis sinensis; Opisthorchis felineas, G. Viverini, Fasciola hepatica, Sarcoptes scabiei, Pediculus humanus; Phthirlus pubis;* and *Dermatobia hominis.*

8. EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein. Of course, it will be appreciated that specific listing or description of particular equipment and reagents used, sizes, manufacturer, etc., is not to be considered limiting on the current invention unless specifically stated to be so. It with be further appreciated that other equipment and reagents which perform similarly may be readily substituted.

8.1 Example 1

Medium and Cell Culture Processes

Serum-free medium formulations (e.g., MediV SFM 107, MediV SFM 105) useful for the proliferation of MDCK cells, in particular non-tumorigenic MDCK cells, to high density have been described (see, e.g., FL410US and G-FL414US). However, work using these serum-free medium formulations with non-tumorigenic MDCK cells adapted to serum-free medium (e.g., ATCC Accession No. PTA-7909 or PTA-7910) revealed that, while reasonable peak viral titers (generally measured as $\log_{10}$ FFU/mL) of reassortant influenza virus could be obtained without medium exchange, the peak titers were still lower that those obtained with medium exchange, in which a portion (e.g., ~67%) of the growth medium is removed and replaced with an infection medium after proliferation the cells and prior to (or at the same time as) infection. Furthermore additional protease (TrypLE) was required to obtain these peak titers. To overcome the need for medium exchange and/or the requirement for addition protease a fortified medium, MediV SFM 110, was developed. MediV SFM 110 comprises 5× the concentration of the vitamins, linoleic acid, lipoic acid, nucleosides, putrescine and nearly all the amino acids present in the previously described mediums (see Table 2). Use of MediV SFM 110 did not improve cell densities over those obtained with MediV SFM 105+TE (data not shown). However, using MediV SFM 110, 0% and 67% medium exchange showed similar viral titers.

The performance of twelve runs using a no medium exchange (MX) process and cells prepared by bead to bead transfer (see the Example provided in Section 8.2 below) from four seed reactors and grown in MediV SFM 110 media are described below. Three cold adapted (ca), temperature sensitive (ts), attenuated (att) reassortant influenza virus strains comprising the HA and NA from the wild type strains A/Uruguay/716/2007, A/South Dakota/6/2007, and B/Florida/4/2006 (referred to by the wild type strain designation preceded by the identifier "ca") were produced at 2 L scale and all the three strains produced viruses at a titer of at least 8.4 $\log_{10}$ FFU/mL. Proper detachment of cells in the seed reactors and attachment of cells in the final production reactors (FPRs) were observed after bead to bead transfer using 1×DPBS wash and trypsinization using TrypLE select and EDTA at pH8.0. Upon infection these cells were sampled periodically to determine the optimum harvest time. It was found that the peak virus titers were observed at 3 days post infection (dpi) for all virus types. Four runs for each of these strains were performed to verify reproducibility of results and the data were in-line to each other. ca A/Uruguay/716/2007 produced the highest titer at 8.7±0.05 $\log_{10}$ FFU/mL at 3 days post infection (dpi), while the peak titers for ca A/South Dakota/6/2007 and ca B/Florida/4/2006 were 8.8±0.0 $\log_{10}$ FFU/mL and 8.45±0.25 $\log_{10}$ FFU/mL respectively at 3 dpi.

The reproducibility of data from these runs indicates the no medium exchange process is a robust process. Thus, the fortified media maintained productivity without either exchanging or adding medium or components. Accordingly, development and use of the fortified medium has overcome one of the most challenging operational problems in cell culture-based influenza vaccine production, the requirement for medium exchange/supplementation.

8.1.1 Materials and Methods

Materials, Reagent and Equipments:
Other materials, equipment and reagents which perform similarly may be readily substituted.
1. Dulbecco's Modified Eagle's Medium (DMEM)/Ham F12 (Gibco, Grand Island, N.Y., Cat No. ME080012)
2. MilliQ or WFI Water
3. MediV SFM 110 base powder (Gibco, Grand Island, N.Y., Cat No. ME080045)
4. Glucose (Invitrogen, Carlsbad, Calif., Cat No. 15023-021)
5. Sodium Selenite (Sigma, St. Louis, Mo., Cat No. 6607-31) ?
6. L-Glutamine (Gibco, Grand Island, N.Y., Cat No. 25030-081)
7. CD Lipids (100×) (Gibco, Grand Island, N.Y., Cat No. 11905-031)
8. Wheat Peptone (Organotechnie, SAS, La Courneuve, France, Cat No. 19559)
9. Insulin (Serological, Norcross, Ga., Cat No. 4506)
10. T3 (Sigma, St. Louis, Mo., Cat No. T5516)
11. Hydrocortisone (Mallinckrodt, Phillipsburg, N.Y., Cat No. 8830(–05))
12. Prostaglandin E1 (Sigma, St. Louis, Mo., Cat No. P7527)
13. EGF (Sigma, St. Louis, Mo., Cat No. E9644)
14. Ferric Ammonium Citrate (J T Baker, Phillipsburg, N.J., Cat No. 1980-01)
15. Tropolone (Sigma, St. Louis, Mo., Cat No. T89702-5G)
16. Trace Element A (Cellgro/Mediatech, Manassas, Va., Cat No. 99-182-cl)
17. Trace Element B (Cellgro/Mediatech, Manassas, Va., Cat No. 99-175-cl)
18. Trace Element C (Cellgro/Mediatech, Manassas, Va., Cat No. 99-176-cl)

19. Sodium Biocarbonate (Invitrogen, Carlsbad, Calif., Cat. No. 91425/87-5067)
20. Dulbecco's phosphate buffered saline (DPBS) pH-7.4 (Invitrogen, Carlsbad, Calif., Cat No. 14190-367)
21. EDTA-DPBS solution Bag (Gibco Cat No. 14190-367)
22. 0.5M EDTA pH8 (Gibco, Grand Island, N.Y., Cat No. 15575-038)
23. 0.2 μm steri cup filter (Millipore, Bedford, Mass., Cat No. SCGPUO5RE)
24. TrypLE Select (Gibco, Grand Island, N.Y., Cat No. 12563)
25. Lima Bean Inhibitor (Worthington, Lakewood, N.J., Cat No. LS002829)
26. Cytodex 3 (Amersham Biosciences, Piscataway, N.J., Cat No. 17-0485-03)
27. Sucrose Phosphate (Hyclone, Logan, Utah, Cat No. SH3A1578-01)
28. 10-20 L sterile bag (SAFC Biosciences JRH, Lenexa, Kans., 1329B)
29. Roller Bottles (Corning, Corning, N.Y., Cat No. 3907)
30. NaOH 1M solution (EMD, Darmstadt, Germany, Cat No. 1071)
31. 0.2 μm sterile filter (Corning, Corning, N.Y., Cat No. 430320, 430767)
32. 1 mL, 5 mL, 10 mL, 25 mL, 50 mL Pipettes (VWR, Brisbane, Calif., Cat. Nos. 53284-700, 53283-704, 708, 710, respectively)
33. 5 mL aspirating pipettes (VWR, Brisbane, Calif., Cat No. 53392-044)
34. 1.8 mL Eppendorf tubes (USA Scientific, Ocala Fla., Cat No. 1415-5510)
35. Micropipette tips (Art Molecular Bioproducts, San Diego Calif., Cat No. 20E, 200E and 1000E)
36. Sucrose Phosphate, 10× (Hyclone, Logan, Utah, Cat# SH3A1578-01)
37. Applikon Controller Units (Applikon Biotechnology, Foster City, Calif. Models: ADI 1010, ADI 1025)
38. 3 L glass vessel and headplate (Biotechnology, Foster City, Calif.)
39. 2.5" A310 impellers (Lightnin, Rochester, N.Y.)
40. 60 mm marine impeller (Applikon Biotechnology, Foster City, Calif.).
41. 45 mm marine impellers (Applikon Biotechnology, Foster City, Calif.).
42. Peristaltic pump (Watson Marlow Bredel Pump, Wilmington, Mass., Model 5205/R)
43. Biosafety cabinet (The Baker Company, Sanford, Me., SG-600)
44. Roller bottle incubator (Bellco Biotechnology, Vineland, N.J., Model 7630-80589)
45. Water bath (Boekel Grant, West Chester, Pa., PB-1400)
46. Nucleocounter (New Brunswick Scientific, Edison, N.J., M1293-0000)
47. Bioprofile 400 (Nova Biomedical, Waltham, Mass., Bioprofile 400)
48. Microscope (Zeiss, Thornwood, N.Y., Axiovert 25)
49. Digital Camera (Nikon, Melville, N.Y., Model E5400)
50. Micropipette (Labsystem, Boston, Mass., Model No. P2-20, P100, P200, P1000)
51. Pipette aid (Drummond, Broomall, Pa., Cat. No. 4-000-100)
52. $CO_2$ Shake flask incubator (ATR Biotech, Laurel, Md., Model AJ118)

Cell Source:

Serum-free MDCK clone ID 9B9-1E4 cells derived from the Process Development Bank (PDB) were cultivated in roller bottles, using MediV SFM105 with trace elements A, B and C or MediV SFM109[4]. The composition of MediV SFM 105 with trace elements A, B and C is similar to MediV SFM 109 media, with the exception that MediV SFM 105 is made out of liquid and MediV SFM109 is made out of powder. Cells were routinely passaged every 3 to 4 days post-seeding as per SOP D0200[5], with the exception that the 2×DPBS wash was not performed.

Virus Seed:

This process was developed with the 2008/2009 FluMist® seasonal strains: A/Uruguay/716/2007 (Lot # nb3903 pg94, 141900675A), A/South Dakota/6/2007 (Lot #141900666), and B/Florida/4/2006 (141900641A). All these seeds were produced in eggs. Similar results have been obtained for seed viruses produced in cell culture using plasmid rescue methods (see, for example, Wang and Duke; 2007 Oct. 23, J. Virol., 4:102; Hoffmann, et al., 2000, PNAS, 97(11):6108-13; and Hoffmann, et al., 2002, PNAS, 99(17):11411-6)

Culture Medium:

For these runs MediV SFM 105 with 1× Trace Elements A, B and C and a total 4.5 g/L of D-glucose or MediV SFM 109 with a total 4.5 or 9.0 g/L of D-glucose were used in all routine cell passaging for roller bottles and seed reactors (SRs) runs, respectively. MediV SFM 110 medium with a total of 9.0 g/L of D-glucose was used for final production reactors (FPRs) runs. Depending on the seeding conditions and the anticipated he concentration of D-glucose may be adjusted between about 4.5 to about 9.0 g/L. The composition of each culture medium is detailed in Table 2.

TABLE 2

MediV SFM Medium Formulations

| Component[a] | MediV SFM 105 + TE[d] mg/L | MediV SFM 109 mg/L | MediV SFM 110 mg/L |
| --- | --- | --- | --- |
| Salts | | | |
| Calcium Chloride, Anhydrous | 116.6 | 116.6 | 116.6 |
| Magnesium Chloride | 28.64 | 28.64 | 28.64 |
| Magnesium Sulfate, Anhydrous | 48.84 | 48.84 | 48.84 |
| Potassium Chloride | 311.8 | 311.8 | 311.8 |
| Sodium Chloride[c] | 6999.5 | 6999.5 | 3500 |
| Sodium Phosphate, Monobasic, Monohydrate | 62.5 | 62.5 | 62.5 |
| Sodium Phosphate, Dibasic, Anhydrous | 71.02 | 71.02 | 71.02 |

TABLE 2-continued

MediV SFM Medium Formulations

| Component[a] | MediV SFM 105 + TE[d] mg/L | MediV SFM 109 mg/L | MediV SFM 110 mg/L |
|---|---|---|---|
| Trace Metals | | | |
| $NH_4VO_3$ | 0.00065 | 0.00065 | 0.00065 |
| $AgNO_3$ | 0.00017 | 0.00017 | 0.00017 |
| Aluminum Chloride $6H_2O$ | 0.0012 | 0.0012 | 0.0012 |
| $Ba(C_2H_3O_2)$ | 0.00255 | 0.00255 | 0.00255 |
| Cadmium Chloride ($CdCl_2$) | 0.00228 | 0.00228 | 0.00228 |
| Chromium Chloride ($CrCl_3$, anhydrous) | 0.00032 | 0.00032 | 0.00032 |
| Cobalt Chloride $6H_2O$ | 0.00238 | 0.00238 | 0.00238 |
| Cupric Sulfate, Pentahydrate | 0.0029 | 0.0029 | 0.0029 |
| Ferric Citrate | 1.1551 | 1.1551 | 1.1551 |
| Ferric Nitrate, Nonahydrate | 0.05 | 0.05 | 0.05 |
| Ferric Ammonium Citrate (FAC) | 0.2 | 0.2 | 0.2 |
| Ferrous Sulfate, Heptahydrate | 0.417 | 0.417 | 0.417 |
| $GeO_2$ | 0.00053 | 0.00053 | 0.00053 |
| $MnSO_4 H_2O$ | 0.00017 | 0.00017 | 0.00017 |
| Molybdic Acid ammonium Salt | 0.00124 | 0.00124 | 0.00124 |
| Nikelous Sulfate ($NiSO_4 6H_2O$) | 0.00013 | 0.00013 | 0.00013 |
| Potassium Bromide | 0.00012 | 0.00012 | 0.00012 |
| Potassium Iodide | 0.00017 | 0.00017 | 0.00017 |
| Rubidium Chloride | 0.00121 | 0.00121 | 0.00121 |
| Sodium Selenite | 0.0173 | 0.0173 | 0.0173 |
| Sodium Selenite, Pentahydrate | 0.00263 | | |
| Sodium Floride | 0.0042 | 0.0042 | 0.0042 |
| Sodium Meta-Silicate•$9H_2O$ | 0.14 | 0.14 | 0.14 |
| Stannous Chloride(Tin Chloride-$SnCl2$) | 0.00012 | 0.00012 | 0.00012 |
| Zinc Sulfate, Heptahydrate | 1.295 | 1.295 | 1.295 |
| $ZrOCl_2 8H_2O$ | 0.00322 | 0.00322 | 0.00322 |
| Nucleosides[b] | | | |
| Hypoxanthine, Na salt | 2.39 | 2.39 | 11.95 |
| Thymidine | 0.365 | 0.365 | 1.825 |
| Amino Acids[b] | | | |
| L-Alanine | 4.45 | 4.45 | 22.25 |
| L-Arginine HCl | 147.5 | 147.5 | 737.5 |
| L-Asparagine $H_2O$ | 7.5 | 7.5 | 37.5 |
| L-Aspartic Acid | 6.65 | 6.65 | 33.25 |
| L-Cysteine HCl $H_2O$ | 17.56 | 17.56 | 87.8 |
| L-Cystine 2HCl | 31.29 | 31.29 | 156.45 |
| L-Glutamic Acid | 7.35 | 7.35 | 36.75 |
| L-Glutamine | 584 | 584 | 584 |
| Glycine | 18.75 | 18.75 | 93.75 |
| L-Histidine HCl $H_2O$ | 31.48 | 31.48 | 157.4 |
| L-Isoleucine | 54.47 | 54.47 | 272.35 |
| L-Leucine | 59.05 | 59.05 | 295.25 |
| L-Lysine HCl | 91.25 | 91.25 | 456.25 |
| L-Methionine | 17.24 | 17.24 | 86.2 |
| L-Phenylalanine | 35.48 | 35.48 | 177.4 |
| L-Proline | 17.25 | 17.25 | 86.25 |
| L-Serine | 26.25 | 26.25 | 131.25 |
| L-Threonine | 53.45 | 53.45 | 267.25 |
| L-Tryptophan | 9.02 | 9.02 | 45.1 |
| L-Tyrosine 2Na | 55.79 | 55.79 | 278.95 |
| L-Valine | 52.85 | 52.85 | 264.25 |
| Vitamins[b] | | | |
| d-Biotin (vit B7 and vit H) | 0.0035 | 0.0035 | 0.0175 |
| D-Calcium Pantothenate | 2.24 | 2.24 | 11.2 |
| Choline Chloride | 8.98 | 8.98 | 44.9 |
| Cyanocobalamin (vit B12) | 0.68 | 0.68 | 3.4 |
| Folic Acid | 2.65 | 2.65 | 13.25 |
| myo-Inositol | 12.6 | 12.6 | 63 |
| Niacinamide | 2.02 | 2.02 | 10.1 |
| Pyridoxine HCl (vit B6) | 2.031 | 2.031 | 10.155 |
| Riboflavin(vit B2) | 0.219 | 0.219 | 1.095 |
| Thiamine HCl (vit B1) | 2.17 | 2.17 | 10.85 |
| Fatty Acids[b] | | | |
| α Linoleic Acid | 0.042 | 0.042 | 0.21 |
| α DL--Lipoic Acid | 0.105 | 0.105 | 0.525 |

TABLE 2-continued

MediV SFM Medium Formulations

| Component[a] | MediV SFM 105 + TE[d] mg/L | MediV SFM 109 mg/L | MediV SFM 110 mg/L |
|---|---|---|---|
| Other | | | |
| Putrescine[b], 2HCl | 0.081 | 0.081 | 0.405 |
| Sodium Bicarbonate | 2200 | 2200 | 4400 |
| Sodium Pyruvate | 55 | 55 | 55 |
| *Tropolone* | *0.25* | *0.25* | *0.25* |
| *Glucose*[e] | *≥4500* | *≥4500* | *≥4500* |
| Insulin | 5 | 5 | 5 |
| T3 | 0.000003367 | 0.000003367 | 3.367E−06 |
| PGE1 | 0.025 | 0.025 | 0.025 |
| *Hydrocotisone* | *0.01812* | *0.01812* | *0.01812* |
| EGF | 0.005 | 0.005 | 0.005 |
| *Wheat peptone* | *2500* | *2500* | *2500* |
| *CDLC stock solution (components below)* | *1X* | *1X* | *1X* |
| *Arachidonic Acid* | *0.02* | *0.02* | *0.02* |
| *Cholesterol* | *2.2* | *2.2* | *2.2* |
| *DL-α-Tocopherol-Acetate* | *0.7* | *0.7* | *0.7* |
| *Linoleic Acid* | *0.1* | *0.1* | *0.1* |
| *Linolenic Acid* | *0.1* | *0.1* | *0.1* |
| *Myristic Acid* | *0.1* | *0.1* | *0.1* |
| *Oleic Acid* | *0.1* | *0.1* | *0.1* |
| *Palmitic Acid* | *0.1* | *0.1* | *0.1* |
| *Palmitoleic Acid* | *0.1* | *0.1* | *0.1* |
| *Pluronic F68* | *1000* | *1000* | *1000* |
| *Stearic Acid* | *0.1* | *0.1* | *0.1* |
| *Tween 80* | *22* | *22* | *22* |
| Final pH | | | 7.3 |

[a]Components not found in DMEM/F12 are shown in italics.
[b]Components found in DMEM/F12 and fortified in MediV SFM 110
[c]Reduced concentration in MediV SFM 110 to maintain osmolality
[d]Trace Elements A, B, and C
[e]Glucose is present at a final concentration of at least 4.5 g/L and may be supplemented up to a final concentration of about 9.0 g/L.

TABLE 3

1000X Trace Element Solutions A, B and C

| Components | mg/L |
|---|---|
| Trace Elements Soln. A | |
| $CuSO_4 \cdot 5H_2O$ | 1.60 |
| $ZnSO_4 \cdot 7H_2O$ | 863.00 |
| Selenite•2Na | 17.30 |
| Ferric citrate | 1155.10 |
| Trace Elements Soln. B | |
| $MnSO_4 \cdot H_2O$ | 0.17 |
| $Na_2SiO_3 \cdot 9H_2O$ | 140.00 |
| $NH_4VO_3$ | 0.65 |
| $NiSO_4 \cdot 6H_2O$ | 0.13 |
| $SnCl_2$ (anhydrous) | 0.12 |
| Molybdic acid, Ammonium salt | 1.24 |
| Trace Elements Soln. C | |
| $AlCl_3 \cdot 6H_2O$ | 1.20 |
| $AgNO_3$ | 0.17 |
| $Ba(C_2H_3O_2)_2$ | 2.55 |
| KBr | 0.12 |
| $CdCl_2$ | 2.28 |
| $CoCl_2 \cdot 6H_2O$ | 2.38 |
| $CrCl_3$ (anhydrous) | 0.32 |
| NaF | 4.20 |
| $GeO_2$ | 0.53 |
| KI | 0.17 |
| RbCl | 1.21 |
| $ZrOCl_2 \cdot 8H_2O$ | 3.22 |

TABLE 4

100X Chemically Defined Lipid (CDCL) Solution

| Component | FW | mg/L |
|---|---|---|
| Arachidonic Acid | 304.5 | 2 |
| Cholesterol | 387 | 220 |
| DL-α-Tocopherol-Acetate | 473 | 70 |
| Linoleic Acid | 280 | 10 |
| Linolenic Acid | 278.43 | 10 |
| Myristic Acid | 228.37 | 10 |
| Oleic Acid | 282.46 | 10 |
| Palmitic Acid | 256.42 | 10 |
| Palmitoleic Acid | 254.41 | 10 |
| Pluronic F68 | | 100000 |
| Stearic Acid | 284.48 | 10 |
| Tween 80 | | 2200 |

Bioreactor Conditions and Methods:

For all the Experiments, the FPRs were inoculated using 1:8 split contents from seed reactor (SR) and infected with reassortants of the 2008/2009 seasonal viruses, ca A/Uruguay, ca A/South Dakota and ca B/Florida. Several FPRs were run at identical conditions to ensure robustness of process and capture variability. First 3 experiments were performed to compare the medium exchange (MX) and no medium exchange (No-MX) processes side-by-side using one of 2008/2009 virus for each experiment. For each of the first 3 experiments, 2×2 L FPRs were run in replicates at identical conditions, where no medium exchange was performed at the time of infection and the reactors were infected with the same virus strains to capture process variability. Thus, a total of 6×2 L bioreactors were inoculated with 1:8 split cell culture contents from SRs and infected with all three 2008/2009 seasonal virus strains with no medium exchange process.

The last 2 experiments were performed to generate more data for the performance of no medium exchange process for the 08/09 strains. For the 4$^{th}$ experiment, 3×2 L FPRs were inoculated from 1×2 L SR and were infected with all three seasonal virus reassortant types. Experiment 5 was a replicate of experiment 4 using identical conditions. The experiment was repeated in order to capture process variability in order to access performance of the no medium exchange process.

The virus strain used for infection and the source of cells used to inoculate FPRs in each experiment are described in Table 5.

TABLE 5

Virus strain and cell source used in Final Production Reactors (FPRs) infection

| Experiment | Cell Source (SRs) | FPRs | Infection virus |
|---|---|---|---|
| Experiment 1 | SR1 | FPR1.1.1 | A/Uruguay |
| | | FPR1.1.2 | A/Uruguay |
| Experiment 2 | SR2 | FPR2.2.1 | A/South Dakota |
| | | FPR2.2.2 | A/South Dakota |
| Experiment 3 | | FPR3.2.1 | B/Florida |
| | | FPR3.2.2 | B/Florida |
| Experiment 4 | SR3 | FPR4.3.1 | A/Uruguay |
| | | FPR4.3.2 | A/South Dakota |
| | | FPR4.3.3 | B/Florida |
| Experiment 5 | SR4 | FPR5.4.1 | A/Uruguay |
| | | FPR5.4.1 | A/South Dakota |
| | | FPR5.4.3 | B/Florida |

Seed Reactors (SRs):

For all the experiments, cells were grown in seed bioreactors at either 2 L or 5 L scale using 2 g/L of Cytodex 3 microcarriers in MediV SFM 105 medium containing Trace Elements A, B and C (MediV SFM 105+TE) or MediV SFM 109 media. The composition of MediV SFM 105 with trace elements A, B and C is nearly identical to MediV SFM 109 media, with the exception that MediV SFM 105 is made out of liquid and MediV SFM 109 is made out of powder and contains less sodium selenite. The glucose and glutamine concentrations were 9.0 g/L and 4 mM respectively. The vessels were inoculated at $1.35 \times 10^5$ cells/mL for experiments 1 to 3 and $1.8 \times 10^5$ cells/mL for experiments 4 and 5. The dissolved oxygen (D.O.) in SRs was maintained at 50% using a combination of pure oxygen and $N_2$ at a constant total flow of 0.02 vvm. The pH control was dual sided utilizing both $CO_2$ and 1N NaOH for all the SRs. Working volume for SRs for experiment 1 and experiment 2 were 2 L and 5 L respectively. Both were equipped with one marine impeller and agitated at 175 RPM. The working volume SRs for experiments 3 and 4 was 2 L. Both were equipped with 2 Lightnin impellers and agitated at 175 RPM. The impact of impeller and working volume on cell growth and metabolism is neglected for the scope of study. For the first 3 experiments, SRs were inoculated with 22.5 cells/MC. In order to achieve better cell growth, the SRs for experiment 4 and 5 were inoculated at 30 cells/MC. The experimental design describing each FPR with its respective SR is presented Table 5 and the process conditions are described in Table 6 for each SRs. After 4 days post seeding, the agitator, gas flow and D.O. and temperature controls of SRs were switch off to allow microcarriers to settle and cells were washed and trypsinized with one half of the working volume of bioreactor with addition of 10× TrypLE and pH8 essentially as detailed below in the Example provided in Section 8.2, below. The contents of SRs were trypsinized using B2B transfer protocol as specified in Table 7.

Final Production Reactors (FPRs):

The seed reactors contents were then pumped into feed bottles and 125 mL of this cell inoculum were used to inoculate the FPRs at the split of 1:8. The cells in the FPRs were grown in MediV SFM 110 medium containing 9.0 g/L glucose concentration. 2 L FPR glass vessels were equipped with 2 lightnin impellers and agitated at 175 RPM. The D.O. was controlled at 50% air saturation controlled with total flow strategy at 0.02 vvm, where constant total flow of 40 mL/min was maintained where supply of $N_2$ gas was calculated from $O_2$ and $CO_2$ gases ($N_2$=40-$O_2$—$CO_2$). The pH control was dual sided utilizing both $CO_2$ and 1N NaOH for all the FPRs. The temperature during the growth and infection phase was controlled at 37° C. and 33° C. respectively. The virus strain for FPRs are listed in Table 5 and process conditions during growth and infection phase for the FPRs are listed in Table 8.

TABLE 6

Seed Reactor (SR) Process Conditions

| Parameter set-points | Controlled Quantity | | | |
|---|---|---|---|---|
| | SR1 | SR2 | SR3 | SR4 |
| Glucose (g/L) | 9.0 | 9.0 | 9.0 | 9.0 |
| Initial cells/micro-carriers (λ) | 22.5 | 22.5 | 30 | 30 |
| Final Working Volume (L) | 2 | 5 | 2 | 2 |
| Micro-carrier (MC) concentration (g/L) | 2 | 2 | 2 | 2 |
| Dissolved Oxygen | 50 | 50 | 50 | 50 |
| pH | 7.4 | 7.4 | 7.4 | 7.4 |
| Growth Temperature (° C.) | 37 | 37 | 37 | 37 |
| Impeller quantity/type | 1/marine | 1/marine | 2/lightnin | 2/lightnin |
| Agitation (RPM) | 175 | 175 | 175 | 175 |
| pH control | With 1N NaOH and $CO_2$ | With 1N NaOH and $CO_2$ | With 1N NaOH and $CO_2$ | With 1N NaOH and $CO_2$ |

TABLE 6-continued

Seed Reactor (SR) Process Conditions

| | Controlled Quantity | | | |
|---|---|---|---|---|
| Parameter set-points | SR1 | SR2 | SR3 | SR4 |
| Total flow (constant throughout the run) (mL/min) | 40 | 40 | 40 | 40 |
| Media used | SFM105 with Trace elements A, B and C | SFM109 | SFM109 | SFM109 |

TABLE 7

Trypsinization conditions using bead to bead protocol

| Steps | Specifications and Set-points | Values | Units |
|---|---|---|---|
| 1. | Remove Media | 80 | % |
| 2. | Add 0.5 mM EDTA/DPBS wash solution to the original working volume | 80 | % |
| 3. | Start the agitation to original setting | 15 ± 5 | min |
| 4. | Stop agitation to allow MCs to settle down | 15 ± 5 | Min |
| 5. | Remove media and DBPS | 80 | % |
| 6. | Add 0.5 mM EDTA/DPBS wash solution to half of original working volume | 50 | % |
| 7. | Set agitator speed | 250 | RPM |
| 8. | Start the DO and temperature controls to original settings | 50, 37 | %, ° C. |
| 9. | Adjust the pH setting on controller | 8.0 | pH |
| 10. | Add 10x TrypLE Select (X of remaining volume) | 0.05 | X |
| 11. | Time for trypsinization | 50 ± 10 | Min |

TABLE 8

Final Production Reactor (FPR) Process Conditions

| Parameter set-points | FPRs |
|---|---|
| Final working volume (L) | 2 |
| Final microcarrier (MC) concentration (g/L) | 2 |
| Cell source | B2B SR |
| Split ratio | 1:8 |
| Volume of SR content post bead to bead transferred (mL)[#] | 125 |
| Dissolved oxygen | 50 |
| pH | 7.4 |
| pH control | With 1N NaOH and $CO_2$ |
| Agitation (RPM) | 175 |
| Final growth media glucose concentration (g/L) | 9.0 |
| Growth temperature (° C.) | 37 |
| Media | SFM110 |
| Infection temperature (° C.) | 33 |
| 10x TrypLE select concentration (X) | 0.03 |

[#]The cell content is concentrated 2X during the bead to bead transfer process. Accordingly, 125 mL post bead to bead is equivalent to 250 mL pre bead to bead.

Analytical Procedures:

Daily sampling of the vessels were performed. Cells were counted using the Nucleocounter, and photographs were taken using microscope at 10x magnification to examine cell morphology. pH, pO2, pCO2 and concentrations of glucose, lactate, glutamine and ammonium were monitored daily using a Nova Bioprofile 400 Analyzer. A pH re-calibration of the bioreactor was carried out when the difference between the online and offline values was higher than 0.03 pH units. Infected samples were stabilized with 10x Sucrose Phosphate (SP) and frozen at −80° C. until analyzed. The progression of the virus replication was analyzed by measuring the viral infectivity by Focal Fluorescent Assay (FFA) essentially as described below.

Focal Fluorescent Assay (FFA):

MDCK cells are grown in 96 well plates in MEM/EBSS+ 1× non-essential amino acids+2 mM glutamine+PEN/Strep (VGM) at 36±1° C. ° C., 5±2% $CO_2$, until confluent (~4 days). The VGM is then removed and the cells are washed with fresh VGM followed by infection with 100 µL of virus inoculum (e.g., ca A/Uruguay, ca A/South Dakota and ca B/Florida)) that is serially diluted (e.g., $10^{-1}, 10^{-2} \ldots 10^{-7}$) in VGM and incubated for approximately 19-20 hrs at 33±1° C., 5±2% $CO_2$. Each virus dilution is inoculated to cells in three replicates. After incubation for approximately 19-20 hours at 33±1° C., 5±2% $CO_2$ the cells are immuno-stained with anti-influenza antibodies to determine the virus titer of the samples according to the following procedure. The cell culture medium containing the viruses is removed from each plate and the plates are washed with 200 µl/well of DPBS followed by fixation in 100 µL of cold 4% paraformadehyde for 15±3 minutes at room temperature. The plates are then washed twice with 250 µl/well of 1× Phosphate Buffered Saline+0.05% Tween 20 (TPBS) followed by incubation of the cells with primary antibody specific for either A strains or B strains. The primary antibodies are diluted to the desired dilution in 0.1% saponin, 1% BSA, and 0.1% sodium azide in 1×PBS (SBSA). After incubation for 60±5 minutes at 37±1° C., the primary antibody is removed, cells are washed thrice with 250 µL TPBS, and secondary antibody conjugated to a fluorescent dye (e.g., rabbit anti sheep labeled with FITC) prepared to the desired dilution in SBSA is added to the wells. After incubation for 60±5 minutes at 37±1° C., the secondary antibody is removed and the plates are washed twice as described above and twice with nano water followed by blot-drying with paper towels. The plates are then air dried with the lids off in the dark at room temperature for at least 10 minutes. The fluorescent signals are visualized using an inverted fluorescence microscope at 100× total magnification. Images may be taken using imaging software such as the SPOT program. Generally the central band of each well is examined and all foci are counted and only those wells which have a count of between 8 and 120 foci are counted. The $\log_{10}$ FFU/mL is calculated for each well counted and the mean and standard deviation of three wells are calculated.

8.1.2 Results and Discussion

Figure 1:
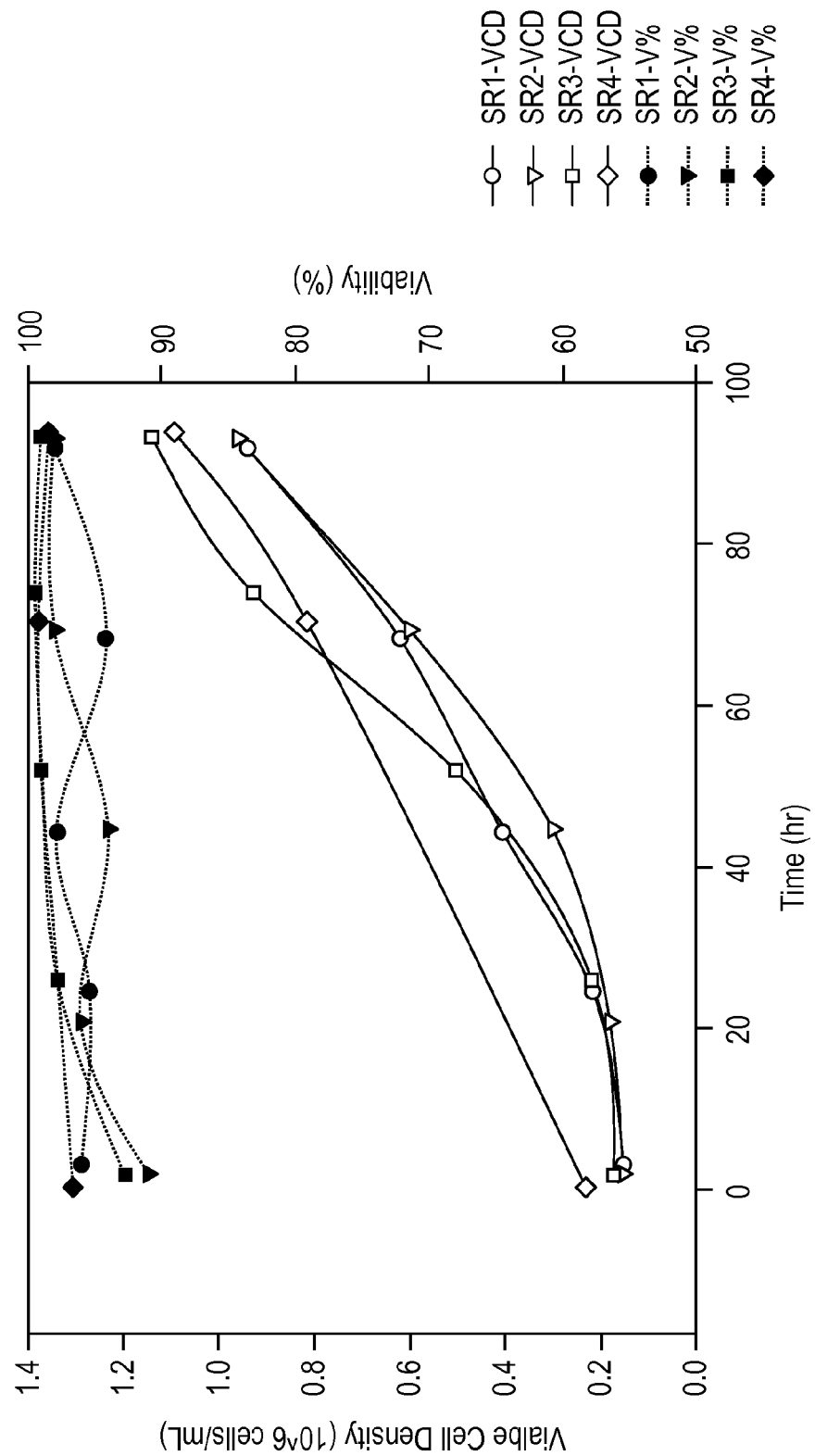
Figure 2:
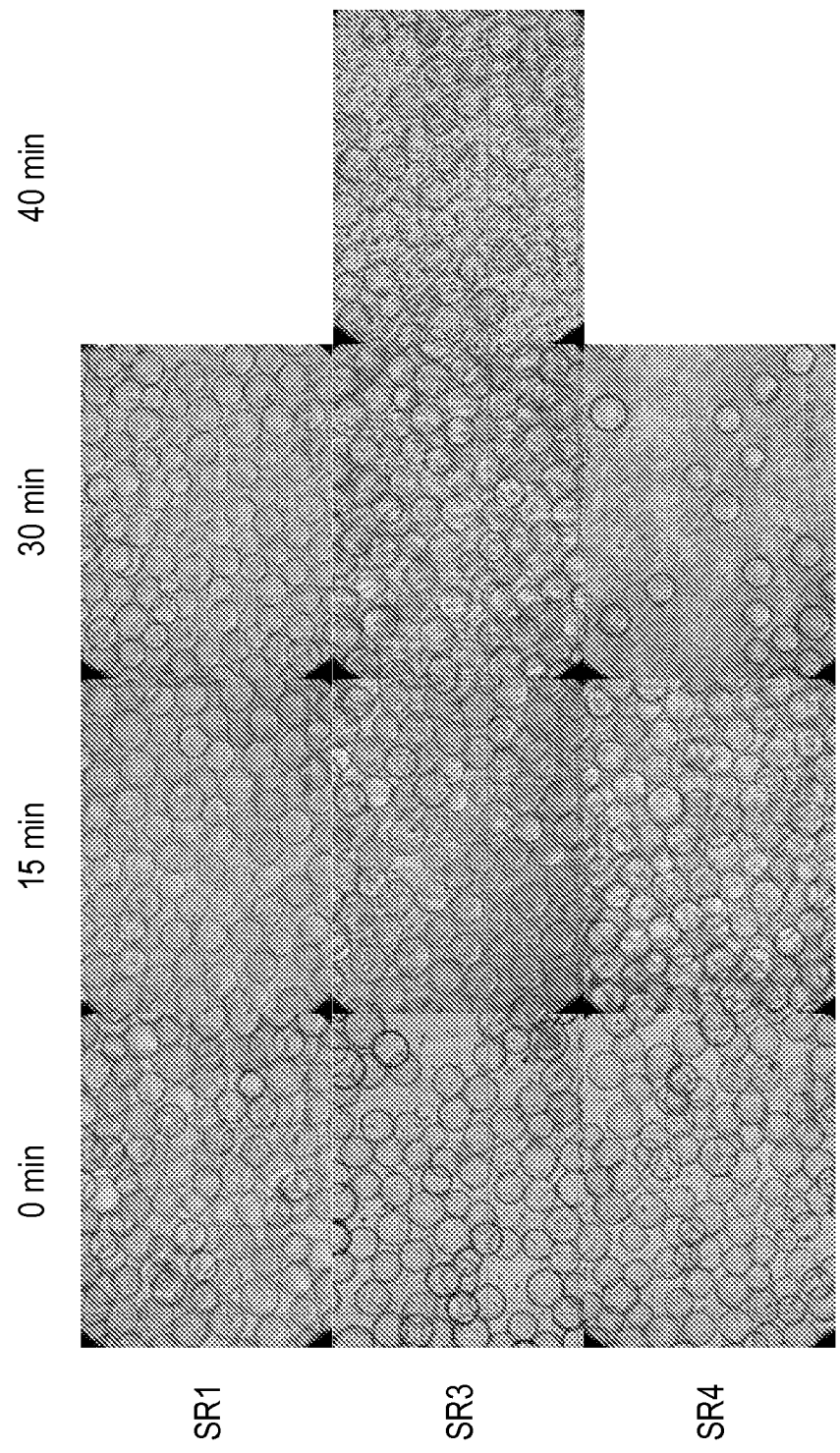
Figure 3:
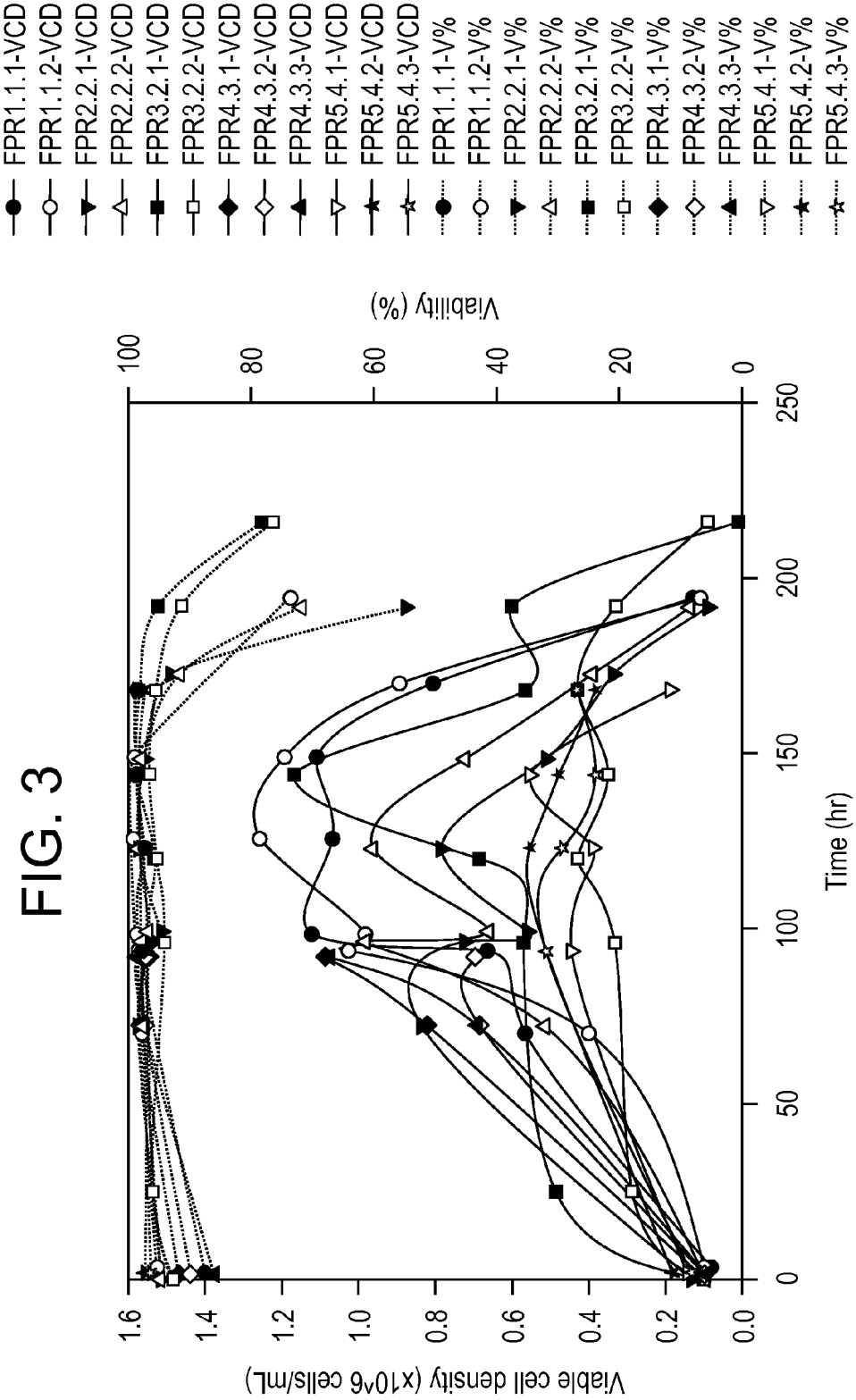

Cells were inoculated with 22.5 and 30 cells/microcarriers (MC) for the seed bioreactors for the first 3 experiments and last 2 experiments respectively. FIG. 1 plots the viable cell density (VCD) and cell viability (V %) for the SRs for all experiments. At 4 dps the cell densities for the seed reactors ranged from 0.94 to 1.14 million cells/mL. The difference in cell density was potentially due to the difference in inoculation cell concentration of 22.5 and 30 cells/MC. The cell density at 4 day post seeding (dps) in SRs inoculated with 22.5 and 30 cells/MC were 0.95±0.01 and 1.12±0.024 million cells/mL respectively. Cell viability for all bioreactors was above 90%. After 4 days of cultivation, bead to bead transfer with 1×0.5 mM EDTA-DPBS wash and 10× TrypLE select was performed in the seed reactors to trypsinize cells. The trypsinization lasted 30+/−10 minutes with intermittent sampling to observe cell detachment under the microscope. After about 30 to 40 minutes trypsinization, approximately 90% of cells were detached from MCs and seen as single cells as shown in FIG. 2. The trypsinized cells were used to inoculate the final bioreactors at a split ratio of 1:8 for all the experiments. The cell growth for all the FPRs was plotted in FIG. 3. Since the VCD for all the FPRs in experiment 2 were less than $0.6 \times 10^6$ cells/mL at 4 dps and the cell culture in these FPRs experienced longer lag phase, these cells were infected on 5 dps instead of 4 dps. In addition, the post infection VCD data were not available for FPRs in experiment 4. Finally, in spite of the low VCD of less than $0.5 \times 10^6$ cells/mL the FPRs were infected on 4 dps in experiment 5. The viability was above 90% for the FPRs during cell growth phase.

The cell density at the time of infection for all the FPRs are recorded in Table 9. Large variation in viable cell density was seen. It ranged from 0.44 to $1.12 \times 10^6$ cells/mL. This difference was related to cell counting error. The average VCD for both SRs and FPRs is recorded in Table 10. On 4 dps average VCD for SRs and FPRs is about $1.12 \times 10^6$ cells/mL and $0.73 \times 10^6$ cells/mL, respectively.

TABLE 9

Viable cell density at infection for all FPRs (unit: $\times 10^6$ cells/mL)

| Runs | VCD at infection | Days post |
|---|---|---|
| FPR1.1.1 | 1.12 | 4 |
| FPR1.1.2 | 0.98 | 4 |
| FPR2.2.1 | 0.56 | 4 |
| FPR2.2.2 | 0.66 | 4 |
| FPR3.2.1 | 0.68 | 5 |
| FPR3.2.2 | 0.44 | 5 |
| FPR4.3.1 | 1.09 | 4 |
| FPR4.3.2 | 0.69 | 4 |
| FPR4.3.3 | 1.07 | 4 |
| FPR5.4.1 | 0.51 | 4 |
| FPR5.4.2 | 0.51 | 4 |
| FPR5.4.3 | 0.44 | 4 |

TABLE 10

Average viable cell density for all SRs and FPRs

| Average 4 dps VCD ($\times 10^6$ cells/mL) | SRs w/λ of 22.5 cells/MC | 0.95 ± 0.01 |
|---|---|---|
| | SRs w/λ of 30 cells/MC | 1.12 ± 0.024 |
| Average VCD at infection ($\times 10^6$ cells/mL) | FPRs with no MX process | 0.73 ± 0.026 |

Figure 4:
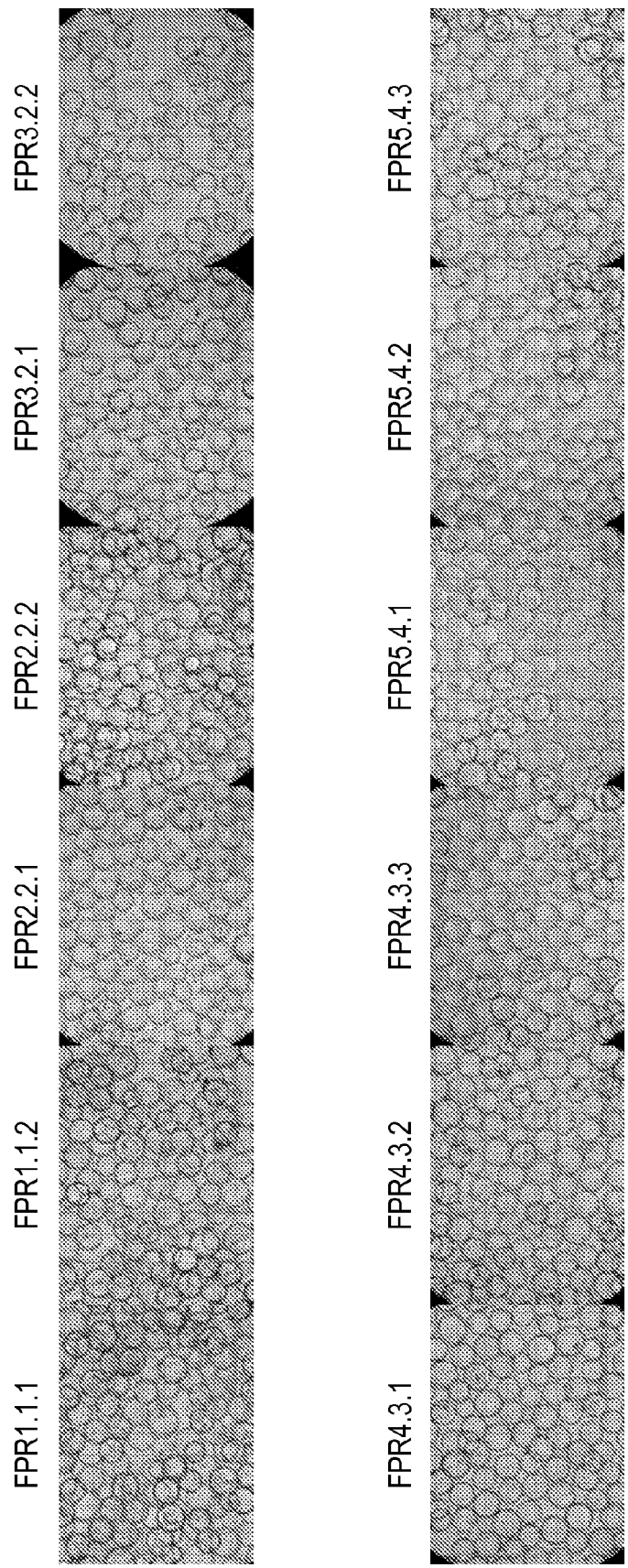
FIG. 4 shows photographs (taken at 100× magnification) taken on 4 dps for 12×2 L final production reactors for all experiments.
Figure 5:
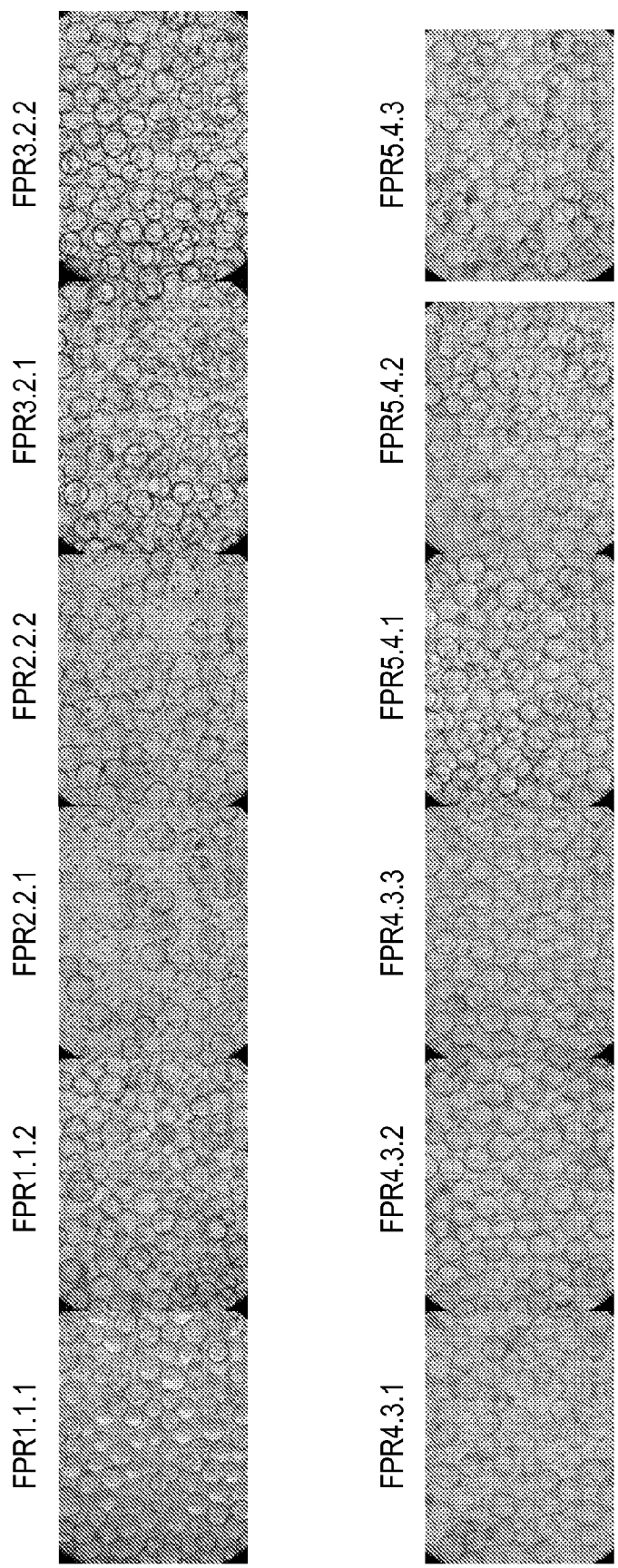
FIG. 5 shows photographs (taken at 100× magnification) taken on 3 dpi for 9×2 L final production reactors (FPR) for all experiments.

After trypsinization, the cells in FPRs attached to the microcarrier beads at 0 dps and then began to proliferate on the surface of the microcarrier beads. Most of the microcarriers were covered with cells and only some beads remained empty (no cells covering the beads) by 4 dps. Cell morphology was similar in all the experiments. Photographs showing typical cell morphology on 3 dps and 4 dpi are presented in FIG. 4 and FIG. 5, respectively.

On 4 or 5 dps, the FPRs in experiment 1, 2 and 3 were infected with ca A/Uruguay, ca A/South Dakota and ca B/Florida respectively. Prior to infection 0.03× of 10× TrypLE select was added to the cell culture medium. In experiment 4 and 5 individual FPR was infected with one of the three seasonal strains ca A/Uruguay, ca A/South Dakota and ca B/Florida at 20 FFU/mL. FIG. 6 shows that peak virus titers were reached between 68 and 74 hours post infection (hpi). Moreover, the virus titer remained high thereafter until 92 hpi.

The average virus titers for each virus strain types is summarized in Table 11 They were 8.7, 8.8 and 8.45 $\log_{10}$ FFU/mL for ca A/Uruguay, ca A/South Dakota and ca B/Florida, respectively. This is in line to or above what was observed for these viruses when 67% medium exchange was made.

Additional experiments were performed to compare viral titers for four strains (ca A/Wisconsin/67/05, A ca A/Uruguay, ca A/South Dakota and ca B/Florida) produced using the 67% medium exchange process (performed essentially as described in International Patent Publication WO 08/105, 931, see Example 12) versus no medium exchange process (performed essentially as described above). At least two runs were performed for each process and strain. It can be seen from FIG. 7 that the peak viral titers for each strain are comparable between the 67% medium exchange and the no medium exchange process.

TABLE 11

Average peak virus tiers for each virus strains for the FPRs.

| Virus strain | Average peak virus titer (log10FFU/mL) | Peak harvest day (dpi) | No. of FPRs |
|---|---|---|---|
| A/Uruguay/716/2007 | 8.7 ± 0.05 | 3 | 4 × 2 L |
| A/South Dakota/6/2007 | 8.8 ± 0.0 | 3 | 4 × 2 L |
| B/Florida/4/2006 | 8.45 ± 0.25 | 3 | 4 × 2 L |

Medium exchange is a major operational step in current cell culture-based influenza vaccine manufacturing process. Many efforts have been made to eliminate medium exchange prior to infection since without medium exchange the probability of microorganism contamination will be reduced and more operational friendly processes can be implemented. Through a series of twelve bioreactor runs without medium exchange the process performance data, more specifically, cell detachment/attachment, cell growth and virus titers were collected to assess the variability of a new vaccine production process and the feasibility of inoculating FPR with cells directly taken out of SR using a new bead to bead transfer procedure. Three virus strains namely, ca A/Uruguay, ca A/South Dakota and ca B/Florida were each produced four times with no medium exchange prior to infection. It was confirmed that VCD could be reached up to $1 \times 10^6$ cells/mL on 4 dps in SRs and B2B transfer with 1×DPBS, TrypLE Select and EDTA could be accomplished successfully with effective (>90%) cell detachment in seed reactors after 30 to 40 minutes of trypsinization. Cells in FPRs proliferated on the surface of microcarrier beads and reached average VCD of about $0.73 \times 10^6$ cells/mL at the time of infection. Peak virus titers for ca A/Uruguay, ca A/South Dakota and ca B/Florida for all the FPR runs with no MX process were 8.7±0.05, 8.8±0.0 and 8.45±0.25 $\log_{10}$ FFU/mL respectively at 3 dpi. This was better than or in-line with what was generally observed for the virus strains with the 67% medium exchange (see FIG. 8). The peak virus titer for all virus types was greater than 8.4 $\log_{10}$ FFU/mL. These results clearly demonstrated that the B2B transfer and no MX process described here is a very robust process. They minimize the use of costly medium reagents and can reduce the likelihood of contamination.

8.2 Rapid Bead to Bead Transfer Process with Low Concentration of Protease

This example describes the processes and parameters for rapid and efficient bead to bead transfer of MDCK cells using DPBS/0.5 mM EDTA pH8 wash solution and a low concentration of protease (e.g., 0.05× TrypLE) in spinner flask, shaker flask or stirred tank bioreactor. An overview of the process flow is provided in FIG. 8. Representative equipment and reagents that can be used in the process are detailed in Table 12, Table 13, and Table 14. Of course, other equipment and reagents which perform similarly may be optionally substituted herein and specific mention of particular brands or types of equipment and reagents should not be construed as limiting unless specifically indicated to be so.

This process was utilized in the twelve runs described above. As noted, a proper cell detachment in the seed reactors and attachment for cells in FPRs was observed using the bead to bead transfer protocol using 1×DPBS wash with EDTA and trypsinization using TrypLE select at pH8. Thus, the bead to bead transfer process is rapid, efficient and robust.

TABLE 12

Equipment List

| Equipment | Manufacturer | Model |
|---|---|---|
| Bio Safety Cabinet (BSC) | Baker | SG-600 |
| Controller/Console | Applikon | ADI1030/ADI1035 |
| Stirred tank bioreactors (5 L, 10 L; 15 L) | Applikon | Z611000010 |
| Microscope | Zeiss or Nikon | Axiovert25 |
| Cedex Cell Counter | Innovatis | G007D00138 |
| Peristaltic Pump | Cole Partner | 7553-70 or equivalent |

TABLE 13

Materials and Reagents

| Component | Suggested Vendor | Catalog Number |
|---|---|---|
| 10X TrypLE Select | Invitrogen | 04-0090DG |
| Ethylenediaminetetraacetic acid (EDTA, disodium salt dihydrate) FW 372.24 | Sigma or equivalent | Cat #E5134-500G |
| 0.5M EDTA pH 8 | Gibco | 15575-038 |
| 0.5M EDTA pH 8 | In-House | NA |
| Dulbecco's Phosphate Buffered Saline (20 L bag); without $Ca^{2+}$ and $Mg^{2+}$ | Gibco or equivalent | 14190-367 |
| Dulbecco's Phosphate Buffered Saline powder 10X; without $Ca^{2+}$ and $Mg^{2+}$ | Gibco or equivalent | 21600-069 |

TABLE 14

DPBS/0.5 mM EDTA - pH 8 Wash Solution Preparation

| Component | Concentration | Volume (mL) |
|---|---|---|
| DPBS | N/A | 1000 |
| 0.5M EDTA pH 8 (Gibco or In-house) | 0.5 mM | 1 |
| pH | 8.0 ± 0.1 | NA |

Preparation of 1× Liquid Medium DPBS from 10×DPBS Powder:

Add powdered medium to room temperature water with gentle stirring. (Do not heat water). Rinse out the inside of the container to remove all traces of powder. Dilute to a desired volume with water. Stir until dissolved. (Do not over-mix). Adjust pH of medium to 7.8±0.1 (final working pH is 8.0). pH units will usually rise 0.1-0.3 upon filtration. After pH has been adjusted keep container closed until medium is filtered. Sterilize immediately using 0.1 micron membrane.

Preparation of 0.5M Stock EDTA:

Add 186.1 g EDTA (disodium, dihydrate) to 800 mL of deionized water. Add about 20 g of NaOH pellets or 10 N NaOH while stirring to bring pH to 8.0. Note: Add the last few grams slowly to avoid overshooting the pH. EDTA won't dissolve until the pH is around 8. Adjust volume to 1 L with deionized water. Filter with 0.1 micron filter. Aliquot into smaller volumes (200 mL each bottle) and store at room temperature.

Preparation of DPBS/0.5 M Stock EDTA:

Add 1 mL of 0.5M stock EDTA pH8 for every liter of DPBS. Adjust pH of medium to 7.8±0.1 (final working pH is 8.0) if necessary. Note: pH units will usually rise 0.1-0.3 upon filtration. Filter with 0.1 micron filter.

1×DPBS/0.5 mM EDTA—pH8.0 Wash Procedures:

Stop the agitation, pH, DO, temperature controls if applicable. Let microcarrier beads settle for 15±5 minutes. Remove through the outlet port 80±10% of spent growth medium. See Table 15. Note: this procedure could be done using alternating tangential flow (ATF). Replace with equal volume of 1×DPBS/0.5 mM EDTA—pH8.0 wash solution to the culture vessel. See Table 15. Start the agitation to original setting and wash cells for 25±5 minutes. Stop the agitation and let microcarrier beads settle for 15±5 minutes. Remove through the outlet port 80±10% of wash solution. See Table 16. Note: this procedure could be done using the ATF. Add 1×DPBS/0.5 mM EDTA—pH8.0 wash solution to the vessel up to 50% of working culture volume. See Table 15. Set agitator speed to desired rpm. See Table 16. Start the agitator, pH, DO and temperature controls. Adjust the pH setting to 8.0. See Table 16.

TABLE 15

DPBS/0.5 mM EDTA - pH 8.0 Wash Volume and Agitation speed

| | Bioreactor working volume | | | |
|---|---|---|---|---|
| | 2 L | 5 L | 10 L | 15 L |
| Vol. to be removed (L) | 1.6 ± 0.2 | 4 ± 0.5 | 8 ± 1 | 12 ± 1.5 |
| Vol. to be added (L) | 1.6 ± 0.2 | 4 ± 0.5 | 8 ± 1 | 12 ± 1.5 |
| Agitation (rpm) | 175 | 175 | 134 | 134 |

TABLE 16

1X DPBS/0.5 mM EDTA pH 8.0 Wash Volume, Agitation speed, pH, Temp and DO settings

| | Bioreactor working volume | | | |
|---|---|---|---|---|
| | 2 L | 5 L | 10 L | 15 L |
| Vol. to be removed (L) | 1.6 ± 0.2 | 4 ± 0.5 | 8 ± 1 | 12 ± 1.5 |
| Vol. to be added (L) | 0.6 ± 0.2 | 1.5 ± 0.5 | 3.0 ± 1.0 | 4.5 ± 1.5 |
| Agitation (rpm) | 250 | 250 | 220 | 220 |
| pH | 8.0 ± 0.1 | 8.0 ± 0.1 | 8.0 ± 0.1 | 8.0 ± 0.1 |
| Temperature | 37 ± 0.1° C. | 37 ± 0.1° C. | 37 ± 0.1° C. | 37 ± 0.1° C. |
| DO | 50% | 50% | 50% | 50% |

Cell Detachment Procedure:

When the culture pH reached to 8±0.1, add calculated volume of 10× TrypLE to a final concentration of 0.05× through the injection port or through the medium port. See Table 17. Note: You can also perform 1:200 dilution of the 10× TrypLE relative to the desired working volume. Through the sampling port, take sample aliquots every 15±2 minutes until fully detached. Note: Cell detachment should be complete in <60 minutes. Add basal medium to the original working volume of the culture vessel. Stop all control loops except the agitator and pH controls.

Bead to Bead Procedure:

Transfer the desired volume of detached cells to final production reactor. See Table 18.

TABLE 17

10X TrypLE volumes

| | Bioreactor working volume | | | |
|---|---|---|---|---|
| | 2 L | 5 L | 10 L | 15 L |
| 10X TrypLE (mL) | 5 | 12.5 | 25 | 37.5 |

TABLE 18

Bead to Bead Process Transfer to Final Production Reactor

| | Bioreactor working volume | | | |
|---|---|---|---|---|
| 1:8 split | 2 L | 5 L | 10 L | 15 L |
| Vol. of trypsinized cells | 0.250 L | 0.625 L | 1.25 L | 1.875 L |
| Complete Growth medium | 1.725 L | 4.375 L | 8.75 L | 13.125 l |
| Cytodex3 microcarriers | 3.45 g | 8.75 g | 17.5 g | 26.25 g |

8.3 Example 3

Purification Process for Cell Culture Produced Influenza

The development of a robust large scale purification process for influenza produced in cell culture required intensive development. An early stage process was developed where the viral harvest (60-65 hours post infection) was pumped into a bag, and 10× sucrose phosphate (SP) buffer was added to the viral harvest (VH) bag at 1/10 (v/v) dilution for viral stabilization. The stabilized viral harvest (SVH) was first treated with Benzonase at 50 Units/mL with 2 mM MgCl2 at 32° C. for 3 hours to remove MDCK host cell DNA (HCD) and the reaction was stopped by addition of 5 mM EDTA. Benzonase is an engineered recombinant endonuclease that degrades DNA into oligonucleotides in the presence of magnesium ions. The Benzonase treated viral harvest was then clarified by a 1.2 μm Polypropylene (PP) and 0.45 μm PVDF capsule filters. The clarified VH was conditioned by 5-fold (5×) ultrafiltration and 5-fold diafiltration with SP buffer on a 500 kDa molecular weight cut-off hollow fiber cartridge. Virus particles would be retained in the retentate side, while host cell protein (HCP), host cell DNA (HCD) and Benzonase would be diafiltered to the permeate side of the hollow fiber. The concentrated and diafiltered virus was purified using a Cellufine Sulfate (CS) chromatography column to further remove HCD, HCP and Benzonase impurities. CS is an affinity resin that binds virus on the column and the bound virus is eluted using a SP high salt buffer. The purified virus from column eluate would be diafiltered by five diavolumes of SP100 (200 mM sucrose and 100 mM potassium phosphate, pH 7.2) buffer on a 500 kDa molecular weight cut-off hollow fiber cartridge to remove the high salt elution buffer and formulate the purified virus. The diafiltered virus product is then stabilized by addition of cGAG in 1/9 (v/v) dilution and sterile-filtered using a 0.22 μm filter to make the final bulk product.

Substantial changes were implemented to the initial process that improved the scalability, the efficiency of the process and the final product quality. Changes made in the process were based on the evaluation of recovery and level of impurities (HCD, HCP and Benzonase) and were implemented into the original established process. In all, five process steps were implemented to address scalability and to improve the efficiency of process and final product quality. First, the viral harvest what changed to 48 hours post infection for cells infected using a viral input of 2000 FFU/mL, this time corresponds to the peak viral titer. Second, the HCD removal step was changed from batch-mode Benzonase treatment to on-column Benzonase treatment. These two steps together improve the final product quality by significantly lowering the HCD level of the starting material and final bulk. Third, the loading concentration of the CS resin was increased from 9.0 $\log_{10}$FFU/mL to 9.5 $\log_{10}$FFU/mL, this reduces the production column size from 4 L to 1.4 L and improves the process efficiency. Fourth, the second buffer exchange volume was increased from 5 to 8 diavolumes to enhance Benzonase clearance. Fifth, the final filter flux was decreased by half to an average of 25 L/m$^2$ to avoid any plugging during final filtration during in the CTM runs. The final method (detailed below) provides a process that gives an average overall recovery of 43.4%, with 0.72 ng/dose (by PicoGreen) and 0.1 ng/dose (by PCR) HCD, 0.21 μg/dose HCP, and 0.0035 ng/dose Benzonase, all of which are below the specifications required by regulatory agencies. FIG. 10 provides an overview of the initial and improved purification processes.

8.3.1 Materials and Methods

Materials, Reagent and Equipment:

Other materials, equipment and reagents which perform similarly may be readily substituted.

1. 1.2 μm Polygard CN Opticap XL5 Filter (Millipore Corporation, Billerica, Mass., Cat. No. KN12A05HH1)
2. 0.45 μm Durapore Opticap XL4 Filter (Millipore Corporation, Billerica, Mass., Cat. No. KPHLAO4HH3)
3. 50 L Bag (Hyclone, Ltd, Logan, Utah, Cat. No. SH30712.04)
4. 10 L Bag (Hyclone, Ltd, Logan, Utah, Cat. No. SH30712.12)
5. Hollow Fiber, 500 KD, 4,800 cm$^2$ (GE Healthcare, Uppsala, Sweden, Cat. No. UFP-500-C-6A)
6. Hollow Fiber, 500 KD, 290 cm$^2$ (GE Healthcare, Uppsala, Sweden, Cat. No. UFP-500-C-3×2MA)
7. Cellufine Sulfate Resin (Chisso Corporation, Tokyo, Japan, Cat. No. 19847)
8. Flange O-ring (GE Healthcare, Uppsala, Sweden, Cat. No. 18-8494-01)
9. Adaptor O-ring (GE Healthcare, Uppsala, Sweden, Cat. No. 18-8475-01)
10. Bed support, 23 μm, end piece (GE Healthcare, Uppsala, Sweden, Cat. No. 18-9252-01)
11. Bed support, 23 μm, adaptor (GE Healthcare, Uppsala, Sweden, Cat. No. 18-1103-08)
12. Gaskets 25 mm i.d. 6 mm, EPDM (GE Healthcare, Uppsala, Sweden, Cat. No. 18-0019-27)
13. 4-port-2-way valves (GE Healthcare, Uppsala, Sweden, Cat. No. 18-5757-01)
14. Sartopore2 300 filter capsule, 0.45 μm/0.22 μm, 300 cm2 (Satorius, Mass., Cat. No. 5441307H5-00-B)
15. Sartopore2 150 filter capsule, 0.45 μm/0.22 μm, 150 cm2 (Satorius, Mass., Cat. No. 5441307H4-00-B)
16. 1 L PETG bottles (Nalgene, Rochester, N.Y.U, Cat. No. 2019-1000)
17. 2 L PETG bottles (Nalgene, Rochester, N.Y.U, Cat. No. 2019-2000)
18. MasterFlex platinum-cured silicone tubing L/S size 24 (Cole Parmer, Vernon Hills, Ill., Cat. No. 96410-24)
19. MasterFlex platinum-cured silicone tubing L/S size 36 (Cole Parmer, Vernon Hills, Ill., Cat. No. 96410-36)
20. 1 X Sucrose Phosphate buffer (Hyclone, Ltd, Logan, Utah, Cat. No. SH3A1577)-218 mM sucrose and 11 mM potassium phosphate, pH 7 buffer
21. 1XSP/1M NaCl buffer (Hyclone, Ltd, Logan, Utah, Cat. No. SH3A2034)
22. SP100 buffer (Hyclone, Ltd, Logan, Utah, Cat. No. SH3A1796)-200 mM sucrose and 100 mM potassium phosphate, pH 7.2 buffer
23. cGAG buffer (Hyclone, Ltd, Logan, Utah, Cat. No. SH3A1795)
24. Benzonase (EMD, Darmstadt, Germany, Cat. No. 1.01697.0002)
25. 1 M MgCl$_2$ (Sigma, St. Louis, Mo., Cat. No. M1028, lot #085K8920)
26. Quant-iT PicoGreen dsDNA kits (Invitrogen, Eugene, Oreg., Cat. No. P11496, lot #22987)
27. 0.5 N NaOH, diluted from 10 N NaOH (VWR, West Chester, Pa., Cat. No. VW3247-7)
28. Peristaltic Pump (Watson Marlow Inc., Wilmington, Mass., Models 520U, 520S and 520-Di)
29. WaveMixer (GE Healthcare, Uppsala, Sweden, Cat. No. Mixer20/50EH)
30. AKTA process Chromatography Skid (GE Healthcare, Uppsala, Sweden, Cat. No. 28409334)
31. Uniflux10 Filtration Skid (GE Healthcare, Uppsala, Sweden, Cat. No. 28920799)
32. BPG 100 Chromatography Column (GE Healthcare, Uppsala, Sweden, Cat. No. 18-1103-01)
33. BPG 200 Chromatography Column (GE Healthcare, Uppsala, Sweden, Cat. No. 18-1103-11)
34. Flexstand (GE Healthcare, Uppsala, Sweden, Cat. No. 56-4107-54)

TABLE 19

Viral Harvest Lots from Single Use Bioreactors (with 67% media exchange)

| Strain | Cell Culture Lot # | Purification Lots Run # | Harvest Hours post Infection |
|---|---|---|---|
| A/New Caledonia/20/99 | Sub 08012007-PP | 1 | 60-65 hr |
| A/Wisconsin67/05 | Sub 05012007-PD | 2 | 60-65 hr |
| A/Wisconsin67/05 | Sub 15012007-PP | 3 | 60-65 hr |
| A/New Caledonia/20/99 | Sub 19012007-PD | 4 | 60-65 hr |
| B/Malaysia2506/04 | Sub 22012007-PP | 5 | 60-65 hr |
| B/Malaysia2506/04 | Sub 26012007-PD | 6 | 60-65 hr |
| A/New Caledonia/20/99 | Sub 05022007-PP | 7 | 60-65 hr |
| A/Wisconsin67/05 | Sub 16022007-PD | 8 | 48 hr |
| B/Malaysia2506/04 | Sub 26022007-PP | 9 | 48 hr |

Cell Culture Viral Harvest (VH):

The detail of MDCK cell growth and virus production is described in International Patent Publication WO 08/105,931 (see in particular, Example 12). All the viral production runs were performed in a Single Use Bioreactor (SUB) with a 67% media exchange process and the cells were infected using a viral input of 2000 FFU/mL. Virus was harvested at approximately 60-65 hrs (runs 1-7) or 48 hours (runs 8-9) post infection of MDCK cells. Microcarriers in the SUB were allowed to settle for no less than 45 minutes prior to viral harvest (VH). Approximately 18 L of virus was pumped into a 50 L bag at approximately 0.2 L/min, and 2 L of 10×SP buffer was pumped into the same bag for stabilization of virus harvest (SVH). After mixing, samples were taken at SVH stages to test for infectivity by FFA, HCD and HCP assays.

Direct Flow Filtration 1 (DFF1):

A filter rig was prepared and autoclaved the day before viral harvest. The filter rig drawing showing the 1.2 μm Polygard CN polypropylene filter capsule and the 0.45 μm Durapore PVDF filter capsule is detailed in FIG. 9A, top panel. Approximately 20 L of SVH was pumped through the closed rig assembly at 1.5 Liter per Minute (LPM), and the filters were primed as the SVH passed through them. The total membrane surface area was 1800 cm$^2$ for the 1.2 μm Polygard CN polypropylene filter capsule and 1900 cm$^2$ for the 0.45 μm Durapore PVDF filter capsule. At a filtration flow rate of 1.5 LPM, the flux for the 1.2 μm and 0.45 μm filters were 500 Liter per m$^2$ area per hour (LMH) and 474 LMH, respectively. The actual loading for the 1.2 μm and 0.45 μm filters was 111 and 105 L/m2, respectively. The clarified filtrate was collected as DFF1 in a 20 L bag. The DFF1 filtrate was sampled and tested for infectivity by FFA, and for residual HCD and HCP.

Tangential Flow Filtration 1, 5× Ultrafiltration (UF)/5× DiaFiltration (DF) (TFF1):

Tubing rigs for the Uniflux skid were prepared and autoclaved the day prior to viral harvest. All the tubing rigs drawings are detailed in FIG. 9A, bottom panel. A Uniflux™ skid was used to perform the TFF1 step using the following operating parameters. The Uniflux skid is an automated membrane separations filtration system configured to operate hollow fiber cartridges. A 500 kDa of molecular weight cut-off (MWCO) hollow fiber with a 0.5 mm lumen size 4,800 cm$^2$ total membrane surface area and 60 cm path length was used. This process gives a final DFF1 loading of 41.7 L/m$^2$ membrane surface area which is in the optimal range of 40-150 L/m2 for the TFF1 process as previously evaluated. For runs 1-6, the same hollow fiber cartridge was cleaned post process and reused. For runs 7-9, a new hollow fiber was prepared and used for each run. New hollow fiber cartridges were prepared by rinsing with deionized (DI) water for 90 mins to remove the glycerol preservative, sanitized with 0.5 N NaOH for 1 hour and equilibrated with 1×SP buffer until the pH is 7.0 before each run. The entire 5XUF/5XDF process was operated using the Uniflux skid programmed at a constant shear rate of 16000 s$^{-1}$ and at a constant TMP of 20 psi.

The entire volume of DFF1 was processed through the Uniflux skid. Approximately 5 L of the DFF1 was first pumped into the Uniflux process tank. The permeate line was closed initially to establish a recirculation (retentate) flow rate of 8.6 L/min, which is equivalent to a shear rate of 16,000 s$^{-1}$. After 5 minutes of recirculation, the 5XUF process was started. The permeate line was opened to allow impurities smaller than 500 kDa such as HCP and DNA to pass through the membrane, while the retentate control valve gradually closed to achieve a transmembrane pressure (TMP) set point of 1.4 bar (20.3 psi). The remaining DFF1 filtrate was continuously pumped into the process tank to maintain a constant tank level of 5±0.1 L until the entire volume of DFF1 was fed into the tank. After all the DFF1 material was fed, the feed pump was stopped and the retentate continued to concentrate until the final retentate volume reached 4 L or 16 L of permeate was collected. The 4 L retentate (5XUF) was diafiltered by buffer exchange with 5× diavolumes of 1×SP buffer (20 L) and the process operated at the same shear rate and TMP as described above. The diafiltration buffer line was opened and the feed pump was started again to pump in 1×SP buffer. 5XDF process ended after 20 L of diafiltration permeate was collected. At the end of 5XDF, the retentate control valve was completely opened and the permeate line closed again to allow system recirculation to sweep off any recoverable virus that was weakly bound on the surface of the hollow fiber membrane during the process. The retentate, which contained the concentrated and diafiltered virus product, was drained and collected into a 10 L product bag. For the last two purification runs (8 and 9), an additional buffer rinse step was introduced after retentate collection. Approximately 1.5 L of 1×SP was pumped into the process tank and recirculated for another 5 minutes with the permeate line closed. This buffer rinse was also collected into the same 10 L product bag and the bag was labeled as 5XUF 5XDF TFF1 product and the total volume was approximately 5.5 L. The TFF1 product was sampled to test for infectivity by FFA, and HCD and HCP. The hollow fiber cartridge and Uniflux system were cleaned after each process run with 0.5 N NaOH for 1 hr using a recirculation flow rate of 8.6 L/min.

Packing of BPG 100/200 Cellufine Sulfate (CS) Column and Column Evaluation:

CS resin was stored in 20% ethanol at approximately 50% slurry. The amount of resin required to pack a BPG 100 or BPG 200 column was calculated using a compression ratio of 1.1. The amount of resin as calculated was prepared by performing a two times buffer exchange with 1× buffer, followed by one time buffer exchange with 1×SP/1M NaCl buffer.

The BPG 100 and BPG 200 columns were assembled according to the manufacturer's instructions. An empty column was prepared, sanitized with 0.5 N NaOH and rinsed with DI water before use. 1×SP buffer was used to flow-pack the CS resin into a BPG 100 column at 500 cm/hr to generate a column bed height of 15-20 cm (target 17.5 cm) using the AKTA process™ skid. The AKTA process is an automated liquid chromatography system.

The prepared resin slurry in 1×SP/1M NaCl buffer was poured along the side wall of the empty column and any residual resin remaining on the wall was rinsed off with water in a squirt bottle. The resin was allowed to settle to a resin bed height of at least 10 cm below the liquid level. The top adaptor was inserted in the column without disrupting the resin bed and then secured with retaining screws/nuts. A 4-port-2-way valve (4-2 valve) was installed at the column inlet. The four different ports were connected as follows:

1—AKTA process system column inlet
2—Column manual purge (connected to waste or recirculation line)
3—Spike test connector (a female lure lock used to inject high salt solutions for HETP test)
4—BPG 100/200 Column Inlet The BPG100 column bottom outlet was then connected to the AKTA system column outlet. Before lowering the column adaptor, the connections for the 4-2 valve, ports 3 and 4 were checked. The top adaptor was slowly lowered into the resin bed and a small volume of buffer was purged from port 3 of the 4-2 valve. This ensured that the inlet of the top adaptor was purged with buffer.

The 4-2 valve was then switched to connect ports 1 and 2. The 1×SP buffer was connected to the AKTA system inlet and flow was started at 500 cm/hr first to bypass the column at this point through the column purge port (port 2 on 4-2 valve). When the flow rate reached 500 cm/hr on the flow meter, the 4-2 valve was quickly adjusted so that ports 1 and 4 were connected. When the resin bed reached the target bed height, the adaptor closer was lower to resin bed. These steps were repeated until there was no change in resin bed height and the adaptor reached the resin bed. The adaptor was further lowered 1-3 mm to compress the resin bed to avoid any headspace between adaptor and resin bed.

Before the packing evaluation, the CS column was equilibrated with 1×SP to establish a stable conductivity baseline. Column packing was evaluated by injecting 1×SP/1M NaCl at 2% of the column volume (CV) using the spike test connector (port 3 to 4 on 4-2 valve). The column was equilibrated with 1×SP at flow rate of 50 cm/hr (port 1 to 4 on 4-2 valve). The conductivity peak appeared at approximately ½ the CV. The resulting conductivity peak on the Unicorn software was used to evaluate the column plate height (HETP) and peak asymmetry. Once the desired column HETP was reached, the column was sanitized and stored in 0.5 N NaOH before use.

Cellufine Sulfate Chromatography (CS):

Tubing rigs for the AKTA Process skid were prepared and autoclaved the day prior to viral harvest. All the tubing rigs drawings are detailed in FIG. 9B, top panel. The entire chromatography process was automated by programmed method.

All flow paths of AKTA process skid were manually equilibrated with 1×SP before each run. At the start of the process, the column was first equilibrated with 3 column volumes (CV) of 1×SP at a linear flow rate of 150 cm/hr. The entire volume of 5XUF 5XDF TFF 1 was then loaded onto the column and unbounded material was collected as flow through. After loading, the column was washed with 1 CV of 1×SP at 150 cm/hr followed by 2.5 CV of 1×SP containing 50 U/mL Benzonase and 2 mM $MgCl_2$ (1×SPB) at 50 cm/hr for on-column Benzonase treatment. The decreased linear flow rate and calculated 1×SPB wash volume allowed the column resin to have a Benzonase contact time of 50 minutes. The column was then washed with 1 CV of 1×SP at 50 cm/hr to replace the last CV of 1×SPB on-column Benzonase treatment and an additional 1 CV of 1×SP at 150 cm/hr. The bound virus was eluted form the column with 3 CV of 1×SP/1M NaCl buffer. The CS eluate was collected in a 10 L bag and the collection of the elution peak was based on UV absorbance ($A_{280}$ reading from 50 mAU to 50 mAU (0.1 O.D. to 0.1 O.D.) using 5 mm path length UV flow cell). The CS elution volume from BPG 100 column is approximately 0.6 to 0.9 L. The column and AKTA process system were sanitized with 0.5 N NaOH after each process run. The column load, flow through, wash and eluate were sampled to test for infectivity by FFA, Benzonase, HCD and HCP.

Tangential Flow Filtration 2, 8×DF (TFF2):

The setup and use of Flexstand was performed according to the manufacturer's directions. A 500 kDa MWCO hollow fiber with a 0.5 mm lumen size, 60 cm path length and 290 $cm^2$ total membrane surface area was used. With this size membrane area and the volume of CS elute described above, the final loading was in the range of 20-50 $L/m^2$ membrane surface area, which is the optimal range for the TFF2 process as previously evaluated. A new hollow fiber was setup on the Flexstand the day before viral harvest. The hollow fiber was rinsed with DI water for 90 minutes to remove the glycerol preservative, sanitized with 0.5 N NaOH for 1 hr and equilibrated with SP 100 buffer until the pH reached 7.2.

The entire volume of CS eluate was processed through the Flexstand system. The permeate line was closed initially to allow recirculation of the CS eluate at a feed flow rate of 0.5 L/min to generate a shear rate of 16,000 $s^{-1}$. After recirculation for 5 minutes, the permeate line was opened to start diafiltration. At the same time, SP100 buffer was pumped through the diafiltration line and the retentate control valve was gradually to obtain a transmembrane pressure (TMP) of 20-21 psi. The volume of the retentate reservoir was kept constant at a volume equal to the CS elution volume (range from 0.4-0.8 L) for the entire process by controlling the pump flow rate of the SP100 diafiltration line. Before run 8, the CS eluate was diafiltered with 5× diavolumes of SP 100 buffer. The CS eluate was buffer exchanged with the 8× diavolumes of SP100 buffer for purification runs 8-9. At the end of diafiltration, the retentate valve was completely opened and the permeate line closed again to allow for system recirculation for 5 minutes before product recovery. The diafiltered product was drained into a 10 L product bag. The diafiltered product was sampled to test for infectivity by FFA, Benzonase, HCD and HCP. The hollow fiber cartridge and system were cleaned with 0.5 N NaOH for 1 hr at a recirculation flow rate 0.5 L/min.

Direct Flow Filtration 2 (DFF2):

The filter rig was prepared and autoclaved the day before viral harvest. The filter rig drawing is detailed in FIG. 9B, bottom panel. The 0.22 lam polyether sulfone membrane capsule used had a total surface area of 150 $cm^2$ for runs 1-5 and 300 $cm^2$ for runs 6-9. The final sterile filtration DFF2 step was performed in the biosafety cabinet.

Concentrated Glutamate Arginine Gelatin (cGAG) was added to the 8×DF product at a 1:9 (v/v) dilution to make the final formulation of the purified virus. The formulated virus was pumped through the closed rig assembly at approximately 0.38 LPM for the 300 $cm^2$ capsule, and the filter was primed using the final product. The filtrate was collected in sterile 2 L bottles as the final bulk product. At a filtration flow rate of 0.38 LPM, the flux for the 300 $cm^2$ filters was 760 LMH. The formulated bulk loading to the membrane area was in the range of 20-150 $L/m^2$. The 0.22 µm filtered final bulk product was sampled to test for infectivity by FFA, Benzonase, HCD and HCP levels. The final bulk product was aliquoted into several 1-, 10- and 100-mL aliquots and flash frozen and stored in −80° C.

Sample Analysis and Calculations:

All the samples sent for analysis were flashing frozen and stored in −80° C. HCP assays were done essentially as described below. The HCD assay was done using the PicoGreen and PCR methods essentially as described below. HCD sizing was analyzed by direct label method of psoralen-biotin (blot) and direct staining in agarose gels. Benzonase quantification assay was essentially as described below. All values that are calculated ng or µg per dose are based on titer of 7 $log_{10}$FFU per dose (one dose is also commonly referred to as $10^7$ FFU).

Residual Host Cell DNA Determinations:

Residual MDCK host cell DNA is quantified using a microwell-format real-time PCR method. The target of the assay is a unique sequence within the cytochrome oxidase subunit I (Cox I) gene of dogs. Using a set of optimized oligonucleotide primers, a MDCK Cox I specific PCR product is generated from template and detected by the SYBR® Green dye. The microwell format accommodates DNA calibrators across a wide dynamic range (1000 to 0.1 ng/ml). Appropriate positive and negative controls are included in each assay. Test sample DNA are derived using a DNA extraction kit. Sample DNA quantities above the lower limit of quantification of 0.1 ng/ml will be calculated from the standard curve. Accuracy will be within 75 to 125% based on recovery of the spike control. The reported results will be the mean DNA quantity of the sample extraction replicates that yield spike recovery values of 50 to 150%.

Residual Host Cell Protein Determinations:

The residual host cell (MDCK) protein (HCP) are determined by an Enzyme-Linked Immunosorbent Assay (ELISA) using a primary biotinylated rabbit antibody produced against HCP (from an uninfected MDCK culture) and streptavidin-horse radish peroxidase (HRPO) conjugate. Antibodies against MDCK cell lysate are absorbed onto a polystyrene microplate. A blocking solution containing bovine serum albumin is added to saturate the excess binding sites. When a dilution of test article sample is added to the coated plate, the MDCK HCP, if present, will bind to the coated antibodies. A primary biotin-labeled antibody against MDCK lysate raised in rabbits is added to the plate, followed by horse radish peroxidase (HRPO) labeled streptavidin conjugate. Finally, the HRPO substrate is added and an ELISA plate reader is used to measure the intensity of the colored end product formed. The intensity of the color developed is proportional to the amount of MDCK HCP present in the test article. A standard curve is generated from the MDCK cell lysate calibrator of known protein concentration. From a standard curve, the protein concentration of MDCK cell lysate is determined.

Residual Benzonase Determinations:

The Benzonase activity is determined by its ability to cleave herring sperm DNA. The test article, in duplicate, is compared against a Benzonase standard curve, in which readings are measured with a spectrophotometer at 260 nm. The percent spike recovery (Benzonase activity) is calculated to determine the net Benzonase U/ml. The net Benzonase activity of a spiked reference standard should be between 1.1 and 1.9 U/ml, the coefficient of correlation should be ≥0.995, the activity in an unspiked sample dilution should be ≥0.7 U/ml for the activity to be quantifiable, and the percent spike recovery should be between 80 and 120%.

8.3.2 Results and Discussion

All the SUB runs showed harvest titer range from 8.0 to 8.6 log 10FFU/mL. The recovery, HCD and HCP results used to evaluate the performance of each purification runs are summarized in Table 20, Table 21, and Table 22. The following sections will summarize and discuss the changes made to improve the process efficiency and the final product quality. The process development for the initial and final purification schemes are summarized in FIG. 10, which shows the major changes from early purification runs to the last purification runs.

TABLE 20

Summary of Recovery for Purification Runs 1-9

| | Purification Run | | | | | | | | |
|---|---|---|---|---|---|---|---|---|---|
| | 1 | 2 | 3 | 4 | 5 | 6 | 7 | 8 | 9 |
| Strain | A/NC | A/Wis | A/Wis | A/NC | B/Mal | B/Mal | A/NC | A/Wis | B/Mal |
| Harvest (hr) | 60-65 | 60-65 | 60-65 | 60-65 | 60-65 | 60-65 | 60-65 | 48 | 48 |
| CS Column | BPG200 | BPG200 | BPG200 | BPG200 | BPG200 | BPG100 | BPG100 | BPG100 | BPG100 |
| CS Loading ($\log_{10}$/mL Gel) | N/A | 8.3 | 8.7 | 8.7 | 8.4 | 9.2 | 9.1 | 9.3 | 9.0 |
| Process* | 1a | 1a | 1a | 1a | 1b | 1b | 1b | 1b | 1b |
| Titer (VH-CC) | 8.3 | 8.4 | 8.4 | 8.4 | 8.3 | 8.6 | 8.4 | 8.6 | 8.0 |
| Titer (VH-P) | 7.9^ | 7.7^ | 8.4 | 8.6 | 8.1 | 8.3 | 8.3 | 8.4 | 7.9 |
| DFF1 | 99.1% | 154.6% | 79.4% | 52.7% | 124.1% | 124.3% | 124.2% | 78.3% | 123.1% |
| TFF1 | 107.2% | 73.8% | 50.9% | 53.4% | 30.3% | 42.2% | 74.5% | 80.0% | 76.1% |
| CS Eluate | N/A | 54.9% | 81.4% | 19.0% | 60.8% | 40.0% | 37.0% | 96.8% | 60.5% |
| TFF2 | N/A | 110.1% | 73.9% | 106.9%§ | 125.9%§ | 150.8% | 94.0% | 64.0%† | 92.0%† |
| DFF2 | N/A | 88.3%# | 111.1%# | 110.8%# | 88.3%# | 69.8% | 65.8% | 78.4% | 108.0% |
| Final Titer | N/A | 8.3 | 8.5 | 8.5 | 8.5 | 8.9 | 8.6 | 9.2 | 9.0 |
| Overall Yield | N/A | 60.9% | 27.0% | 6.3% | 25.4% | 22.0% | 21.2% | 30.4% | 56.3% |

VH-CCD: virus harvest cell culture,
VH-PD: virus harvest purification
*1a: Benzonase treatment in SVH bag; 1b: Benzonase treatment on column
^FFA assay based on Anti-NA instead of Anti-HA
§1400 cm2 hollow fiber (290 cm2 hollow fiber for the rest)
150 cm2 filter (300 cm2 filter for runs 6 through 9)
†8X DF (5X DF for the rest)
Several of the process changes are indicated in BOLD

TABLE 21

Summary of HCD for Purification Runs

| | Run | | | | | | | | | |
|---|---|---|---|---|---|---|---|---|---|---|
| | 2 | | 3 | | 4 | | 5 | | 6 | |
| Strain | A/Wis | | A/Wis | | A/NC | | B/Mal | | B/Mal | |
| Harvest (hr) | 60-65 | | 60-65 | | 60-65 | | 60-65 | | 60-65 | |
| Column | BPG200 | | BPG200 | | BPG200 | | BPG200 | | BPG100 | |
| Process* | 1a | | 1a | | 1a | | 1b | | 1b | |
| DNA Level | ng/mL | ng/dose | ng/mL | ng/dose | ng/mL | ng/dose | ng/mL | ng/dose | ng/mL | ng/dose |
| SVH | 3228.8 | 644.2 | 7200 | 286.6 | 5480 | 137.7 | 3821 | 303.5 | 5720 | 286.7 |
| DFF1 | 2910 | 366.3 | 3920 | 196.5 | 1720 | 86.2 | 5328 | 336.2 | 4120 | 164 |
| TFF1 | 2520 | 126.3 | 1940 | 38.7 | 1610 | 32.1 | 14000 | 557.4 | 28200 | 562.7 |
| CS Eluate | 1204.9 | 47.97 | 537.4 | 10.72 | 146.1 | 14.6 | 37.8 | 1.2 | 135^ 118.9 | 1.7^ 1.5 |
| TFF2 (5X) | 928.3 | 36.96 | 385.9 | 12.2 | 144 | 4.56 | 57.1 | 1.43 | 159.9 | 1.27 |
| TFF2 (8X) | | | | | | | | | | |
| DFF2 | 807.8 | 40.49 | 365.6 | 11.56 | 29^ 102.9 | 0.92^ 3.25 | 38.1 | 1.21 | 18.6^ 69.9 | 0.23^ 0.88 |

TABLE 21-continued

Summary of HCD for Purification Runs

| | | Run | | | | | |
|---|---|---|---|---|---|---|---|
| | | 7 | | 8 | | 9 | |
| | Strain | A/NC | | A/Wis | | B/Mal | |
| | Harvest (hr) | 60-65 | | 48 | | 48 | |
| | Column Process* | BPG100 1b | | BPG100 1b | | BPG100 1b | |
| | DNA Level | ng/mL | ng/dose | ng/mL | ng/dose | ng/mL | ng/dose |
| | SVH | 10800 | 541.3 | 3440 | 136.9 | 2070 | 260.6 |
| | DFF1 | 4490 | 178.8 | 1440 | 72.17 | 1060 | 106 |
| | TFF1 | 17100 | 171 | 3690 | 73.63 | 1690 | 67.28 |
| | CS Eluate | 123^ | 1.55^ | 91.2 | 0.29 | 150.5 | 1.51 |
| | | 82 | 1.03 | | | | |
| | TFF2 (5X) | 72.1 | 1.14 | 135 | 0.54 | 190 | 1.9 |
| | TFF2 (8X) | | | 16.8^ | 0.067^ | 34.8^ | 0.35^ |
| | | | | 128.8 | 0.65 | 161.4 | 1.6 |
| | DFF2 | 7.2^ | 0.18^ | 5^ | 0.032^ | 16.4^ | 0.164^ |
| | | 56.6 | 1.42 | 93.8 | 0.59 | 83.7 | 0.84 |

*1a: Benzonase treatment in bag; 1b: Benzonase treatment on column

^HCD assay based on real time PCR, The Picogreen assay was also performed for runs 2 thorough 9
Several of the process changes are indicated in BOLD

TABLE 22

Summary of HCP for Purification Runs 2-9

| | Run | | | | | | | | | | | | | | | |
|---|---|---|---|---|---|---|---|---|---|---|---|---|---|---|---|---|
| | 2 | | 3 | | 4 | | 5 | | 6 | | 7 | | 8 | | 9 | |
| Strain | A/Wis | | A/Wis | | A/NC | | B/Mal | | B/Mal | | A/NC | | A/Wis | | B/Mal | |
| Harvest (hr) | 60-65 | | 60-65 | | 60-65 | | 60-65 | | 60-65 | | 60-65 | | 48 | | 48 | |
| Column Process* | BPG200 1a | | BPG200 1a | | BPG200 1a | | BPG200 1b | | BPG100 1b | | BPG100 1b | | BPG100 1b | | BPG100 1b | |
| HCP Level | µg/mL | µg/dose | µg/mL | µg/dose | µg/mL | µg/dose | µg/mL | µg/dose | µg/mL | µg/dose | µg/mL | µg/dose | µg/mL | µg/dose | µg/mL | µg/dose |
| SVH | 278 | 55.5 | 392 | 15.6 | 269 | 6.76 | 231 | 18.35 | 250 | 12.53 | 233 | 11.68 | 135 | 5.37 | 174 | 21.9 |
| DFF1 | | | 369 | 18.5 | | | 329 | 20.76 | | | | | 83.7 | 4.19 | 140 | 14 |
| TFF1 | 82.3 | 4.12 | 382 | 7.62 | 68.2 | 1.36 | 345 | 13.73 | 108.7 | 2.17 | 86.8 | 0.87 | 24.3 | 0.48 | 27 | 1.07 |
| CS Eluate | 15.7 | 0.63 | 258 | 5.15 | 46.6 | 4.66 | 209 | 6.61 | 157 | 1.98 | 188 | 2.37 | 67.2 | 0.21 | 98.1 | 0.98 |
| TFF2 (5X) | 51 | 2.56 | 142 | 4.49 | 69.1 | 2.19 | 149 | 3.74 | 60.3 | 0.48 | 42.1 | 0.67 | 46.3 | 0.18 | 81.9 | 0.82 |
| TFF2 (8X) | | | | | | | | | | | | | 42.1 | 0.21 | 79 | 0.79 |
| DFF2 | 22 | 1.1 | 17.6 | 0.56 | 32.7 | 1.03 | 27.3 | 0.86 | 49.8 | 0.63 | 23.8 | 0.6 | 20.9 | 0.13 | 29.3 | 0.29 |

*1a: Benzonase treatment in bag; 1b: Benzonase treatment on column

TABLE 23

Overall DNA Clearance for Purification Runs 2-9

| SVH Batch-mixed | | | | | CS On-Column | | | | |
|---|---|---|---|---|---|---|---|---|---|
| Run # | Column Used | % DNA Remaining | Final Bulk DNA Level (ng/dose) | Vol. of 50 U/mL Benzonase | Run # | Column Used | % DNA Remaining | Final Bulk DNA Level (ng/dose) | Vol. of 50 U/mL Benzonase |
| 2 | BPG 200 | 3.36% | 40.49 | 20 L | 5 | BPG 200 | 0.10% | 1.21 | 13 L |
| 3 | BPG 200 | 1.09% | 11.56 | 20 L | 6 | BPG 100 | 0.07% | 0.88 | 3.5 L |
| 4 | BPG 200 | 0.15% | 3.25 | 20 L | 7 | BPG 100 | 0.02% | 1.42 | 3.5 L |
| | | | | | 8 | BPG 100 | 0.11% | 0.59 | 3.5 L |
| | | | | | 9 | BPG 100 | 0.15% | 0.84 | 3.5 L |

TABLE 24

Summary of Residual Benzonase for Purification Runs 2-9

| | Run 2 | | Run 3 | | Run 4 | | Run 5 | | Run 6 | | Run 7 | | Run 8 | | Run 9 | |
|---|---|---|---|---|---|---|---|---|---|---|---|---|---|---|---|---|
| Strain | A/Wis | | A/Wis | | A/NC | | B/Mal | | B/Mal | | A/NC | | A/Wis | | B/Mal | |
| Harvest (hr) | 60-65 | | 60-65 | | 60-65 | | 60-65 | | 60-65 | | 60-65 | | 48 | | 48 | |
| Column | BPG200 | | BPG200 | | BPG200 | | BPG200 | | BPG100 | | BPG100 | | BPG100 | | BPG100 | |
| Process* | 1a | | 1a | | 1a | | 1b | | 1b | | 1b | | 1b | | 1b | |
| Benzonase Level | ng/mL | ng/dose | ng/mL | ng/dose | ng/mL | ng/dose | ng/mL | ng/dose | ng/mL | ng/dose | ng/mL | ng/dose | ng/mL | ng/dose | ng/mL | ng/dose |
| SVH | | | 0.35 | 0.014 | 0.06 | 0.002 | | | 0.18 | 0.009 | ND | | 0.12 | 0.005 | 0.14 | 0.0176 |
| DFF1 | 70.9 | 8.926 | 50 | 2.506 | 46 | 2.306 | | | ND | | ND | | 0.09 | 0.005 | 0.066 | 0.007 |
| TFF1 | | | 2 | 0.04 | 9 | 0.18 | 0.07 | 0.003 | ND | | ND | | 0.12 | 0.002 | 0.11 | 0.004 |
| 1CV post SPB wash | | | | | | | 0.078 | | | | | | 0.15 | | 0.28 | |
| 2CV post SPB wash | | | | | | | 0.12 | | | | | | 0.21 | | 0.15 | |
| 3CV post SPB wash | | | | | | | 0.26 | | | | | | 0.33 | | 0.14 | |
| 4CV post SPB wash | | | | | | | 0.28 | | | | | | | | 0.05 | |
| CS Eluate | | | | | 7.8 | 0.78 | 89 | 2.814 | >75 | >0.944 | 4.2 | 0.053 | 221.7 | 0.701 | 192 | 1.92 |
| TFF2 (5X DF) | | | 0.54 | 0.017 | 0.66 | 0.021 | 5.1 | 0.128 | 6.6 | 0.052 | 0.6 | 0.01 | 1.62 | 0.006 | 1.38 | 0.0138 |
| TFF2 (8X DF) | | | | | | | | | | | | | 0.36 | 0.002 | 0.45 | 0.005 |
| DFF2 | 0.9 | 0.045 | 0.21 | 0.007 | 0.69 | 0.022 | 2.1 | 0.066 | 6.6 | 0.083 | 3.6 | 0.09 | 0.27 | 0.002 | 0.52 | 0.005 |

*1a: Benzonase treatment in bag; 1b: Benzonase treatment on column
Several of the process changes are indicated in BOLD

TABLE 25

Summary of Process Attributes for all Purification Runs

| | Purification Run | | | | | | | |
|---|---|---|---|---|---|---|---|---|
| | 2 | 3 | 4 | 5 | 6 | 7 | 8 | 9 |
| Strain | A/Wis | A/Wis | A/NC | B/Mal | B/Mal | A/NC | A/Wis | B/Mal |
| Harvest (hr) | 60-65 | 60-65 | 60-65 | 60-65 | 60-65 | 60-65 | 48 | 48 |
| Column | BPG200 | BPG200 | BPG200 | BPG200 | BPG100 | BPG100 | BPG100 | BPG100 |
| Loading (log10FFU/mL Gel) | 8.3 | 8.7 | 8.7 | 8.4 | 9.2 | 9.1 | 9.3 | 9 |
| Process* | 1a | 1a | 1a | 1b | -1b | 1b | 1b | 1b |
| VH Titer (CCD) | 8.4 | 8.4 | 8.4 | 8.3 | 8.6 | 8.4 | 8.6 | 8.0 |
| VH Titer (PD) | 7.7^ | 8.4 | 8.6 | 8.1 | 8.3 | 8.3 | 8.4 | 7.9 |
| Final Bulk Titer | 8.3 | 8.5 | 8.5 | 8.5 | 8.9 | 8.6 | 9.2 | 9.0 |
| Overall Yield§ | 60.9% | 27.0% | 6.3% | 25.4% | 22.0% | 21.2% | 30.4% | 56.3% |
| VH HCD (ng/mL) | 3229 | 7200 | 5480 | 3821 | 5720 | 10800 | 3440 | 2070 |
| Bulk HCD (ng/dose) PicoGreen | 40.49 | 11.56 | 3.25 | 1.21 | 0.88 | 1.42 | 0.59 | 0.84 |
| Bulk HCD (ng/dose) rtPCR | n/a | n/a | 0.92 | n/a | 0.23 | 0.18 | 0.032 | 0.164 |
| VH HCP (g/mL) | 278 | 392 | 269 | 231 | 250 | 233 | 135 | 174 |
| Bulk HCP (g/dose) | 1.1 | 0.56 | 1.03 | 0.86 | 0.63 | 0.6 | 0.13 | 0.29 |
| Benzonase (ng/dose) | 0.045 | 0.007 | 0.022 | 0.066 | 0.083 | 0.09 | 0.002 | 0.005 |

*1a: Benzonase treatment in bag; 1b: Benzonase treatment on column
^FFA assay based on Anti-NA instead of Anti-HA
§Based on VH-PD titer
Several of the process changes are indicated in BOLD SVH—Change in Benzonase Treatment from SVH to On-Column Benzonase Treatment:

In the initial process, Benzonase treatment was performed at the SVH step to remove host cell DNA. This process step involved mixing 20 L of SVH with 50 U/mL Benzonase for three hours at 32° C. before performing the DFF1 step. In purification runs 1 to 4, Benzonase was added to SVH step while in purification runs 5 to 9, the Benzonase treatment was eliminated from the SVH step and performed as an on-column Benzonase treatment process during the CS chromatography step using a chromatography buffer that contained 50 U/mL of Benzonase and a resin contact time of 50 minutes. As shown in Table 21, purification runs 2 to 4, the HCD level was not reduced noticeably in terms of ng per dose between the SVH and DFF1; however, in purification runs 5 to 9, the HCD level was appreciably reduced after the Benzonase-on column CS chromatography step. The HCD level of final bulk product analyzed by both PCR and PicoGreen was found to be much lower for purification runs 5 to 9 (0.84-1.42 ng/dose) relative to purification runs 1 to 4 (3.25-40.49 ng/dose). This change not only improved the final product quality by lowering the final bulk HCD to a level less than or equal to 1 ng/dose but also increased the process efficiency by reducing the Benzonase treatment time and the total amount of Benzonase required. The impact of on-column Benzonase treatment will be further discussed in the CS chromatography section.

DFF1:

As shown in Table 20, the DFF1 step showed good recovery (78.3-154.6%) except for run 4 (52.7%). The DFF1 step removed the cells and cell debris and usually showed no loss in titer. This step also removed some amount of HCD (Table 21) but not HCP (Table 22). The membrane area of both filters (1.2- and 0.45-μm) used to filter 20 L of SVH was based on the capacity of both filters and was previously determined from a scale-down Vmax/Pmax studies using a safety factor of 2.6 and 1.5, respectively. For a filtration flow rate of 1.5 LPM, the flux for the 1.2 μm and 0.45 μm filters were 500 LMH and 474 LMH, respectively. The actual SVH loading for the 1.2 μm and 0.45 μm filters was 111 and 105 L/m$^2$, respectively.

TFF1—Changes in Setup and Recovery Method to Improve Step Recovery of TFF 1:

The first six purification runs showed a gradual loss in potency recovery at the TFF 1 step for each run from 107.2% to 30.3% (Table 20). For purification runs 1 to 6, the TFF1 hollow fiber cartridge was cleaned with 0.5 N NaOH and reused and after the process. It is unknown whether the cleaning efficiency of the hollow fiber cartridge was sufficient enough to completely remove the gel layers after each run and this could result in a decrease in virus recovery after this process step. To generate a more consistent step recovery, three major changes were implemented to the existing protocol beginning with purification run 7. First, a new hollow fiber was used for each run to eliminate the possibility of insufficient cleaning of the hollow fiber. Second, the concentrated retentate was recirculated in the hollow fiber cartridge for 5 minutes with retentate valve open and permeate valve closed before the TFF1 product was collected. This removed any potential gel layer that may have formed on the surface of membrane during the concentration and diafiltration process and allowed recovery. Third, an additional buffer rinse step was performed with the same recirculation flow rate and time (5 minutes) to recover residual virus in the hollow fiber cartridge and the buffer rinse was collected together with the product. After these implemented changes, the step recovery of TFF1 remained consistently high, approximately 75-80%, for purification runs 7 to 9 (Table 20). FIG. 11 shows a typical flux curve for the TFF1 process from performed at 16000 s$^{-1}$ shear rate and constant TMP at 20 psi (purification run 8). The flux decreased as the virus solution became more concentrated (5XDF) and it continued to decrease when the diafiltration step began but increased slightly toward the end of diafiltration step (5XDF). The flux ranged from 70-100 LMH for all purification runs and appeared to be related to the virus titer and the turbidity of the DFF1 filtrate. The slight increase in flux at the end of the diafiltration step was probably due to the additional removal of HCP and HCD impurities at the end of 5XDF. As shown in Table 22, the majority (80-90%) of the HCP impurities were removed at the 1$^{st}$ TFF (TFF1) step because any HCP smaller than 500 kDa should be removed in the permeate. The completion of the buffer exchange of virus harvest to the 1×SP was shown in the conductivity trace decreased from 12.5 mS/cm to 1 mS/cm at the end of 5XDF process (FIG. 11).

CS on-Column Benzonase Treatment to Increase HCD Removal:

The initial experiments were designed using a small scale CS column with bed height of 10 cm and a virus loading concentration of approximately 9.0 log$_{10}$FFU per mL of resin. As the process was improved, the loading concentration of virus per mL of resin, the linear flow rate and the column bed height were linearly scaled. At a loading titer of 9.0 log$_{10}$FFU/mL resin, a 4 L bed volume of CS would be required to process 20 L of stabilized virus harvest with a harvest titer of 8.3 log$_{10}$FFU/mL. In development runs 1 to 5, 4 L of CS resin was packed into a BPG 200 column (20 cm inner diameter (i.d.)) to a final bed height of 12.5 cm. During the packing of the BPG 200 column at 200 cm/hr, the back pressure exceeded the recommended packing pressure of 2.5 bar pressure. (FIG. 12). A dynamic binding capacity study was performed and that showed that CS resin could actually bind up to approximately 9.7 log$_{10}$FFU/mL resin under the packing conditions described above. As such, at a virus loading of 9.5 log$_{10}$FFU/mL of resin, only 1.3 L of CS resin would be required to process 20 L of stabilized virus harvest with a harvest titer of 8.3 log$_{10}$FFU/mL.

A BPG 200 column packed with 1.3 L of CS resin results in a final column bed height of 4.5 cm. A dramatic reduction in the column bed height gives a lower resolution compared to a packed column with a bed height of 15-20 cm (typical for large-scale processes). Starting from purification run 6, a BPG 100 column was packed to a target bed height of 17.5 cm+/−2.5 cm to give a CS column volume of 1.4 L. For the BPG 100 column, a packing flow rate of 500 cm/hr was used and the resultant packing pressure did not exceed the recommended packing pressure limit of the resin, which is different than packing pressure for the BPG 200 column (FIG. 12).

Comparing purification runs 6 to 9 (BPG 100) with purification runs 2 to 5 (BPG 200), a similar CS eluate step recovery averaging 54% and 59%, respectively, when the actual loading was increased from 8.4-8.9 log$_{10}$FFU/mL resin (BPG 200 column) and 9-9.3 log$_{10}$ FFU/mL resin (BPG 100 column) (Table 20). In terms of column performance for HCD removal as performed using the on-column Benzonase treatment, purification runs 6 to 9 (BPG 100) showed comparable CS eluate HCD levels (0.3-1.5 ng/dose) as the CS eluate HCD level (1.2 ng/dose) in purification run 5 (BPG 200) (Table 21). Although the column performance was similar, the reduction of the column size improved the process efficiency by reducing the volume of CS eluate and buffer preparation when and will be important when moving to larger-scale manufacturing. FIG. 13 shows a typical chromatogram for the single virus peak eluted from the CS BPG 100 column (run 9).

As shown in Table 23, the overall HCD clearance for on-column Benzonase treatment (runs 5 to 9) was better than the batch-mode Benzonase treatment (runs 2 to 4). The percentage of HCD remaining after virus purification for Benzonase treatment ranged from 0.15-3.4% (runs 2 to 4), while the percentage of HCD remaining after virus purification for the on-column Benzonase treatment ranged from 0.02-0.15% (runs 5 to 9). The on-column Benzonase-treatment at the CS step was shown to have a higher overall HCD removal than the batch-mode Benzonase-treatment at SVH step, thus resulting in a lower DNA level of final bulk.

There are several advantages to using on-column Benzonase treatment compared to batch-mode Benzonase treatment. First, the process efficiency is increased by combining two process steps into one and replacing the 3 hours for Benzonase treatment at the SVH step with a 1 hour Benzonase treatment for the CS on-column step. Second, the total amount of Benzonase required in the purification process is reduced. Batch-mode Benzonase treatment requires one million units of Benzonase for a 20-L virus harvest, while the on-column Benzonase treatment only requires two hundred thousand units of Benzonase. Thus, the on-column Benzonase treatment reduces the total amount of Benzonase needed by five fold.

TFF2—Increase Diafiltration Volume on TFF2 to Increase Benzonase Clearance:

As shown in Table 20, the step recovery for TFF2 for all nine purification runs was consistently above 64% (64-150.8%). In run 3, the CS elution volume was 3.2 L. Using a 290 cm$^2$ hollow fiber, the CS eluate loading on the hollow fiber membrane increased to 110 L/m$^2$ and the total process time was 6 hours. A 1400 cm$^2$ hollow fiber membrane was used in the next two consecutive runs to avoid the long process time and to maintain the loading concentration at approximately 20-50 L/m$^2$ established in small-scale studies. However, starting with run 6, the column size was changed from 4 L to 1.4 L, and the elution volume also decreased to no more than 0.9 L. This reduction in eluate volume was directly proportional to the column size. In runs 6 to 9, a 290 cm$^2$ hollow fiber cartridge was used to maintain the CS eluate loading concentration at 20-50 L/m$^2$. FIG. 14 shows a typical flux trace curve of the TFF2 process for purification run 8, which was performed at 16000 s$^{-1}$ shear rate and a constant TMP of 21 psi. The TFF2 flux was reasonably stable throughout the diafiltration process indicating that the operating conditions did not cause any fouling. The flux ranged from 80-110 LMH for all purification runs.

The TFF2 buffer exchange volume was also increased from 5 diavolumes to 8 diavolumes to enhance the clearance of Benzonase. As shown in Table 24, when the process changed to an on-column Benzonase treatment step (run 5), the Benzonase level of the CS eluate was >75 ng/mL indicating that Benzonase binds to CS column and co-eluted with the virus product. Benzonase binding to the CS column was also confirmed by evaluating the flow-through samples of 1 CV to 4 CV after the 1×SPB. The flow-through samples were shown to have low Benzonase levels (Table 24). Thus, the TFF2 buffer exchange volume was increased from 5 diavolumes to 8 diavolumes in purification runs 8 and 9 to increase the Benzonase clearance to a level below the limit of detection (LOD). As a result, the Benzonase level was decreased an additional 4-5 fold by increasing the diafiltration from 5XDF to 8XDF. This change reduced the Benzonase level in the final bulk to below the LOD, which is less than 0.1 ng/dose (Table 24).

DFF2—Increase the Filter Size for Final Sterile Filtration of Final Bulk:

As shown in Table 20, the average step recovery using a 150 cm$^2$ and 300 cm$^2$ 0.22 μm final filter are 88.3-111.1% and 65.8-108%, respectively. The 300 cm$^2$ filter was chosen as the final filter size to avoid any plugging of the feed stream during final sterile filtration in the CTM campaign runs. The membrane area used to filter 0.6-1 L of final bulk was based on the small-scale studies that previously established the loading to be in the range of 20-150 L/m2. The filtration flow rate was 0.38 LPM for the 300 cm$^2$ filters and the flux for the filters was 760 LMH. The actual loading for the filters was 20-33 L/m$^2$, which is within the range determined from the small-scale studies.

Upstream (SUB) Process Harvest Time Change from 3 dpi to 2 dpi:

Starting with purification run 8, the viral harvest time was changed from 3 dpi (60-65 hr harvest) to 2 dpi (48 hr harvest). The peak viral titer was observed at 48 hours dpi, when an viral input of 0.001 to 0.003 FFU/cell was used. The change in harvest time resulted in a reduction in the starting HCD and HCP levels as shown in the SVH step for purification runs 8 and 9 (Table 21 and Table 22). This change also resulted in a lower impurity level of HCD and HCP in the final bulk product (Table 21 and Table 22) and therefore improved the final product quality.

The Implemented Purification Process Yielded Good Viral Recovery and Purity:

The complete implemented process was demonstrated in purification runs 8 and 9. The average overall titer recovery of these two runs was 43.4%, with an average HCD impurity level of 0.72 ng/dose (by PicoGreen) and 0.1 ng/dose (by PCR), HCP impurity level of 0.21 μg/dose and Benzonase impurity level of 0.0035 ng/dose, all of which are below the purified bulk specifications.

In summary, several changes were made to the initial purification process to improve the process efficiency and final product quality including, 1) the viral harvest was changed from 3 dpi to 2 dpi to result in a lower HCD and HCP impurity level in SVH, 2) the HCD treatment step was changed from batch-mode Benzonase treatment at SVH to CS on-column Benzonase treatment to improve overall HCD degradation and removal, 3) the target loading concentration of the CS resin was increased from 9.0 log$_{10}$FFA/mL to 9.5 log$_{10}$FFA/mL, which reduces the column size from 4 L to 1.4 L, 4) the final formulation buffer exchange volume for TFF2 was increased from 5 diavolumes to 8 diavolumes to improve Benzonase removal, and 5) the final sterile filtration loading was decreased by half to an average of 25 L/m$^2$ to avoid any plugging during final filtration in the CTM runs.

The final purification process is shown in FIG. 10 and the data for all the purification runs are summarized in Table 25. The average overall virus recovery based on titer for the improved purification process was 43.4%, with an average impurity level of 0.0035 ng/dose for Benzonase, 0.72 ng/dose (PicoGreen) and 0.1 ng/dose (PCR) for HCD and 0.19 μg/dose for HCP. These impurity levels are below specifications. The final bulks for purification runs 6 to 9 were analyzed by DNA size analysis using a direct-label method (psoralen-biotin) blot and a direct staining method (agarose gel). The predominant signal in these analysis showed a DNA size distribution of ≤500 bp (data not shown).

8.4 Example 4

Modified Purification Process for Cell Culture Produced Influenza

Figure 10B:
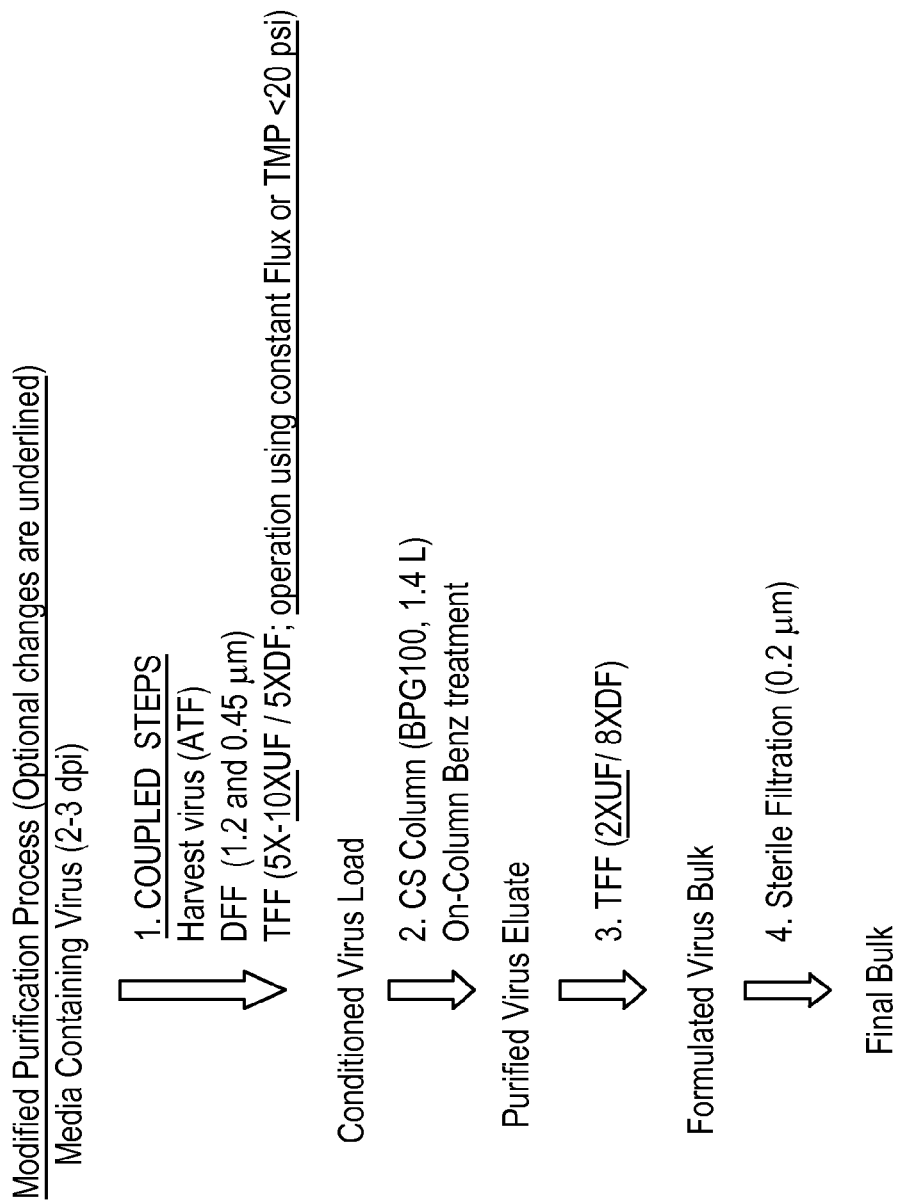

Additional modifications that can be made to the robust large scale purification process described in Section 8.3 are outlined in FIG. 10b and described in detail below. In particular, the harvest, clarification and TFF1 steps may be coupled to avoid the need for a harvest tank, reduce the number of manipulations and improve the overall processing time. For a smoother coupling operation TFF1 operation may be changed from constant TMP to constant Flux. Additionally, or alternatively, a lower TMP is utilized (lower than 20 psi, for example between about 10 psi (12,000 S$^{-1}$) to about 14.5 psi (16,000 S$^{-1}$)). A 2×UF step may added to the TFF2 step to decrease the bulk volume. Optionally, a 10XUF in used in TFF1 to potentially double the loading on all subsequent purification steps.

Table 26 summarizes the parameter changes, recovery, and HCD for several purification runs. These runs utilized virus produced in MediV SFM 110 without media exchange essentially as described above (see the Example provided in Section 8.1). All purification runs were performed essentially as described for the 1b process (see the Example provided in Section 8.3) except as noted below. Runs #25, #27 and #30 were performed by coupling the harvest, DFF and TFF1 steps. For these runs the TFF1 was run at constant Flux (50 LMH, shear rate of 12,000 s$^{-1}$). Runs #24, #26 and #31 were performed without coupling the harvest, DFF and TFF1 steps. For these runs the TFF1 was run at a lower TMP (10 psi, shear rate of 16,000 s$^{-1}$). The conditioned viral load was divided for the CS step and processed either at 2 mM MgCl$_2$ or 10 mM MgCl$_2$. DNA analysis showed that increasing the MgCl$_2$ concentration did not reduce DNA size (data not shown). However, in one instance the yield was reduced (see Table 26).

Table 27 summarizes the parameter changes, recovery, and HCD for several purification runs of virus produced in MediV SFM 105 with media exchange. These runs utilized virus produced essentially as described in International Patent Publication WO 08/105,931 (see in particular, Example 12). All purification runs were performed essentially as described for the 1b process (see the Example provided in Section 8.3) except as noted below. Runs #40, #41 and #42 were performed by coupling the harvest, DFF and TFF1 steps. For these runs the TFF1 was run either at constant Flux (35 LMH, shear rate of 12,000 S$^{-1}$) or at constant TMP (10 psi, shear rate of 12,000 s$^{-1}$). The runs with constant flux were performed at small scale and were processed only to the CS step. Run #43 was performed without coupling the harvest, DFF and TFF1 steps.

Together these studies indicate that material from MediV SFM 110 (no MX) and MediV SFM 105 (with MX) process show similar Flux/TMP characteristics. The use of lower shear (12,000 s$^{-1}$), lower TMP (10 psi), and lower flux (35 LMH) does result in longer step TFF process time but the overall process time can be shorter when coupling of the harvest, DFF and TFF steps is implemented. The final concentration of HCD for these purification runs was seen to be between 0.01-0.6 ng/dose which is comparable to that obtained in the 1b process described above. The overall yields were generally above 30%.

TABLE 26

Summary of HCD and Yield for Additional Parameter Changes no MX

| | Run No. | | | | | |
|---|---|---|---|---|---|---|
| | #24 | #25 | #26 | #27 | #30 | #31 |
| Strain | B/Flo | B/Flo | A/SD | A/SD | A/Uru | A/Uru |
| SVH volume (L) | 14.5 | 10 | 12.5 | 15 | 11 | 14.5 |
| TFF coupling | No | Yes | No | Yes | Yes | No |
| TFF mode | TMP | Flux | TMP | Flux | Flux | TMP |
| TFF1 Parameter | 16k s−1, 10 psi | 12k s−1, 50 LMH | 16k s−1, 10 psi | 16k s−1, 50 LMH | 12k s−1, 50 LMH | 16k s−1, 10 psi |
| Titer (SVH) (log$_{10}$ FFU/mL) | 8.5 | 8.5 | 8.9 | 8.9 | 8.8 | 9.1 |
| DNA (SVH) (ng/mL) | 277 | 2048 | 1672 | 2667 | 3649 | 1266 |
| Final Bulk DNA (ng/dose) | 0.23 | 0.39 | 0.07 | 0.09 | 0.59 | 0.05 |
| Final Bulk DNA (ng/dose) (10 mM MgCl$_2$) | 0.18 | 0.31 | 0.07 | 0.07 | 0.57 | 0.04 |
| PB Titer (2 mM MgCl2) | 10 | 10 | 10 | 9.9 | 9.9 | 10.8 |
| PB Titer (10 mM MgCl2) | 10.1 | 10 | 9.9 | 10 | 9.8 | 10.6 |
| Overall Yield (%) (2 mM MgCl2) | 43 | 36 | 13 | 23 | 42 | 69 |
| Overall Yield (%) (10 mM MgCl2) | 46 | 40 | 8 | 21 | 15 | 59 |

TABLE 27

Summary of HCD and Yield for Additional Parameter Changes with MX

| | Run No. | | | | | | |
|---|---|---|---|---|---|---|---|
| | #40** | | #41 | | #42 | | #43 |
| Strain | A/UR | | A/SD | | A/UR | | A/UR |
| Harvest (dpi) | 3 | | 3 | | 3 | | 3 |
| ATF/DFF Coupling | Yes | | Yes | | Yes | | No |
| Constant Flux/TMP | TMP | Flux* | TMP | Flux* | TMP | Flux* | TMP |
| TFF1 parameter | 12k s−1, 10 psi | 12k s−1, 35 LMH | 12k s−1, 10 psi | 12k s−1, 35 LMH | 12k s−1, 10 psi | 12k s−1, 35 LMH | 12k s−1, 10 psi |
| CS loading (log$_{10}$ FFU/mL) | 9.51 | 9.03 | 9.88 | 9.82 | 9.41 | 9.23 | 9.18 |
| Harvest titer (log$_{10}$ FFU/mL) | 8.7 | 8.7 | 8.8 | 8.8 | 8.4 | 8.4 | 8.2 |
| Harvest DNA (ng/mL) | 395 | 395 | 1105 | 1105 | 2923 | 2923 | 2362 |

TABLE 27-continued

Summary of HCD and Yield for Additional Parameter Changes with MX

| | #40** | | #41 | | #42 | | #43 |
|---|---|---|---|---|---|---|---|
| Final Bulk DNA (ng/dose) | 0.2 | 0.41* | 0.12 | 0.21* | 0.2 | 0.77* | 0.4 |
| Final Bulk titer ($\log_{10}$ FFU/mL) | 9.7 | 9.0* | 10* | 10.0 | 9.7* | 9.4* | 9.5 |
| Overall Yield | 17% | 22%* | 26% | 45%* | 32% | 43%* | 40% |

*Runs at Constant Flux were performed at small scale and processed only to CS column step
**#40 was held after TFF1 over weekend due to Friday harvest

8.5 Example 5

Downstream Manufacturing Process for Production of RSV

The development of a robust and scalable manufacturing process for cell based RSV vaccine required screening and optimization of different process parameters. Early downstream process development was performed at 10-L scale and the manufacturing process was scaled to 30-L. Viral harvest (VH) was produced in a bioreactor and harvested 7 days post infection (dpi). VH was pumped into a HyQtainer and clarified using 3-μm direct flow filtration. The initial filtration removes cell debris, microcarriers, 40-70% of the host cell DNA, and other particulates that were present in the VH. This step was followed by the enzymatic digestion of the remaining host cell DNA with Benzonase, a non-specific endonuclease at 10 U/mL of viral harvest. The reaction was stopped with 5 mM EDTA. After the Benzonase treatment, the VH was clarified by 0.65-μm filtration, and stabilized with 1/6 (v/v) dilution with stabilization buffer (for composition of stabilization buffer, refer to materials section). Stabilized VH can be stored for 12-16 hrs at room temperature (21±2° C.). A tangential flow filtration (TFF) was performed the next day with the stabilized VH material using a 500 kDa hollow fiber cartridge, 60 cm in path length and with an internal fiber diameter of 1 mm. The TFF step concentrates the stabilized VH and removes exogenous endonuclease, contaminants such as host cell DNA, and host cell proteins. The TFF step is also used to exchange the concentrated VH into a formulation buffer of choice. TFF step included 5-fold concentration of the stabilized VH and 7-fold buffer exchange with SPP2 buffer (for buffer composition, see the materials section). After the 7× diafiltration with SPP2 buffer, 4× diafiltration was performed with SPP3 buffer (for buffer composition, refer to materials section). The retentate was subsequently clarified using a terminal Sartorius Sartoclean cellulose acetate 3/0.8-μm filter. The titer recovery yield of the purification process and the titer and impurity profiles of the purified RSV drug substance for three 10-L and two 30-L bioreactor runs are described below as examples.

8.5.1 Materials and Methods

Materials, Reagent and Equipment:
Other materials, equipment and reagents which perform similarly may be readily substituted.

1) 10×SPG; 2180 mM sucrose, 1100 mM potassium phosphate, and 540 mM monosodium glutamate, pH 7.3 (HyClone, Ltd., Logan, Utah, Catalog# SH3A2025.01)
2) SPP1; 1498 mM sucrose, 200 mM potassium phosphate monobasic, 500 mM potassium phosphate dibasic, 1050 mM KCl, pH 7.2 (HyClone, Ltd., Logan, Utah, Catalog# SH3A2559.01)
3) SPP2; 730 mM sucrose, 28.5 mM potassium phosphate monobasic, 71.2 mM potassium phosphate dibasic, 150 mM KCl, pH 7.2 (HyClone, Ltd., Logan, Utah, Catalog# SH3A2560.03)
4) SPP3; 292 mM sucrose, 7.7 mM potassium phosphate monobasic, 12.3 mM potassium phosphate dibasic, 100 mM KCl, pH 7.0 (HyClone, Ltd., Logan, Utah, Catalog# SH3A2561.03)
5) Water for injection (WFI), 10 L/bag (HyClone, Ltd., Logan, Utah, Catalog#SH30221.24)
6) Water suitable for general laboratory use (VWR, West Chester, Pa., Catalog#BDH1168-4LP)
7) Benzonase endonuclease, purity grade I (EMD Chemicals, Gibbstown, N.J., Catalog#1.01697.00021, Lot# K38894897)
8) 1 M Magnesium chloride (Sigma, St Louis, Mo., Catalog# M-1028)
9) 0.5 M Ethylenediaminetetraacetic acid (EDTA) disodium salt solution (Sigma, St Louis, Mo., Catalog# E-7889)
10) 10 N Sodium hydroxide (VWR, West Chester, Pa., Catalog# VW3247-7)
11) 0.5 N Sodium hydroxide (VWR, West Chester, Pa., Catalog# VW3221-4)
12) 8 N Potassium hydroxide (VWR, West Chester, Pa., Catalog#200056-170)
13) Ethyl alcohol, anhydrous (VWR, West Chester, Pa., Catalog# BJAH090-4)
14) Sucrose (VWR, West Chester, Pa., Catalog# EM 1.07653.9028)
15) Potassium Phosphate Monobasic (VWR, West Chester, Pa., Catalog# JT3248-7)
16) Potassium Phosphate Dibasic (VWR, West Chester, Pa., Catalog# JT3250-7)
17) Potassium Chloride (VWR, West Chester, Pa., Catalog# EM-PX1405-5)
18) Sartopure PP2, 3-μm, 2000-cm$^2$ filter (Sartorius, Edgewood, N.Y., Catalog#5595302P9-00-A)
19) Sartopure PP2, 0.65-μm, 1000-cm$^2$ filter (Sartorius, Edgewood, N.Y., Catalog#5595305P8-00-A)
20) Sartopure PP2, 0.65-μm, 500-cm$^2$ filter (Sartorius, Edgewood, N.Y., Catalog#5595305P7-00-A)
21) Sartoclean Calif., 3.0+0.8 mm, 500-cm$^2$ filter (Sartorius, Edgewood, N.Y., Catalog#5625304E7-00-A)
22) Acro50 0.2-μm PTFE vent filter (Pall Corporation, East Hills, N.H., Catalog#4251)
23) 500 kDa Hollow fiber cartridge (membrane area: 850-cm$^2$, lumen ID: 1 mm) (GE Healthcare, Piscataway, N.J., Catalog# UFP-500-E-4×2MA)
24) 500 kDa Hollow fiber cartridge (membrane area: 2800-cm$^2$, lumen ID: 1 mm) (GE Healthcare, Piscataway, N.J., Catalog# UFP-500-E-6A)

25) ⅜" Polysulfone in-line hose barb (VWR, West Chester, Pa., Catalog#16001-592)
26) ⅜" Polysulfone silicone seal (VWR, West Chester, Pa., Catalog#16001-600)
27) Masterflex platinum-cured silicone tubing, L/S 36 (Cole-Parmer, Vernon Hills, Ill., Catalog# EW-96410-36)
28) Masterflex platinum-cured silicone tubing, L/S 24 (Cole-Parmer, Vernon Hills, Ill., Catalog# EW-96410-24)
29) Masterflex precision PharMed tubing, L/S16 (Cole-Parmer, Vernon Hills, Ill., Catalog#06485-16)
30) Platinum-cured silicone tubing, ½" ID×¾" OD (Cole-Parmer, Vernon Hills, Ill., Catalog# EW-95802-23)
31) Dow Corning Pharma reinforced tubing, ½" ID (Cole-Parmer, Vernon Hills, Ill., Catalog# EW-96108-10)
32) Quant-iT PicoGreen dsDNA Kit (Invitrogen, Eugene, Oreg., Catalog# P11496)
33) Coomassie Plus—The Better Bradford Assay Kit (Thermo Scientific, Rockford, Ill., Catalog#23236)
34) Benzonase ELISA Kit II (EMD Chemicals, Inc, Gibbstown, N.J., Catalog#1.01681.0002)
35) 1 M $MgCl_2$ (Sigma, St. Louis, Mo., Cat. No. M1028, lot #085K8920)
36)
37) 96-Well microplates (Greiner Bio-one, New York, N.Y., Catalog#655090)
38) 125-mL Polyethylene terephthalate glycol-modified (PETG) square media bottle (VWR, West Chester, Pa., Catalog#16159-130)
39) 1-L PETG square media bottle (VWR, West Chester, Pa., Catalog#16159-136)
40) 2-L PETG square media bottle (VWR, West Chester, Pa., Catalog#16159-138)
41) 10-L Flexboy assembly (Sartorius Stedim Biosystem, Edgewood, N.Y., Catalog#SH30712.02)
42) 20-L Flexboy assembly (Sartorius Stedim Biosystem, Edgewood, N.Y., Catalog#SH30712.03)
43) 50-L Flexboy assembly (Sartorius Stedim Biosystem, Edgewood, N.Y., Catalog#SH30712.04)
44) 10-L Polypropylene carboy (VWR, West Chester, Pa., Catalog#36494-090)
45) 20-L Polypropylene carboy (VWR, West Chester, Pa., Catalog#36494-092)
46) 2-mL Cryogenic polypropylene vials, sterile (VWR, West Chester, Pa., Catalog#66008-728)
47) Test paper pH 4-9 dual dispenser (VWR, West Chester, Pa., Catalog#60777-049)

Equipment
1) Pump, 520S (Watson Marlow, Wilmington, Mass., Catalog#050.7131.10A)
2) Pump, 620-Di N/R (Watson Marlow, Wilmington, Mass., Catalog#060.417N.02A)
3) Pump, 720SN/RE (Watson Marlow, Wilmington, Mass., Catalog#070.413N.E0A)
4) 12-mm Sta-Pure 620 LoadSure element with sanitary fittings (Watson Marlow, Wilmington, Mass., Catalog#960.0120.PFT)
5) 19-mm Sta-Pure 720 LoadSure element with sanitary fittings (Watson Marlow, Wilmington, Mass., Catalog#960.0190.PFT)
6) Biological safety cabinet, Purifier Class II (Labconco, San Ramon, Calif., Model#96212042726)
7) Wave mixer (Wavebiotech, LLC, Somerset, N.J., Part# MIXER20/50EH)
8) Scale, Max: 3100 g (Sartorius Mechatronics, Catalog# BL3100)
9) Scale, Max: 60 kg (Sartorius Mechatronics, Catalog# EB60EDE-I)
10) Scale, Max: 150 kg (Sartorius Mechatronics, Catalog# E150EDE-I)
11) Standard FlexStand with pressure gauges (GE Healthcare, Piscataway, N.J., Catalog#FS-01S-30)
12) Low void volume FlexStand with pressure gauges (GE Healthcare, Piscataway, N.J., Catalog# FS-03LVS-30)
13) SciPres Pressure Flow Cell (Scilog, Middleton, Wis., Part#080-699PS-5)
14) Molecular Dynamics SpectraMax GEMINI microplate reader (Molecular Devices, Sunnyvale, Calif., Part# EM)
15) SoftMax Pro program, version 4.8 (Molecular Devices, Sunnyvale, Calif., Part#SMP53-GXP-SITE)
16) Winwedge, standard edition (TAL Technologies, Philadelphia, Pa., Part# Winwedge Std)

Purification of RSV from 10-L Bioreactor Harvests

RSV VH (~8 L) obtained from a 10-L bioreactor run was clarified with a 3.0-µm filter (Sartopure PP2, 2000 $cm^2$) at a flux of 0.41 mL/min/$cm^2$. The resulting filtrate was incubated in a 10-L HyQtainer assembly at 32±3° C. for 3 h on a Wave mixer with 10 U of Benzonase/mL of viral harvest and 5 mM $MgCl_2$ to degrade host cell DNA. The reaction was stopped with the addition of EDTA to a final concentration of 5 mM. Benzonase-treated harvest was clarified with a 0.65-µm (Sartopure PP2, 500 $cm^2$) filter at a flux of 3.0 mL/min/$cm^2$. The filtrate was then stabilized to a final concentration of 1×SPP using a 7× concentrated solution of SPP1 buffer and stored at room temperature (21±2° C.) overnight (12-16 hrs). The stabilized viral harvest was concentrated 5-fold and diafiltered 7-fold with SPP2 buffer followed by 4-fold diafiltration with SPP3 buffer. The TFF process was performed using a 850 $cm^2$ hollow fiber cartridge. The load ratio (weight of viral feed per membrane area), shear rate, and transmembrane pressure (TMP) were 10 g feed/$cm^2$, 12,000 $s^{-1}$ and 15 psi, respectively (see table 1 for TFF parameters). The retentate was clarified with a 3/0.8-µm (Sartoclean Calif., 500 $cm^2$) filter at a flux of 3.8 mL/min/$cm^2$. This filter was subsequently washed by a volume of SPP3 that was one-third the volume of the retentate. The resulting filtrates were combined, flash-frozen or control rate frozen as 100-mL aliquots in 125-mL PETG bottles, and stored at −80° C. Samples (1 or 10 mL) were also collected after each purification step for analyses. They were flash-frozen and stored at −80° C.

Purification of MEDI-559 from 30-L Bioreactor Harvest

A RSV viral harvest (~25 L) obtained from a 30-L bioreactor run was clarified with two 3.0-µm filters (Sartopure PP2, 2000 $cm^2$) that were arranged in parallel at a flux of 0.41 mL/min/$cm^2$. The resulting filtrate was incubated in a 50-L HyQtainer assembly at 32° C. for 3 h on a Wave mixer with 10 U of Benzonase/mL of viral harvest and 5 mM $MgCl_2$ to degrade host cell DNA. The reaction was stopped with the addition of EDTA to a final concentration of 5 mM. Benzonase-treated harvest was clarified with a 0.65-µm (Sartopure PP2, 1000 $cm^2$) filter at a flux of 3.0 mL/min/$cm^2$. The filtrate was then stabilized to a final concentration of 1×SPP using a 7× concentrated solution of SPP1 buffer) and stored at room temperature (21±2° C.) overnight (12-16 hrs). The TFF process was performed using a 2800 $cm^2$ hollow fiber cartridge. The load ratio (weight of viral feed per membrane area), shear rate, and transmembrane pressure (TMP) were 10 g feed/$cm^2$, 12,000 $s^{-1}$ and 15 psi, respectively (see Table 28 for TFF parameters). The retentate was clarified with 3/0.8-µm (Sartoclean Calif., 500 or 1000 $cm^2$) filter at a flux of 3.8 mL/min/$cm^2$. This filter was subsequently washed with a volume of SPP3 that was one-third the volume of the retentate. The resulting filtrates were combined, flash-frozen or control rate frozen as 100-mL aliquots in 125-mL PETG bottles, and stored at −80° C. Samples (1- or 10-mL) were also collected after each purification step for analyses. They were flash-frozen and stored at −80° C.

TABLE 28

Operating Parameters for Tangential Flow Filtration Studies

| Exp. No. | Viral Harvest | Viral Seed | HF Cartridge | Feed Flow Rate (L/min) | TFF Process | TFF System |
|---|---|---|---|---|---|---|
| 1 | BR09-068 | V559-2a | UFP-500-E-4X2MA | 3.53 | 5X UF ⇨ 7X DF with SPP2 ⇨ 4X DF with SPP3 | Low-Void Volume Flexstand |
| 2 | BR09-069 | V559-2a | UFP-500-E-4X2MA | 3.53 | 5X UF ⇨ 7X DF with SPP2 ⇨ 4X DF with SPP3 | Low-Void Volume Flexstand |
| 3 | BR09-073 | V559-2a | UFP-500-E-4X2MA | 3.53 | 5X UF ⇨ 7X DF with SPP2 ⇨ 4X DF with SPP3 | Low-Void Volume Flexstand |
| 4 | SUB 090529 | V559-1b | UFP-500-E-6A | 12.0 | 5X UF ⇨ 7X DF with SPP2 ⇨ 4X DF with SPP3 | Standard Flexstand |
| 5 | SUB 09-005 | V559-2a | UFP-500-E-6A | 12.0 | 5X UF ⇨ 7X DF with SPP2 ⇨ 4X DF with SPP3 | Standard Flexstand |

Infectivity Determination by Fluorescent Focus Assay

The viral titer of the samples was determined by the VAS (Vaccine Analytical Science) group. This assay utilizes F protein specific monoclonal antibody to quantify virus in a test sample.

Total DNA Quantitation by Quant-iT PicoGreen dsDNA Assay

The total DNA concentration of the samples was determined using the Quant-iT PicoGreen dsDNA assay kit according to the manufacturer's instructions. Four serial dilutions (1:2) of the samples were prepared in duplicates. Standards ranging from 1.95 to 1000 ng/mL were prepared in triplicates. All dilutions were performed in a 96-well microplate using 1×SPG buffer. The fluorescence intensity emission was plotted against the standard DNA concentration. The total DNA concentration of the samples was determined by extrapolation from the linear regression fit of the standard curve, followed by adjustment with the appropriate dilution factor. The y-intercept of the fitted line was set at (0, 0) to enhance the accuracy of the extrapolated values for low DNA concentrations. The total DNA concentration reported for each sample is an average of the concentrations determined for the serial dilutions.

Residual Vero Host Cell DNA Quantitation by Real-Time PCR

The concentration of Vero host cell DNA in the samples was determined by the VAS group. The assay detects African Green monkey (Vero cell-derived) specific DNA by real time PCR, in samples containing cell substrate including vaccine viruses.

Total Protein Quantitation by Bradford Protein Assay

The total protein concentration of the samples was determined by using the Coomassie Plus (Bradford) assay kit with bovine serum albumin (BSA) as the standard according to SOP Q0169. Standards ranging from 2.5 to 25 µg/mL were prepared in triplicates. A 10-fold dilution of each sample was initially performed. Three serial dilutions (1:2) of each diluted sample were then prepared in triplicates. All dilutions were performed in a 96-well microplate using 1×SPG buffer. The absorbance at 595 nm was plotted against the standard BSA concentration. The total protein concentration of the samples was determined by the appropriate dilution factor. The total protein concentration reported for each sample is an average of the concentrations calculated for the serial dilutions.

Residual Vero Host Cell Protein Quantitation by ELISA

The concentration of residual Vero host cell protein in the samples was determined by the VAS group. This assay uses Enzyme-linked Immunoabsorbant Assay to quantitate African Green monkey (Vero cell-derived) specific proteins. The antibodies used are purified polyclonal antibodies raised against Vero cell lysates in goats.

Benzonase Quantitation by ELISA

The Benzonase concentration of the samples was determined by using the Benzonase Endonuclease ELISA kit. This assay uses Enzyme-linked Immunoabsorbant Assay to quantitate Benzonase. The primary antibody binds to Benzonase and the seconday antibody binds to Benzonase and primary antibody complex and detected colorimetricaly at 450 nm. The standard curve is generated using Benzonase stock.

Determination of RSV-F Protein Expression

The identity test for the presence of the RSV-F protein was determined by Western blot. In this assay, samples are run on SDS PAGE along with the markers, positive and negative controls. The protein bands are transferred from the SDS PAGE to nylon membrane using a transfer apparatus and a transfer buffer. The nylon membrane is incubated with RSV F monoclonal antibody which is in turn detected by binding of a seconday antibody.

DNA Sizing by Capillary Electrophoresis

DNA sizing was performed by the VAS (Vaccine Analytical Science) group. Samples are loaded on capillary electrophoresis to separate the DNA. Different sizes of DNA fragments are quantified by reading the relative fluorescence units.

Osmolality Determination

The osmolality of the samples was determined using osmometer from Advanced Instruments. First standards are run on the osmometer and then samples are loaded in sample tube and the osmolality reading is noted.

8.5.2 Results and Discussion

The performance of the RSV manufacturing process at the 30-L scale (SUB 092529 and SUB 09-005) was comparable to that at the 10-L scale (BRO9-068, BRO9-069, and BRO9-73). The overall recovery yield was between 6-14% and was consistent among the five runs (Table 29). The infectivity of the viral harvests ranged from 6.5-7.0 $\log_{10}$ FFU/mL, and that of the purified drug substance ranged from 6.0-6.7 $\log_{10}$ FFU/mL (Table 30). The titer for the viral harvest of SUB 090529 was particularly low, because this culture was infected with the viral seed V559-1b instead of V559-2b. Consequently, the titer of the resulting purified bulk was also the lowest of the five lots. Because V559-1b was produced in T-flasks by cell-scraping, it exhibits a high degree of heterogeneity, and its use may result in higher titer variability and lower infectivity than with the use of V559-2b, which was produced in roller bottles and prepared by dislodging the adhered cells with glass beads. Titer of SUB09-005 VH and the final bulk was also low because of the low cell density at the time of infection.

The residual Benzonase, host cell DNA, and host cell protein concentrations of the purified bulks all met the specifications proposed for RSV drug substance (Table 31). The percentage of residual DNA fragments that are <300 bp was greater than 80%, and the percentage that are >1000 bp was less than or equal to 5% (Table 32). The expression of the RSV-F protein was detected in all five lots of purified bulk, confirming the presence of RSV (Table 31).

CONCLUSION

The purification process developed for RSV from bioreactor-derived harvests was evaluated at the 10-L and 30-L scales to assess the robustness of the process and the quality of the final drug substance. The infectivity of the viral harvests, the infectivity of the purified bulks, and the overall titer recovery yield at both scales ranged from 6.5-7.0 $\log_{10}$ FFU/mL, 6.0-6.7 $\log_{10}$ FFU/mL, and 6-14%, respectively. The residual Benzonase, host cell protein, and host cell DNA concentrations of the purified bulks all met the specifications proposed for the RSV drug substance. In addition, more than 80% of the residual DNA fragments were <300 bp in size.

TABLE 29

Titer Recovery Yields of RSV Manufacturing Process at 10 and 30-L scales

| Step Titer Recovery Yield (%) | BR09-068 (10-L) | BR09-069 (10-L) | BR09-073 (10-L) | SUB 090529 (30-L) | SUB 09-005 (30-L) |
|---|---|---|---|---|---|
| 3-μm Filtration | 97 | 87 | 91 | 93 | 87 |
| Benzonase Treatment (10 U/mL, 32° C., 3 h) | 56 | 63 | 64 | 53 | 40 |
| 0.65-μm Filtration | 79 | 67 | 65 | 63 | 63.1 |
| Stabilization | 186 | 186 | 125 | 59 | 77.4 |
| Stabilization after Overnight Storage | 54 | 71 | 61 | 99 | 316.2 |
| 5X UF⇨7X DF with SPP2⇨4X DF with SPP3 | 32 | 43 | 59 | 74 | 21.6 |
| 3/0.8-μm Filtration + Filter Wash | 53 | 67 | 46 | 85 | 40 |
| Overall | 7 | 14 | 8 | 11 | 6 |

TABLE 30

Infectivity, Total DNA Concentration, and Total Protein Concentration of Viral Harvest and Purified Drug Substance from 10-L and 30-L RSV Bioreactor Runs

| | Attributes | Manufacturing Process Specifications | BR09-068 (10-L) | BR09-069 (10-L) | BR09-073 (10-L) | SUB 092529 (30-L) | SUB 09-005 (30-L) |
|---|---|---|---|---|---|---|---|
| Viral Harvest | Infectivity ($\log_{10}$ FFU/mL) | — | 6.95 | 7.02 | 6.83 | 6.50 | 6.65 |
| | Total DNA (ng/mL) | — | 587 | 807 | 454 | 627 | 692.4 |
| | Total Protein (μg/mL) | — | 153 | 134 | 156 | 115 | 103.5 |
| Purified Drug Substance | Infectivity ($\log_{10}$ FFU/mL) | ≥6.0 $\log_{10}$ FFU/mL | 6.31 | 6.65 | 6.27 | 6.01 | 6.0 |
| | Total DNA (ng/mL) | — | 71 | 79 | 26 | 48 | 35.1 |
| | Total Protein (μg/mL) | — | 106 | 120 | 84 | 36 | 58.3 |

TABLE 31

Attributes of RSV Drug Substance Purified from 10-L and 30-L Bioreactor Runs

| Attributes | Manufacturing Process Specification | BR09-068 (10-L) | BR09-069 (10-L) | BR09-073 (10-L) | SUB 090529 (30-L) | SUB 09-005 (30-L) |
|---|---|---|---|---|---|---|
| Residual Host Cell DNA (ng/$10^5$ dose) | <100 ng/$10^5$ dose | 0.30 | 0.19 | 0.12 | 0.89 | —* |
| Residual Host Cell Protein (μg/$10^5$ dose) | <40 μg/$10^5$ dose | 1.02 | 0.54 | 0.35 | —* | —* |
| Residual Benzonase (ng/$10^5$ dose) | <0.1 ng/$10^5$ dose | 0.01 | BLD | 0.01 | BLD | BLD |
| Osmolality (mOs/kg) | Report results | 607 | 596 | 595 | 600 | 597 |
| pH | Report results | 7.14 | 7.13 | 7.12 | 7.11 | 7.12 |
| RSV-F Protein Expression | Positive | Positive | Positive | Positive | Positive | Positive |

*Analysis underway

TABLE 32

Size Distribution of Residual DNA Fragments after 0.65-μm Filtration and in the Purified Drug Substance

| Lot Number | Process Step | <300 bp | 300-500 bp | 500-1000 bp | >1000 bp |
|---|---|---|---|---|---|
| BR09-068 | After 0.65-μm Filtration | 74.6 | 10.8 | 7.1 | 7.6 |
| (10-L) | Purified Drug Substance | 83.4 | 8.5 | 4.1 | 3.9 |
| BR09-069 | After 0.65-μm Filtration | 72.4 | 10.2 | 7.9 | 9.5 |
| (10-L) | Purified Drug Substance | 81.8 | 8.6 | 4.8 | 4.7 |
| BR09-073 | After 0.65-μm Filtration | 72.5 | 10.2 | 7.5 | 9.9 |
| (10-L) | Purified Drug Substance | 87.9 | 6.6 | 2.8 | 2.6 |
| SUB 090520 | After 0.65-μm Filtration | 68.9 | 13.2 | 8.3 | 9.7 |
| (30-L) | Purified Drug Substance | 83.2 | 7.8 | 4.1 | 5.0 |
| SUB 09-005 | After 0.65-μm Filtration | 68.7 | 9.5 | 9.1 | 12.7 |
| (30-L) | Purified Drug Substance | 82.9 | 8.9 | 4.4 | 3.8 |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes. In addition, the following U.S. provisional patent applications: 60/845,121 filed Sep. 16, 2006; 60/871,721 filed Dec. 22, 2006; 60/917,008 filed May 9, 2007; 60/951,813 filed Jul. 25, 2007; 61/099,749 filed Sep. 24, 2008; and U.S. patent application Ser. No. 11/855,769 filed Sep. 14, 2007 are incorporated by reference in their entirety.

The invention claimed is:

1. A method of purifying respiratory syncytial virus from virus-infected cells, wherein the method comprises:
   a) clarifying a viral harvest to form a clarified viral harvest, wherein clarifying comprises:
      i. filtering the viral harvest by direct flow filtration (DFF) through at least one clarification filter having a pore size of between about 3 micrometers to about 10 micrometers;
      ii. treating the viral harvest with a non-specific endonuclease; and
      iii. filtering the viral harvest by DFF through at least one clarification filter having a pore size of between about 0.45 micrometers to about 3 micrometers;
   b) stabilizing the clarified viral harvest with a stabilization buffer comprising sucrose, phosphate or Tris with NaCl salt or KCl salt to form a stabilized viral harvest;
   c) concentrating the stabilized viral harvest by tangential flow filtration (TFF) and performing buffer exchange by diafiltration (DF) using a hollow fiber cartridge with a molecular weight cut off (MWCO) of 500 kDa to form a concentrated viral harvest; and
   d) after (c), sterilizing the concentrated viral harvest by DFF through at least one clarification filter having a pore size of between about 0.8 micrometers to about 0.45 micrometers to form a sterilized viral harvest; whereby the respiratory syncytial virus is purified from the virus-infected cells and has a final viral infectivity titer of at least 5.7 $\log_{10}$ FFU/mL.

2. The method according to claim 1, wherein the method further comprises a step of purification by ion-exchange chromatography.

3. The method according to claim 1, wherein an exchange buffer of step (c) comprises about 10-25% w/v sucrose, about 150 mM to 10 mM potassium phosphate and about 175 mM to 50 mM KCl pH 7.0-7.4.

4. The method according to claim 1, wherein the respiratory syncytial virus is is rA2cp248/404/1030ASH.

5. The method according to claim 1, wherein the viral harvest is stabilized with a buffer comprising about 150 mM to 50 mM potassium phosphate, about 250 mM to 175 mM sucrose, and about 175 mM to 125 mM NaCl or KCl, pH 7.0-7.4.

6. The method according to claim 1, wherein step (c) results in a 5× concentration and least 5 diavolumes of buffer are exchanged.

7. The method according to claim 1, wherein the non-specific nuclease is exposed to the viral harvest for between about 120 minutes and 210 minutes.

8. The method according to claim 1, wherein the respiratory syncytial virus is a live respiratory syncytial virus.

9. The method according to claim 1, wherein the respiratory syncytial virus is a live attenuated respiratory syncytial virus.

* * * * *